US009682109B2

(12) United States Patent
Bartholomeusz et al.

(10) Patent No.: US 9,682,109 B2
(45) Date of Patent: *Jun. 20, 2017

(54) ANTIVIRAL RESISTANCE MUTANTS AND APPLICATIONS THEREOF

(75) Inventors: Angeline Ingrid Bartholomeusz, Carnegie (AU); Stephen Locarnini, Balaclava (AU); Anna Ayres, Brunswick West (AU); Margaret Littlejohn, Coburg (AU); Peter William Angus, East Ivanhoe (AU)

(73) Assignee: ABL SA, Luxembourg (LU)

( * ) Notice: Subject to any disclaimer, the term of this patent is extended or adjusted under 35 U.S.C. 154(b) by 1010 days.

This patent is subject to a terminal disclaimer.

(21) Appl. No.: 11/913,106

(22) PCT Filed: Oct. 20, 2006

(86) PCT No.: PCT/AU2006/001563
§ 371 (c)(1),
(2), (4) Date: May 27, 2008

(87) PCT Pub. No.: WO2007/045045
PCT Pub. Date: Apr. 26, 2007

(65) Prior Publication Data
US 2008/0274083 A1    Nov. 6, 2008

(30) Foreign Application Priority Data

Oct. 21, 2005    (AU) .................................. 2005905862

(51) Int. Cl.
| | |
|---|---|
| *C12Q 1/68* | (2006.01) |
| *C12N 15/117* | (2010.01) |
| *A61P 31/20* | (2006.01) |
| *A61K 35/76* | (2015.01) |
| *C12N 7/00* | (2006.01) |
| *C12Q 1/18* | (2006.01) |

(52) U.S. Cl.
CPC ............... *A61K 35/76* (2013.01); *C12N 7/00* (2013.01); *C12Q 1/18* (2013.01); *C12N 2730/10132* (2013.01)

(58) Field of Classification Search
None
See application file for complete search history.

(56) References Cited

U.S. PATENT DOCUMENTS

| 7,384,747 | B2* | 6/2008 | Bartholomeusz et al. ........ 435/5 |
| 8,859,198 | B2* | 10/2014 | Bartholomeusz et al. ........ 435/5 |
| 2004/0029110 | A1* | 2/2004 | Stuyver et al. ................... 435/5 |
| 2004/0194155 | A1 | 9/2004 | Delaney et al. |
| 2006/0051743 | A1 | 3/2006 | Bartholomeusz et al. |
| 2006/0190186 | A1* | 8/2006 | Bartholomeusz et al. ..... 702/19 |

FOREIGN PATENT DOCUMENTS

| CA | 2309379 A1 | 12/2001 |
| WO | WO 03/080824 A1 | 10/2003 |
| WO | WO 03/087351 A1 | 10/2003 |
| WO | WO 2005/042733 A1 | 5/2005 |
| WO | WO 2006/034545 A1 | 4/2006 |
| WO | WO 2006/097284 A1 | 9/2006 |
| WO | WO 2006/105597 A1 | 10/2006 |
| WO | WO 2007/045045 A1 | 4/2007 |

OTHER PUBLICATIONS

Tacke, F et al. 2004 "Influence of mutations in the Hepatitis B Virus genome on virus replication and drug resistance—Implications for novel antiviral strategies" *Current Medicinal Chemistry* 11:2667-2677.
Angus, P. et al. 2003 "Resistance to adefovir dipivoxil therapy associated with the selection of a novel mutation in the HBV polymerase" *Gastroenterology* 125(2): 292-297.
Germer, J.J. et al. 2003 "Characterization of hepatitis B virus surface antigen and polymerase mutations in liver transplant recipients pre- and post-transplant" *Am. J. of Transplantation* 3:743-753.
Jolivet-Reynaud, C. et al. 2001 "Localization of hepatitis B surface antigen epitopes present on variants and specifically recognized by anti-hepatitis B surface antigen monoclonal antibodies". *J. of Med. Virol.* 65:241-249.
Locarnini, S. 2004 "Molecular virology of hepatitis B virus". *Seminars in Liver Disease* 24(1):3-10.
Sablon, E & Shapiro, F. 2005 "Advances in molecular diagnosis of HBV infection and drug resistance". *Int. J. of Medical Sciences* 2(1):8-16.
Torresi, J. et al. 2002 "Restoration of replication phenotype of lamivudine-resistant hepatitis B virus mutants by compensatory changes in the "fingers" subdomain of the viral polymerase selected as a consequence of mutations in the overlapping S gene" *Virology*, 299(11): 88-99.
Torresi, J. et al. 2002 "The virological and clinical significance of mutations in the overlapping envelope and polymerase genes of hepatitis B virus", *J. of Clin. Virol.* 25(2):97-106.

(Continued)

*Primary Examiner* — Maria Marvich
(74) *Attorney, Agent, or Firm* — Andrews Kurth Kenyon LLP; David Bradin

(57) ABSTRACT

The present invention relates generally to viral variants exhibiting reduced sensitivity to agents such as nucleoside or nucleotide analogs or other DNA polymerase antagonists and/or reduced interactivity with immunological reagents. More particularly, the present invention is directed to hepatitis B virus (HBV) variants exhibiting complete or partial resistance to nucleoside or nucleotide analogs or other DNA polymerase antagonists and/or reduced interactivity with antibodies to viral surface components including reduced sensitivity to these antibodies. The present invention further contemplates assays for detecting such viral variants, which assays are useful in monitoring anti-viral therapeutic regimens and in developing new or modified vaccines directed against viral agents and in particular HBV variants. The present invention also contemplates the use of the viral variants to screen for and/or develop or design agents capable of inhibiting infection, replication and/or release of the virus.

4 Claims, 25 Drawing Sheets

(56) References Cited

Brunelle, M-N., et al. 2005 "Susceptibility to Antivirals of a Human HBV Strain with Mutations Conferring Resistance to Both Lamivudine and Adefovir" *Hepatology* 41:1391-1398.

Stuyver, L,J. et al. 2001 "Nomenclature for Antiviral-Resistant Human Hepatitis B Virus Mutations in the Polymerase Region" *Hepatology* 33: 751-757.

Tenney, D.J., et al. 2004"Clinical Emergence of Entecavir-Resistant Hepatitis B Virus Requires Additional Substitutions in Virus Already Resistant to Lamivudine" *Antimicrobial Agents and Chemotherapy* 48: 3498-3507.

Walters, K-A., et al. 2003 "Generation of Stable Cell Lines Expressing Lamivudine-Resistant Hepatitis B Virus for Antiviral-Compound Screenin", *Antimicrobial Agents and Chemotherapy* 47: 1936-1942.

\* cited by examiner

Sample 14 02579618 nt sequence

```
         10        20        30        40        50
AAGCCGCCTCCTGCCTCCACCAATCGCCAGTCAGGACGGCAGCCTACCCC 60        70        80        90       100
GCTGTCTCCACCTTTGAGAGACACTCATCCTCAGGCGCAGTGGAAACCCA 110       120       130       140       150
CAACCTTCCACCAAACTCTGCAAGCTCCACCTGCTGGTGGCTCCAGTTCC 160       170       180       190       200
GGAACAGTAAACCCTGTTCCGACTACTGCCTCTCACATATCGTCAATCTT 210       220       230       240       250
CTCGAGGATTGGGGACCCTGCGCTGAATATGGAGAACATCACATCAGGAT 260       270       280       290       300
TCCTAGGACCCCTTCTCGTGTTACAGGCGGGGTTTTCTTGTTGACAAGA 310       320       330       340       350
ATCCTCACAATACCGAAGAGTCTAGACTCGTGGTGGACTTCTCTCAATTT 360       370       380       390       400
TCTAGGGGAACCACCGTGTGTCTTGGCCAAAATTCGCAGTCCCCAACCT 410       420       430       440       450
CCAATCACTCACCAACCTCCTGTCCTCCGACTTGTCCTGGTTATCGCTGG 460       470       480       490       500
ATGTGTCTGCGGCGTTTTATCATATTCCTCTTCATCCTGCTGCTATGCCT 510       520       530       540       550
CATCTTCTTGTTGGTTCTTCTGGACTATCAAGGTATGTTGCCCGTTTGTC 560       570       580       590       600
CTCTAATTCCAGGATCCTCAACCACCAGCACGGGAACATGCCGAACTTGC 610       620       630       640       650
ACGACTCCTGCTCAAGGAACCTCTATGTATCCCTCCTGTTGCTGTACCAA 660       670       680       690       700
ACCTTCGGACGGAAATTGCACCTGTATTCCCATCCCATCATCCTGGGCTT 710       720       730       740       750
TCGGAAAATTCCTATGGGAGTGGGCCTCAGCCCGTTTCTCATGGCTCAGT 760       770       780       790       800
TTGGTAGTGCCATTTGTTCAGTGGTTCGTAGGGCTTTCCCCCACTGTTTG 810       820       830       840       850
GCTTTCATTTATGTGGATGATGTGGTATTGGGGGCCAAGTCTGTACAGCA 860       870       880       890       900
TCTTGAGTCCCTTTTTACCGCTGTTACCAATTTTCTTTTGTCTCTGGGTA 910       920       930       940       950
TACATTTGAACCCTRACAAAACAAAGAGATGGGGTTACTCCCTAAATTTT 960       970       980       990      1000
ATGGGCTATGTCATTGGAWGTTATGGGTCCTTGCCACAAGAACACATCGT

1010
ACATAAAATCAAAG
```

Figure 4A

Sample 14 02579618: HBV POL sequence

```
         10         20         30         40         50
AASCLHQSPVRTAAYPAVSTFERHSSSGAVETHNLPPNSASSTCWWLQFR 60         70         80         90        100
NSKPCSDYCLSHIVNLLEDWGPCAEYGEHHIRIPRTPSRVTGGVFLVDKN 110        120        130        140        150
PHNTEESRLVVDFSQFSRGNHRVSWPKFAVPNLQSLTNLLSSDLSWLSLD 160        170        180        190        200
VSAAFYHIPLHPAAMPHLLVGSSGLSRYVARLSSNSRILNHQHGNMPNLH 210        220        230        240        250
DSCSRNLYVSLLLLYQTFGRKLHLYSHPIILGFRKIPMGVGLSPFLMAQF 260        270        280        290        300
GSAICSVVRRAFPHCLAFIYVDDVVLGAKSVQHLESLFTAVTNFLLSLGI 310        320        330
HLNPXKTKRWGYSLNFMGYVIGXYGSLPQEHIVHKIK
```

Figure 4B

Sample 14 02579618: HBV HBsAg sequence

```
          10         20         30         40         50
  KPPPASTNRQSGRQPTPLSPPLRDTHPQAQWKPTTFHQTLQAPPAGGSSS 60         70         80         90        100
  GTVNPVPTTASHISSIFSRIGDPALNMENITSGFLGPLLVLQAGFFLLTR 110        120        130        140        150
  ILTIPKSLDSWWTSLNFLGGTTVCLGQNSQSPTSNHSPTSCPPTCPGYRW 160        170        180        190        200
  MCLRRFIIFLFILLLCLIFLLVLLDYQGMLPVCPLIPGSSTTSTGTCRTC 210        220        230        240        250
  TTPAQGTSMYPSCCCTKPSDGNCTCIPIPSSWAFGKFLWEWASARFSWLS 260        270        280        290        300
  LVVPFVQWFVGLSPTVWLSFMWMMWYWGPSLYSILSPFLPLLPIFFCLWV

```
Sample 15 03505860 HBV nt sequence
          10         20         30         40         50
AAGCCGCCTCCTGCCTCCACCAATCGCCAGTCAGGACGGCAGCCTACCCC
          60         70         80         90        100
SCTKTCTCCACCTTTGAGAGACACTCATCCTCAGGCGCAGTGGAAACCCA
         110        120        130        140        150
CAACCTTCCACCAAACTCTGCAAGCTCCACCTGCTGGTGGCTCCAGTTCC
         160        170        180        190        200
GGAACAGTAAACCCTGTTCCGACTACTGCCTCTCACATATCGTCAATCTT
         210        220        230        240        250
CTCGAGGATTGGGGACCCTGCGCTGAATATGGAGAACATCACATCAGGAT
         260        270        280        290        300
TCCTAGGACCCCTTCTCGTGTTACAGGCGGGGTTTTCTTGTTGACAAGA
         310        320        330        340        350
ATCCTCACAATACCGAAGAGTCTAGACTCGTGGTGGACTTCTCTCAATTT
         360        370        380        390        400
TCTAGGGGGAACCACCGTGTGTCTTGGCCAAAATTCGCAGTCCCCAACCT
         410        420        430        440        450
CCAATCACTCACCAACCTCCTGTCCTCCGACTTGTCCTGGTTATCGCTGG
         460        470        480        490        500
ATGTGTCTGCGGCGTTTTATCATATTCCTCTTCATCCTGCTGCTATGCCT
         510        520        530        540        550
CATCTTCTTGTTGGTTCTTCTGGACTATCAAGGTATGTTGCCCGTTTGTC
         560        570        580        590        600
CTCTAATTCCAGGATCCTCAACCACCAGCACGGGAACATGCCGAACTTGC
         610        620        630        640        650
ACGACTCCTGCTCAAGGAACCTCTATGTATCCCTCCTGTTGCTGTACCAA
         660        670        680        690        700
ACCTTCGGACGGAAATTGCACCTGTATTCCCATCCCATCATCCTGGGCTT
         710        720        730        740        750
TCGGAAAATTCCTATGGGAGTGGGCCTCAGCCCGTTTCTCATGGCTCAGT
         760        770        780        790        800
TTGGTAGTGCCATTTGTTCAGTGGTTCGTAGGGCTTTCCCCCACTGTTTG
         810        820        830        840        850
GCTTTCATTTATGTGGATGATGTGGTATTGGGGGCCAAGTCTGTACAGCA
         860        870        880        890        900
TCTTGAGTCCCTTTTTACCGCTGTTACCAATTTTCTTTTGTCTCTGGGTA
         910        920        930        940        950
TACATTTGAACCCTRACAAAACAAAGAGATGGGGTTACTCCCTAAATTTT
         960        970        980        990       1000
ATGGGCTATGTCATTGGAWGTTATGGGTCCTTGCCACAAGAACACATCGT
        1010
ACATAAAATCAAA
```

Figure 5A

Sample 15 03505860 HBV Pol sequence

```
         10        20        30        40        50
AASCLHQSPVRTAAYPXXSTFERHSSSGAVETHNLPPNSASSTCWWLQFR 60        70        80        90       100
NSKPCSDYCLSHIVNLLEDWGPCAEYGEHHIRIPRTPSRVTGGVFLVDKN 110       120       130       140       150
PHNTEESRLVVDFSQFSRGNHRVSWPKFAVPNLQSLTNLLSSDLSWLSLD 160       170       180       190       200
VSAAFYHIPLHPAAMPHLLVGSSGLSRYVARLSSNSRILNHQHGNMPNLH 210       220       230       240       250
DSCSRNLYVSLLLLYQTFGRKLHLYSHPIILGFRKIPMGVGLSPFLMAQF 260       270       280       290       300
GSAICSVVRRAFPHCLAFIYVDDVVLGAKSVQHLESLFTAVTNFLLSLGI 310       320       330
HLNPXKTKRWGYSLNFMGYVIGXYGSLPQEHIVHKIK
```

Figure 5B

```
Sample 15 03505860 HBV HBsAg sequence
         10        20        30        40        50
KPPPASTNRQSGRQPTPLSPPLRDTHPQAQWKPTTFHQTLQAPPAGGSSS 60        70        80        90       100
GTVNPVPTTASHISSIFSRIGDPALNMENITSGFLGPLLVLQAGFFLLTR 110       120       130       140       150
ILTIPKSLDSWWTSLNFLGGTTVCLGQNSQSPTSNHSPTSCPPTCPGYRW 160       170       180       190       200
MCLRRFIIFLFILLLCLIFLLVLLDYQGMLPVCPLIPGSSTTSTGTCRTC 210       220       230       240       250
TTPAQGTSMYPSCCCTKPSDGNCTCIPIPSSWAFGKFLWEWASARFSWLS 260       270       280       290       300
LVVPFVQWFVGLSPTVWLSFMWMMWYWGPSLYSILSPFLPLLPIFFCLWV

Sample 16 03534346 HBV nt

```
        10        20        30        40        50
            AGCCGCCTCCTGCCTCCACCAATCGCCAGTCAGGACGGCAGCCTACCCCG
        60        70        80        90       100
            CTGTCTCCACCTTTGAGAGACACTCATCCTCAGGCGCAGTGGAAACCCAC
       110       120       130       140       150
            AACCTTCCACCAAACTCTGCAAGCTCCACCTGCTGGTGGCTCCAGTTCCG
       160       170       180       190       200
            GAACAGTAAACCCTGTTCCGACTACTGCCTCTCACATATCGTCAATCTTC
       210       220       230       240       250
            TCGAGGATTGGGGACCCTGCGCTGAATATGGAGAACATCACATCAGGATT
       260       270       280       290       300
            CCTAGGACCCCTTCTCGTGTTACAGGCGGGGTTTTCTTGTTGACAAGAA
       310       320       330       340       350
            TCCTCACAATACCGAAGAGTCTAGACTCGTGGTGGACTTCTCTCAATTTT
       360       370       380       390       400
            CTAGGGGGAACCACCGTGTGTCTTGGCCAAAATTCGCAGTCCCCAACCTC
       410       420       430       440       450
            CAATCACTCACCAACCTCCTGTCCTCCGACTTGWCCTGGTTATCGCTGGA
       460       470       480       490       500
            TGTGTCTGCGGCGTTTTATCATATTCCTCTTCATCCTGCTGCTATGCCTC
       510       520       530       540       550
            ATCTTCTTGTTGGTTCTTCTGGACTATCAAGGTATGTTGCCCGTTTGTCC
       560       570       580       590       600
            TCTAATTCCAGGATCCTCAACCACCAGCACGGGAACATGCCGAACTTGCA
       610       620       630       640       650
            CGACTCCTGCTCAAGGAACCTCTATGTATCCCTCCTGTTGCTGTACCAAA
       660       670       680       690       700
            CCTTCGGACGGAAATTGCACCTGTATTCCCATCCCATCATCCTGGGCTTT
       710       720       730       740       750
            CGGAAAATTCCTATGGGAGTGGGCCTCAGCCCGTTTCTCATGGCTCAGTT
       760       770       780       790       800
            TGGTAGTGCCATTTGTTCAGTGGTTCGTAGGGCTTTCCCCCACTGTTTGG
       810       820       830       840       850
            CTTTCATTTATGTGGATGATGTGGTATTGGGGGCCAAGTCTGTACAGCAT
       860       870       880       890       900
            CTTGAGTCCCTTTTTACCGCTGTTACCAATTTTCTTTTGTCTCTGGGTAT
       910       920       930       940       950
            ACATTTGAACCCTAACAAAACAAAGAGATGGGGTTACTCCCTAAATTTTA
       960       970       980       990      1000
            TGGGCTATGTCATTGGAWGTTATGGGTCCTTGCCACAAGAACACATCGTA
      1010
            CATAAAATCAAAGAA
```

Figure 6A

Sample 16 03534346 HBV POL

```
          10         20         30         40         50
   AASCLHQSPVRTAAYPAVSTFERHSSSGAVETHNLPPNSASSTCWWLQFR 60         70         80         90        100
   NSKPCSDYCLSHIVNLLEDWGPCAEYGEHHIRIPRTPSRVTGGVFLVDKN 110        120        130        140        150
   PHNTEESRLVVDFSQFSRGNHRVSWPKFAVPNLQSLTNLLSSDLXWLSLD 160        170        180        190        200
   VSAAFYHIPLHPAAMPHLLVGSSGLSRYVARLSSNSRILNHQHGNMPNLH 210        220        230        240        250
   DSCSRNLYVSLLLLYQTFGRKLHLYSHPIILGFRKIPMGVGLSPFLMAQF 260        270        280        290        300
   GSAICSVVRRAFPHCLAFIYVDDVVLGAKSVQHLESLFTAVTNFLLSLGI 310        320        330
   HLNPNKTKRWGYSLNFMGYVIGXYGSLPQEHIVHKIKE
```

Figure 6B

Sample 16  03534346 HBV HBsAg

```
            10         20         30         40         50
   PPPASTNRQSGRQPTPLSPPLRDTHPQAQWKPTTFHQTLQAPPAGGSSSG 60         70         80         90        100
   TVNPVPTTASHISSIFSRIGDPALNMENITSGFLGPLLVLQAGFFLLTRI 110        120        130        140        150
   LTIPKSLDSWWTSLNFLGGTTVCLGQNSQSPTSNHSPTSCPPTXPGYRWM 160        170        180        190        200
   CLRRFIIFLFILLLCLIFLLVLLDYQGMLPVCPLIPGSSTTSTGTCRTCT 210        220        230        240        250
   TPAQGTSMYPSCCCTKPSDGNCTCIPIPSSWAFGKFLWEWASARFSWLSL 260        270        280        290        300
   VVPFVQWFVGLSPTVWLSFMWMMWYWGPSLYSILSPFLPLLPIFFCLWVY

Sample 17 04511239 HBV nt
```
         10         20         30         40         50
CCCCCTGCTGGTGGCTCCAGTTCCGGAACAGTAAACCCTGTTCCGACTAC 60         70         80         90        100
TGCCTCTCACATATCGTCAATCTTCTCGAGGATTGGGGACCCTGCGCTGA 110        120        130        140        150
ATATGGAGAACATCACATCAGGATTCCTAGGACCCCTTCTCGTGTTACAG 160        170        180        190        200
GCGGGGTTTTCTTGTTGACAAGAATCCTCACAATACCGCAGAGTCTAGA 210        220        230        240        250
GTCGTGGTGGACTTCTCTCAATTTTCTAGGGGSAACCACCGTGTGTCTTG 260        270        280        290        300
GCCAAAATTCGCAGTCCCCAACCTCCAATCACTCACCAACCTCCTGTCCT 310        320        330        340        350
CCGACTTGACCTGGTTATCGCTGGATGTGACTGCGGCATTTTATCATATT 360        370        380        390        400
CCTCTTCATCCTGCTGCTATGCCTCATCTTCTTGTTGGTTCTTCTGGACT 410        420        430        440        450
ATCAAGGTATGTTGCCCGTTTGTCCTCTAATTCCAGGATCCTCAACCACC 460        470        480        490        500
AGCACGGGAACATGCCGAACTTGCACGACTCCTGCTCAAGGAACCTCTAT 510        520        530        540        550
GTATCCCTCCTGTTGCTGTACCAAACCTTCGGACGGAAATTGCACCTGTA 560        570        580        590        600
TTCCCATCCCATCATCCTGGGCTTTCGGAAAATTCCTATGGGAGTGGGCC 610        620        630        640        650
TCAGCCCGTTTCTCMTGGCTCAGTTTGGTAGTGCCATTTGTTCAGTGGTT 660        670        680        690        700
CGTAGGGCTTTCCCCCACTGTTTGGCTTTCATTTATGYGGATGATRTGGT 710        720        730        740        750
ATTGGGGGCCAAGTCTGTACAGCATCTTGAGTCCCTTTTTACCGCTGTTA 760        770        780        790        800
CCAATTTTCTTTTGTCTCTGGGTATACATTTGAACCCTAACAAAACAAAG 810        820        830        840        850
AGATGGGGTTACTCCCTAAATTTTATGGGCTATGTCATTGGATGTTATGG 860        870        880        890        900
GTCCTTGCCACAAGAACACATCATACATAAAATCAAAGAATGTTTTAGAA 910        920        930
AACTTCCTGTTAACAGGCCTATTGATTGGAAAGT
```

Figure 7A

Sample 17  04511239 HBV POL

```
          10        20        30        40        50
  PCWWLQFRNSKPCSDYCLSHIVNLLEDWGPCAEYGEHHIRIPRTPSRVTG 60        70        80        90       100
  GVFLVDKNPHNTAESRVVVDFSQFSRGNHRVSWPKFAVPNLQSLTNLLSS 110       120       130       140       150
  DLTWLSLDVTAAFYHIPLHPAAMPHLLVGSSGLSRYVARLSSNSRILNHQ 160       170       180       190       200
  HGNMPNLHDSCSRNLYVSLLLLYQTFGRKLHLYSHPIILGFRKIPMGVGL 210       220       230       240       250
  SPFLXAQFGSAICSVVRRAFPHCLAFIYXDDXVLGAKSVQHLESLFTAVT 260       270       280       290       300
  NFLLSLGIHLNPNKTKRWGYSLNFMGYVIGCYGSLPQEHIIHKIKECFRK

310
  LPVNRPIDWK
```

Figure 7B

Sample 17  04511239 HBV HBsAg

```
          10        20        30        40        50
PPAGGSSSGTVNPVPTTASHISSIFSRIGDPALNMENITSGFLGPLLVLQ 60        70        80        90       100
AGFFLLTRILTIPQSLESWWTSLNFLGXTTVCLGQNSQSPTSNHSPTSCP 110       120       130       140       150
PT*PGYRWM*LRHFIIFLFILLLCLIFLLVLLDYQGMLPVCPLIPGSSTT 160       170       180       190       200
STGTCRTCTTPAQGTSMYPSCCCTKPSDGNCTCIPIPSSWAFGKFLWEWA 210       220       230       240       250
SARFSWLSLVVPFVQWFVGLSPTVWLSFMXMXWYWGPSLYSILSPFLPLL

260
PIFFCLWVYI
```

Figure 7C

Sample 19 04553852 HBV nt

```
         10        20        30        40        50
TCCCCTGCTGGTGGCTCCAGTTCCGGAACAGTAAACCCTGTTCCGACTAC
         60        70        80        90       100
TGCCTCTCACATATCGTCAATCTTCTCGAGGATTGGGGACCCTGCGCTGA
        110       120       130       140       150
ATATGGAGAACATCACATCAGGATTCCTAGGACCCCTTCTCGTGTTACAG
        160       170       180       190       200
GCGGGGTTTTTCTTGTTGACAAGAATCCTCACAATACCGCAGAGTCTAGA
        210       220       230       240       250
GTCGTGGTGGACTTCTCTCAATTTTCTAGGGGCAACCACCGTGTGTCTTG
        260       270       280       290       300
GCCAAAATTCGCAGTCCCCAACCTCCAATCACTCACCAACCTCCTGTCCT
        310       320       330       340       350
CCGACTTGACCTGGTTATCGCTGGATGTGACTGCGGCATTTTATCATATT
        360       370       380       390       400
CCTCTTCATCCTGCTGCTATGCCTCATCTTCTTGTTGGTTCTTCTGGACT
        410       420       430       440       450
ATCAAGGTATGTTGCCCGTTTGTCCTCTAATTCCAGGATCCTCAACCACC
        460       470       480       490       500
AGCACGGGAACATGCCGAACTTGCACGACTCCTGCTCAAGGAACCTCTAT
        510       520       530       540       550
GTATCCCTCCTGTTGCTGTACCAAACCTTCGGACGGAAATTGCACCTGTA
        560       570       580       590       600
TTCCCATCCCATCATCCTGGGCTTTCGGAAAATTCCTATGGGAGTGGGCC
        610       620       630       640       650
TCAGCCCGTTTCTCCTGGCTCAGTTTGGTAGTGCCATTTGTTCAGTGGTT
        660       670       680       690       700
CGTAGGGCTTTCCCCCACTGTTTGGCTTTCATTTATGCGGATGATGTGGT
        710       720       730       740       750
ATTGGGGGCCAAGTCTGTACAGCATCTTGAGTCCCTTTTTACCGCTGTTA
        760       770       780       790       800
CCAATTTTCTTTTGTCTCTGGGTATACATTTGAACCCTAACAAAACAAAG
        810       820       830       840       850
AGATGGGGTTACTCCCTAAATTTTATGGGCTATGTCATTGGATGTTATGG
        860       870       880       890       900
GTCCTTGCCACAAGAACACATCATACATAAAATCAAAGAATGTTTTAGAA
        910       920       930
AACTTCCTGTTAACAGGCCTATTGATTGGAAA
```

Figure 8A

Sample 19  04553852 HBV POL

```
        10         20         30         40         50
PCWWLQFRNSKPCSDYCLSHIVNLLEDWGPCAEYGEHHIRIPRTPSRVTG
        60         70         80         90        100
GVFLVDKNPHNTAESRVVVDFSQFSRGNHRVSWPKFAVPNLQSLTNLLSS
       110        120        130        140        150
DLTWLSLDVTAAFYHIPLHPAAMPHLLVGSSGLSRYVARLSSNSRILNHQ
       160        170        180        190        200
HGNMPNLHDSCSRNLYVSLLLLYQTFGRKLHLYSHPIILGFRKIPMGVGL
       210        220        230        240        250
SPFLLAQFGSAICSVVRRAFPHCLAFIYADDVVLGAKSVQHLESLFTAVT
       260        270        280        290        300
NFLLSLGIHLNPNKTKRWGYSLNFMGYVIGCYGSLPQEHIIHKIKECFRK
       310
LPVNRPIDWK
```

Figure 8B

Sample 19 04553852 HBV HBsAg

```
         10        20        30        40        50
SPAGGSSSGTVNPVPTTASHISSIFSRIGDPALNMENITSGFLGPLLVLQ 60        70        80        90       100
AGFFLLTRILTIPQSLESWWTSLNFLGATTVCLGQNSQSPTSNHSPTSCP 110       120       130       140       150
PT*PGYRWM*LRHFIIFLFILLLCLIFLLVLLDYQGMLPVCPLIPGSSTT 160       170       180       190       200
STGTCRTCTTPAQGTSMYPSCCCTKPSDGNCTCIPIPSSWAFGKFLWEWA 210       220       230       240       250
SARFSWLSLVVPFVQWFVGLSPTVWLSFMRMMWYWGPSLYSILSPFLPLL

260
PIFFCLWVYI
```

Figure 8C

```
Sample 20 05523099 HBV nt
         10        20        30        40        50
   TCCCCTGCTGGTGGCTCCAGTTCCGGAACAGTAAACCCTGTTCCGACTAC
         60        70        80        90       100
   TGCCTCTCACATATCGTCAATCTTCTCGAGGATTGGGGACCCTGCGCTGA
        110       120       130       140       150
   ATATGGAGAACATCACATCAGGATTCCTAGGACCCCTTCTCGTGTTACAG
        160       170       180       190       200
   GCGGGGTTTTCTTGTTGACAAGAATCCTCACAATACCGCAGAGTCTAGA
        210       220       230       240       250
   CTCGTGGTGGACTTCTCTCAATTTTCTAGGGGGAACCACCGTGTGTCTTG
        260       270       280       290       300
   GCCAAAATTCGCAGTCCCCAACCTCCAATCACTCACCAACCTCCTGTCCT
        310       320       330       340       350
   CCGACTTGACCTGGTTATCGCTGGATGTGACTGCGGCATTTTATCATATT
        360       370       380       390       400
   CCTCTTCATCCTGCTGCTATGCCTCATCTTCTTGTTGGTTCTTCTGGACT
        410       420       430       440       450
   ATCAAGGTATGTTGCCCGTTTGTCCTCTAATTCCAGGATCCTCAACCACC
        460       470       480       490       500
   AGCACGGGAACATGCCGAACTTGCACGACTCCTGCTCAAGGAACCTCTAT
        510       520       530       540       550
   GTATCCCTCCTGTTGCTGTACCAAACCTTCGGACGGAAATTGCACCTGTA
        560       570       580       590       600
   TTCCCATCCCATCATCCTGGGCTTTCGGAAAATTCCTATGGGAGTGGGCC
        610       620       630       640       650
   TCAGCCCGTTTCTCCTGGCTCAGTTTGGTAGTGCCATTTGTTCAGTGGTT
        660       670       680       690       700
   CGTAGGGCTTTCCCCCACTGTTTGGCTTTCATTTATGCGGATGATRTGGT
        710       720       730       740       750
   ATTGGGGGCCAAGTCTGTACAGCATCTTGAGTCCCTTTTTACCGCTGTTA
        760       770       780       790       800
   CCAATTTTCTTTTGTCTCTGGGTATACATTTGGYCCCTMACAAAACAAAG
        810       820       830       840       850
   AGATGGGGTTACTCCCTAAATTTTATGGGCTATGTCATTGGATGTTATGG
        860       870       880       890       900
   GTCCTTGCCACAAGAACACATCATACATAAAATCAAAGAATGTTTTAGAA
        910       920       930
   AACTTCCTGTTAACAGGCCTATTGATTGGAAAGT
```

Figure 9A

```
Sample 20  05523099 HBV POL
         10        20        30        40        50
PCWWLQFRNSKPCSDYCLSHIVNLLEDWGPCAEYGEHHIRIPRTPSRVTG 60        70        80        90       100
GVFLVDKNPHNTAESRLVVDFSQFSRGNHRVSWPKFAVPNLQSLTNLLSS 110       120       130       140       150
DLTWLSLDVTAAFYHIPLHPAAMPHLLVGSSGLSRYVARLSSNSRILNHQ 160       170       180       190       200
HGNMPNLHDSCSRNLYVSLLLLYQTFGRKLHLYSHPIILGFRKIPMGVGL 210       220       230       240       250
SPFLLAQFGSAICSVVRRAFPHCLAFIYADDXVLGAKSVQHLESLFTAVT 260       270       280       290       300
NFLLSLGIHLXPXKTKRWGYSLNFMGYVIGCYGSLPQEHIIHKIKECFRK

310
LPVNRPIDWK
```

Figure 9B

Sample 20  05523099 HBV HBsAg

```
         10        20        30        40        50
SPAGGSSSGTVNPVPTTASHISSIFSRIGDPALNMENITSGFLGPLLVLQ 60        70        80        90       100
AGFFLLTRILTIPQSLDSWWTSLNFLGGTTVCLGQNSQSPTSNHSPTSCP 110       120       130       140       150
PT*PGYRWM*LRHFIIFLFILLLCLIFLLVLLDYQGMLPVCPLIPGSSTT 160       170       180       190       200
STGTCRTCTTPAQGTSMYPSCCCTKPSDGNCTCIPIPSSWAFGKFLWEWA 210       220       230       240       250
SARFSWLSLVVPFVQWFVGLSPTVWLSFMRMXWYWGPSLYSILSPFLPLL 260       270
PIFFCLWVYIWXLTKQRDGVTP
```

Figure 9C

```
Sample 21 05538824 HBV nt 10        20        30        40        50
TCCCCTGCTGGTGGCTCCAGTTCCGGAACAGTAAACCGTGTTCCGACTAC
         60        70        80        90       100
TGCCTCTCACATATCGTCAATCTTCTCGAGGATTGGGGACCCTGCGCTGA
        110       120       130       140       150
ATATGGAGAACATCACATCAGGATTCCTAGGACCCCTTCTCGTGTTACAG
        160       170       180       190       200
GCGGGGTTTTCTTGTTGACAAGAATCCTCACAATACCGCAGAGTCTAGA
        210       220       230       240       250
CTCGTGGTGGACTTCTCTCAATTTTCTAGGGGGAACCACCGTGTGTCTTG
        260       270       280       290       300
GCCAAAATTCGCAGTCCCCAACCTCCAATCACTCACCAACCTCCTGTCCT
        310       320       330       340       350
CCGACTTGACCTGGTTATCGCTGGATGTGACTGCGGCATTTTATCATATT
        360       370       380       390       400
CCTCTTCATCCTGCTGCTATGCCTCATCTTCTTGTTGGTTCTTCTGGACT
        410       420       430       440       450
ATCAAGGTATGTTGCCCGTTTGTCCTCTAATTCCAGGATCCTCAACCACC
        460       470       480       490       500
AGCACGGGAACATGCCGAACTTGCACGACTCCTGCTCAAGGAACCTCTAT
        510       520       530       540       550
GTATCCCTCCTGTTGCTGTACCAAACCTTCGGACGGAAATTGCACCTGTA
        560       570       580       590       600
TTCCCATCCCATCATCCTGGGCTTTCGGAAAATTCCTATGGGAGTGGGCC
        610       620       630       640       650
TCAGCCCGTTTCTCCTGGCTCAGTTTGGTAGTGCCATTTGTTCAGTGGTT
        660       670       680       690       700
CGTAGGGCTTTCCCCCACTGTTTGGCTTTCATTTATGCGGATGATRTGGT
        710       720       730       740       750
ATTGGGGGCCAAGTCTGTACAGCATCTTGAGTCCCTTTTTACCGCTGTTA
        760       770       780       790       800
CCAATTTTCTTTTGTCTCTGGGTATACATTTGGYCCCTMACAAAACAAAG
        810       820       830       840       850
AGATGGGGTTACTCCCTAAATTTTATGGGCTATGTCATTGGATGTTATGG
        860       870       880       890
GTCCTTGCCACAAGAACACATCATACATAAAATCAAAGAATG
```

Figure 10A

Sample 21 05538824 HBV POL

```
         10         20         30         40         50
PCWWLQFRNSKPCSDYCLSHIVNLLEDWGPCAEYGEHHIRIPRTPSRVTG 60         70         80         90        100
GVFLVDKNPHNTAESRLVVDFSQFSRGNHRVSWPKFAVPNLQSLTNLLSS 110        120        130        140        150
DLTWLSLDVTAAFYHIPLHPAAMPHLLVGSSGLSRYVARLSSNSRILNHQ 160        170        180        190        200
HGNMPNLHDSCSRNLYVSLLLLYQTFGRKLHLYSHPIILGFRKIPMGVGL 210        220        230        240        250
SPFLLAQFGSAICSVVRRAFPHCLAFIYADDXVLGAKSVQHLESLFTAVT 260        270        280        290
NFLLSLGIHLXPXKTKRWGYSLNFMGYVIGCYGSLPQEHIIHKIKE
```

Figure 10B

Sample 21 05538824 HBV HBsAg

```
        10        20        30        40        50
SPAGGSSSGTVNRVPTTASHISSIFSRIGDPALNMENITSGFLGPLLVLQ 60        70        80        90       100
AGFFLLTRILTIPQSLDSWWTSLNFLGGTTVCLGQNSQSPTSNHSPTSCP 110       120       130       140       150
PT*PGYRWM*LRHFIIFLFILLLCLIFLLVLLDYQGMLPVCPLIPGSSTT 160       170       180       190       200
STGTCRTCTTPAQGTSMYPSCCCTKPSDGNCTCIPIPSSWAFGKFLWEWA 210       220       230       240       250
SARFSWLSLVVPFVQWFVGLSPTVWLSFMRMXWYWGPSLYSILSPFLPLL 260       270
PIFFCLWVYIWXLTKQRDGVTP*

ANTIVIRAL RESISTANCE MUTANTS AND APPLICATIONS THEREOF

This application is U.S. National Phase of International Application PCT/AU2006/001563, filed Oct. 20, 2006 designating the U.S., and published in English as WO 2007/045045 on Apr. 26, 2007, which claims priority to Australian Patent Application No. 2005905862 filed Oct. 21, 2005.

BACKGROUND OF THE INVENTION

Field of the Invention

The present invention relates generally to viral variants exhibiting reduced sensitivity to agents such as nucleoside or nucleotide analogs or other DNA polymerase antagonists and/or reduced interactivity with immunological reagents. More particularly, the present invention is directed to hepatitis B virus (HBV) variants exhibiting complete or partial resistance to nucleoside or nucleotide analogs or other DNA polymerase antagonists and/or reduced interactivity with antibodies to viral surface components including reduced sensitivity to these antibodies. The present invention further contemplates assays for detecting such viral variants, which assays are useful in monitoring anti-viral therapeutic regimens and in developing new or modified vaccines directed against viral agents and in particular HBV variants. The present invention also contemplates the use of the viral variants to screen for and/or develop or design agents capable of inhibiting infection, replication and/or release of the virus.

Description of the Prior Art

Bibliographic details of the publications referred to in this specification are also collected at the end of the description.

The reference to any prior art in this specification is not, and should not be taken as, an acknowledgment or any form of suggestion that that prior art forms part of the common general knowledge in any country.

Hepatitis B virus (HBV) can cause debilitating disease conditions and can lead to acute liver failure. HBV is a DNA virus which replicates via an RNA intermediate and utilizes reverse transcription in its replication strategy (Summers and Mason, *Cell* 29: 403-415, 1982). The HBV genome is of a complex nature having a partially double-stranded DNA structure with overlapping open reading frames encoding surface, core, polymerase and X genes. The complex nature of the HBV genome is represented in FIG. 1. The polymerase consists of four functional regions, the terminal protein (TP), spacer, reverse transcriptase (rt) and ribonuclease (RNAse).

The polymerase gene of HBV overlaps the envelope gene, mutations in the catalytic domain of the polymerase gene can also affect the nucleotide and the deduced amino acid sequence of the envelope protein and vice versa. In particular, the genetic sequence for the neutralization domain of HBV known as the 'a' determinant, which is found within the HBsAg and located between amino acids 99 and 169, actually overlaps the major catalytic regions of the viral polymerase protein and in particular domains A and B.

The presence of an HBV DNA polymerase has led to the proposition that nucleoside or nucleotide analogs could act as effective anti-viral agents. Examples of nucleoside or nucleotide analogs currently being tested are penciclovir and its oral form (FCV) [Vere Hodge, *Antiviral Chem Chemother* 4: 67-84, 1993; Boyd et al, *Antiviral Chem Chemother.* 32: 358-363, 1987; Kruger et al, *Hepatology* 22: 219A, 1994; Main et al, *J. Viral Hepatitis* 3: 211-215, 1996], Lamivudine [(−)-β-2'-deoxy-3'-thiacytidine]; (3TC or LMV) [Severini et al, *Antimicrobial Agents Chemother.* 39: 430-435, 1995; Dienstag et al, *New England J Med* 333: 1657-1661, 1995]. New nucleoside or nucleotide analogs which have already progressed to clinical trials include the pyrimidines Emtricitabine, ((−)-β-L-2'-3'-dideoxy-5-fluoro-3'-thiacydidine; FTC), the 5-fluoro derivative of 3TC, and Clevudine (1-(2-fluoro-5-methyl-β-L-arabino-furanosyl) uracil; L-FMAU), a thymidine analog. Like 3TC, these are pyrimidine derivatives with an unnatural "L"-configuration. Several purine derivatives have also progressed to clinical trials; they include Entecavir (BMS-200, 475; ETV), a carbocyclic deoxyguanosine analog, diaminopurine dioxolane (DAPD), an oral pro-drug for dioxolane guanine ((−)-β-D-2-aminopurine dioxolane; DXG) and Adefovir dipivoxil, an oral prodrug for the acyclic deoxyadenosine monophosphate nucleoside or nucleotide analog Adefovir (9-[phosphonyl-methoxyethyl]-adenine; PMEA). Other drugs in pre-clinical and clinical trials include FLG [Medivir], ACH-126,443 (L-d4C) [Archillion Pharmaceuticals], ICN 2001-3 (ICN) and Racivir (RCV) [Pharmassett].

Whilst these agents are highly effective in inhibiting HBV DNA synthesis, there is the potential for resistant mutants of HBV to emerge during long term antiviral chemotherapy. In patients on prolonged LMV therapy, key resistance mutations are selected in the rt domain within the polymerase at rtM204I/V+/−rtL180M as well as other mutations. The nomenclature used for the polymerase mutations is in accordance with that proposed by Stuyver et al, 2001, supra. LMV is a nucleoside or anucleotide analog that has been approved for use against chronic HBV infection. LMV is a particularly potent inhibitor of HBV replication and reduces HBV DNA titres in the sera of chronically infected patients after orthotopic liver transplantation (OLT) by inhibiting viral DNA synthesis. LMV monotherapy seems unlikely to be able to control HBV replication in the longer term. This is because emergence of LMV-resistant strains of HBV seems almost inevitable during monotherapy.

Adefovir dipivoxil (ADV: formerly, bis-pom PMEA) is an orally available prodrug of the acyclic deoxyadenosine monophosphate analog adefovir (formerly, PMEA) (FIG. 2). ADV is also a potent inhibitor of HBV replication and has recently been given FDA approval for use against chronic HBV infection. Adefovir dipivoxil differs from other agents in this class in that it is a nucleotide (vs. nucleoside) analog and as such bypasses the first phosphorylation reaction during drug activation. This step is often rate-limiting. Adefovir dipivoxil has demonstrated clinical activity against both wild-type and lamivudine-resistant strains of HBV and is currently in phase III clinical Testing (Gilson et al, *J Viral Hepat* 6: 387-395, 1999; Perrillo et al, *Hepatology* 32: 129-134, 2000; Peters et al, *Transplantation* 68: 1912-1914, 1999; Benhainou et al, *Lancet* 358: 718-723, 2001). During phase II studies a 30 mg daily dose of adefovir dipivoxil resulted in a mean 4 $\log_{10}$ decrease in viremia over 12 weeks (Heathcote et al, *Hepatology* 28: A620, 1998). ADV is a substituted acyclic nucleoside phosphonate. This class of compounds also includes tenofovir disoproxil fumarate (also referred to as tenofovir DF, or tenofovir, or (TFV) or 9-R-(2-phosphonomethoxypropyl)adenine (PMPA) and is marketed as Viread by Gilead sciences).

TFV has antiviral activity against both HBV and HIV (Ying et al, *J Viral Hepat.* 7(2): 161-165, 2000; Ying et al, *J Viral Hepat.* 7(1): 79-83, 2000, 2000; Suo et al, *J Biol Chem.* 273(42): 27250-27258. 1998).

FTC has activity against HBV and HIV (Frick et al, *Antimicrob Agents Chemother* 37: 2285-2292, 1993).

Nucleoside or nucleotide analog therapy may be administered as monotherapy or combination therapy where two or more nucleoside or nucleotide analogs may be administered. The nucleoside or nucleotide analogs may also be administered in combination with other antiviral agents such as interferon or hepatitis B immunoglobulin (HBIG).

There is a need to monitor for the emergence of resistant strains of HBV and to develop diagnostic protocols to detect these resistant viruses and/or to use them to screen for and/or develop or design agents having properties making them useful as anti-viral agents. Defective forms of these resistant strains or antigenic components therefrom are also proposed to be useful in the development of therapeutic vaccine compositions as are antibodies directed to viral surface components.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

Specific mutations in an amino acid sequence are represented herein as "$Xaa_1nXaa_2$" where $Xaa_1$ is the original amino acid residue before mutation, n is the residue number and $Xaa_2$ is the mutant amino acid. The abbreviation "Xaa" may be the three letter or single letter (i.e. "X") code. An "rt" before "$Xaa_1nXaa_2$" means "reverse transcriptase". An "s" means an envelope gene. The amino acid residues for HBV DNA polymerase are numbered with the residue methionine in the motif Tyr Met Asp Asp (YMDD) being residue number 204 (Stuyver et al, *Hepatology* 33: 751-757, 2001). The amino acid residues for hepatitis B virus surface antigen are number according to Norder et al. (*J. Gen. Virol.* 74: 341-1348, 1993). Both single and three letter abbreviations are used to define amino acid residues and these are summarized in Table 2.

HBV variants are identified in a patient with chronic HBV infection and treated with ADV. This patient had previously been on a number of antiviral agents sequentially and had previously selected ETV and LMV resistance HBV variants (refer to Tenney et al, *Antimicrob Agents Chemother* 48(9): 3498-507, 2004 and International Patent Application PCT/AU03/00111 (WO 03/066,841)). In addition, the patient retained mutations associated with ETV resistance while on ADV treatment. In accordance with the present invention, variants of HBV are identified following and ADV treatment, with mutations in the HBV DNA polymerase gene which reduce the sensitivity of HBV to nucleoside or nucleotide analogues. Corresponding mutations in the surface antigen also occur. The identification of these HBV variants is important for the development of assays to monitor ADV and/or resistance to other nucleoside or nucleotide analogues or other DNA polymerase antagonists and to screen for agents which are useful as alternative therapeutic agents. Importantly, this patient has selected new mutations at codons 236 and 85 (ie., rtN236A/V/S and rtS85T) and also a new mutation at codon 204 (namely rtM204A). Previously, the mutation at rtM204I/V has been reported to be associated with LMV resistance. Thus, the selection of this new mutation has implications for multi-drug resistance.

Accordingly, the present invention provides HBV variants which are contemplated which are resistant to, or which exhibit reduced sensitivity to, ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. The variants comprise mutations in the HBV DNA polymerase and the genetic sequence encoding same. Corresponding mutations in the surface antigen also occur. The identification of these HBV variants is important for the development of assays to monitor ADV, LMV, FTC, TFV and/or ETV resistance and/or resistance to other nucleoside or nucleotide analogs or other anti-HBV agents or combinations thereof and to screen for agents which are useful as alternative therapeutic agents.

Reference herein to "anti-HBV agents" includes nucleoside and nucleotide analogs as well as immunological reagents (e.g. antibodies to HBV surface components) and chemical, proteinaceous and nucleic acid agents which inhibit or otherwise interfere with viral replication, maintenance, infection, assembly or release. The term "anti-HBV agents" also include non-nucleoside or non-nucleotide DNA polymerase antagonists.

The detection of such HBV variants is particularly important in the management of therapeutic protocols including the selection of appropriate agents for treating HBV infection. The method of this aspect of the present invention is predicated in part on monitoring the development in a subject of an increased HBV load in the presence of a nucleoside or nucleotide analog or other anti-HBV agents or combinations thereof. The clinician is then able to modify an existing treatment protocol or select an appropriate treatment protocol accordingly.

Accordingly, one aspect of the present invention is directed to an isolated HBV variant wherein said variant comprises a nucleotide mutation in a gene encoding a DNA polymerase resulting in at least one amino acid addition, substitution and/or deletion to said DNA polymerase and wherein said variant exhibits decreased sensitivity to one or more nucleoside or nucleotide analogs selected from the list consisting of ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. The variant HBV comprises a mutation in an overlapping open reading frame in its genome in a region defined by one or more of domains F and G and domain A through to E of HBV DNA polymerase.

Another aspect of the present invention provides an isolated HBV variant comprising a nucleotide mutation in the S gene resulting in at least one amino acid addition, substitution and/or deletion to the surface antigen and which exhibits decreased sensitivity to one or more nucleoside or nucleotide analogs selected from the list consisting of ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

Particular mutants in the rt region contemplated by the present invention include, but are not limited to, rtS78T, rtS85T, rtT128N, rtT184G, rtS202I, rtV207M, rtM204A, rtN238H and/or rtN236A/V/S Even more particular mutants are rtS85T, rtM204A and/or rtN236A/V/S.

Still a most particular mutant is rtS85T and which optionally also has mutation rtM204A.

Particular mutations in the S gene include, in one embodiment encode sC69stop, sC76stop, sR79H, sP120T, sL176V, sV194F, sI195M and/or sW196R.

Hence, the present invention provides an isolated Hepatitis B virus (HBV) variant wherein said variant comprises a nucleotide mutation in a gene encoding a DNA polymerase resulting in amino acid mutation rtS85T in said DNA polymerase wherein said variant exhibits decreased sensitivity to ADV. In one embodiment, the HBV variant further has an rtM204A mutation as well as any or all of the above-mentioned mutations. The HBV variant may also be resistant to or exhibit reduced sensitivity to one or more of LMV, ETV, FTC and/or TFV.

The present invention further contemplates a method for determining the potential for an HBV to exhibit reduced sensitivity to ADV, and/or optionally other nucleoside or nucleotide analogs or other anti-HBV agents or combinations thereof by isolating DNA or corresponding mRNA from the HBV and screening for a mutation in the nucleotide sequence encoding HBV DNA polymerase resulting in at least one amino acid substitution, deletion and/or addition in any one or more of domains F and G and domains A through to E or a region proximal thereto of the DNA polymerase and associated with resistance or decreased sensitivity to ADV and/or optionally other nucleoside or nucleotide analogs or other anti-HBV agents or combinations thereof.

The present invention further contemplates a method for determining the potential for an HBV to exhibit reduced sensitivity to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof by isolating DNA or corresponding mRNA from the HBV and screening for a mutation in the nucleotide sequence encoding HBV DNA polymerase resulting in at least one amino acid substitution, deletion and/or addition in any one or more of domains F and G and domains A through to E or a region proximal thereto of the DNA polymerase and associated with resistance or decreased sensitivity to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

The presence of such a mutation is an indication of the likelihood of resistance to ADV and/or optionally other nucleoside or nucleotide analogs or other anti-HBV agents or combinations thereof. As indicated above, an example of an anti-HBV agent is a DNA polymerase antagonist.

The presence of such a mutation is an indication of the likelihood of resistance to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

Hence, the present invention contemplates a method for determining the potential for an HBV to exhibit reduced sensitivity to ADV said method comprising isolating DNA or corresponding mRNA from the HBV and screening for the presence of a genomic mutation resulting in amino acid mutation rtS85T in its DNA polymerase wherein the presence of this substitution is indicative of an HBV with reduced sensitivity to ADV.

As indicated above, the HBV variant may also have an rtM204A mutation in its DNA polymerase.

The present invention also provides a composition comprising a variant HBV resistant to ADV, and/or optionally other nucleoside or nucleotide analogs or other anti-HBV agents or combinations thereof or an HBV surface antigen from the variant HBV or a recombinant or derivative form thereof or its chemical equivalent and one or more pharmaceutically acceptable carriers and/or diluents.

The present invention also provides a composition comprising a variant HBV resistant to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof or an HBV surface antigen from the variant HBV or a recombinant or derivative form thereof or its chemical equivalent and one or more pharmaceutically acceptable carriers and/or diluents.

The present invention is also directed to a composition comprising a variant HBV exhibiting reduced sensitivity to ADV and having amino acid mutation rtS85T in its DNA polymerase and one or more pharmaceutically acceptable carriers and/or diluents.

Yet another aspect of the present invention provides a use of the aforementioned composition or a variant HBV comprising a nucleotide mutation in a gene encoding a DNA polymerase resulting in at least one amino acid addition, substitution and/or deletion to the DNA polymerase and a decreased sensitivity to ADV, and/or optionally other nucleoside or nucleotide analogs or other anti-HBV agents or combinations thereof in the manufacture of a medicament for the treatment and/or prophylaxis of hepatitis B virus infection.

Yet another aspect of the present invention provides a use of the aforementioned composition or a variant HBV comprising a nucleotide mutation in a gene encoding a DNA polymerase resulting in at least one amino acid addition, substitution and/or deletion to the DNA polymerase and a decreased sensitivity to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof in the manufacture of a medicament for the treatment and/or prophylaxis of hepatitis B virus infection.

The present invention is also directed to the use of a variant HBV exhibiting reduced sensitivity to ADV and having amino acid substitution rtS85T in its DNA polymerase in the manufacture of a medicament for the treatment or prophylaxis of HBV infection.

The present invention also contemplates a method for determining whether an HBV strain exhibits reduced sensitivity to a nucleoside or nucleotide analog or other anti-HBV agents or by isolating DNA or corresponding mRNA from the HBV and screening for a mutation in the nucleotide sequence encoding the DNA polymerase wherein the presence of the following mutations in the rt region: rtS78T, rtS85T, rtT128N, rtT184G, rtS202I, rtV207M, rtM204A, rtN236A/V/S, rtN238H or a combination thereof or an equivalent mutation or combinations thereof or an equivalent one or more other mutation is indicative of a variant which exhibits a decreased sensitivity to ADV and/or optionally other nucleoside or nucleotide analogs or other anti-HBV agents or combinations thereof.

The present invention also contemplates a method for determining whether an HBV strain exhibits reduced sensitivity to a nucleoside or nucleotide analog or other anti-HBV agents or by isolating DNA or corresponding mRNA from the HBV and screening for a mutation in the nucleotide sequence encoding the DNA polymerase wherein the presence of the following mutations in the rt region: rtS78T, rtS85T, rtT128N, rtT184G, rtS202I, rtV207M, rtM204A, rtN236A/V/S, rtN238H or a combination thereof or an equivalent mutation or combinations thereof or an equivalent one or more other mutation is indicative of a variant which exhibits a decreased sensitivity to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

Still a further methodology comprises screening for a mutation in the nucleotide sequence encoding the envelope genes (s) wherein the presence of the following mutations in the s gene: in one embodiment include sC69stop, sC76stop, sR79H, sP120T, sL176V, sV194F, sI195M, sW196R, or a combination thereof or an equivalent mutation or combinations thereof or an equivalent one or more other mutation is indicative of a variant which exhibits a decreased sensitivity to ADV and/or optionally other nucleoside or nucleotide analogs or other anti-HBV agents or combinations thereof, and/or optionally other nucleoside or nucleotide analogs or other anti-HBV agents or combination thereof.

Still a further methodology comprises screening for a mutation in the nucleotide sequence encoding the envelope genes (s) wherein the presence of the following mutations in the s gene: in one embodiment include sC69stop, sC76stop, sR79H, sP120T, sL176V, sV194F, sI195M, sW196R, or a combination thereof or an equivalent mutation or combinations thereof or an equivalent one or more other mutation is indicative of a variant which exhibits a decreased sensitivity to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof, and/or optionally other nucleoside or nucleotide analogs or other anti-HBV agents or combination thereof.

Preferably, the variants are in an isolated form such that they have undergone at least one purification step away from naturally occurring body fluid. Alternatively, the variants may be maintained in isolated body fluid or may be in DNA form. The present invention also contemplates infectious molecular clones comprising the genome or parts thereof from a variant HBV. The detection of HBV or its components in cells, cell lysates, cultured supernatant fluid and bodily fluid may be by any convenient means including any nucleic acid-based detection means, for example, by nucleic acid hybridization techniques or via one or more polymerase chain reactions (PCRs). The term "bodily fluid" includes any fluid derived from the blood, lymph, tissue or organ systems including serum, whole blood, biopsy and biopsy fluid, organ explants and organ suspension such as liver suspensions.

Another aspect of the present invention is directed to a variant HBV comprising a surface antigen having an amino acid sequence with a single or multiple amino acid substitution, addition and/or deletion or a truncation compared to a surface antigen from a reference or wild type HBV and wherein an antibody generated to the reference or wild type surface antigen exhibits an altered immunological profile relative to the HBV variant. One altered profile includes a reduced capacity for neutralizing the HBV. More particularly, the surface antigen of the variant HBV exhibits an altered immunological profile compared to a pre-treatment HBV where the variant HBV is selected for by a nucleoside or nucleotide analog or other anti-HBV agents of the HBV DNA polymerase. The variant HBV of this aspect of the invention may also comprise a nucleotide sequence comprising a single or multiple nucleotide substitution, addition and/or deletion compared to a pre-treatment HBV.

The present invention further contemplates a method for detecting a variant HBV exhibiting an altered immunological profile said method comprising isolating an HBV from a subject exposed to a nucleoside or nucleotide analog or combination of analogs ADV and/or optionally other nucleoside or nucleotide analogs or other anti-HBV agents or combinations thereof, and then contacting said HBV with a panel of one or more antibodies to a surface antigen and screening for any change in binding affinity or binding spectrum.

The present invention further contemplates a method for detecting a variant HBV exhibiting an altered immunological profile said method comprising isolating an HBV from a subject exposed to a nucleoside or nucleotide analog or combination of analogs selected from the listed consisting of ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof, and then contacting said HBV with a panel of one or more antibodies to a surface antigen and screening for any change in binding affinity or binding spectrum.

In addition, the present invention provides a method for detecting a variant HBV exhibiting an altered immunological profile said method comprising isolating a serum sample from a subject exposed to a nucleoside or nucleotide analog ADV and/or optionally other nucleoside or nucleotide analogs or other anti-HBV agents or combinations thereof, and then contacting the serum with a panel of HBV surface antigens or antibody-binding fragments thereof and screening for any change in binding affinity or binding spectrum.

Furthermore, the present invention provides a method for detecting a variant HBV exhibiting an altered immunological profile said method comprising isolating a serum sample from a subject exposed to a nucleoside or nucleotide analog selected from the listed consisting of ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof, and then contacting the serum with a panel of HBV surface antigens or antibody-binding fragments thereof and screening for any change in binding affinity or binding spectrum.

The present invention extends to an isolated HBsAg or a recombinant form thereof or derivative or chemical equivalent thereof corresponding to the variant HBV. Generally, the HBsAg or its recombinant or derivative form or its chemical equivalent comprises an amino acid sequence with a single or multiple amino acid substitution, addition and/or deletion or a truncation compared to an HBsAg from a reference HBV and wherein an antibody directed to a reference HBV exhibits an altered immunological profile to an HBV carrying said variant HBsAg. In one embodiment, the altered immunological profile comprises a reduction in the ability to neutralize the variant HBV.

Hence, the present invention provides an isolated HBV surface antigen comprising a mutation selected from the list consisting of sC69STOP, sC76STOP, sR79H, sP120T, sL176V, sV194F, sT195M and sW196R.

Another aspect of the present invention contemplates a method for detecting an agent which exhibits inhibitory activity to an HBV by generating a genetic construct comprising a replication competent-effective amount of the genome from the HBV contained in a plasmid vector and then transfecting said cells with said construct, contacting the cells, before, during and/or after transfection, with the agent to be tested, culturing the cells for a time and under conditions sufficient for the HBV to replicate, express genetic sequences and/or assemble and/or release virus or virus-like particles if resistant to said agents; and the subjecting the cells, cell lysates or culture supernatant fluid to viral- or viral-component-detection means to determine whether or not the virus has replicated, expressed genetic material and/or assembled and/or been released in the presence of the agent. In a preferred embodiment, the plasmid vector in a baculovirus vector and the method comprises generating a genetic construct comprising a replication competent-effective amount of the genome from the HBV contained in or fused to an amount of a baculovirus genome effective to infect cells and then infecting said cells with said construct, contacting the cells, before, during and/or after infection, with the agent to be tested, culturing the cells for a time and under conditions sufficient for the HBV to replicate, express genetic sequences and/or assemble and/or release virus or virus-like particles if resistant to said agent and then subjecting the cells, cell lysates or culture supernatant fluid to viral- or viral-component-detection means to determine whether or not the virus has replicated, expressed genetic material and/or assembled and/or been released in the presence of the agent.

In connection with these methods, the plasmid vector may include genes encoding part or all of other viral vectors such as baculovirus vectors or adenovirus vectors (see Ren and Nassal, *J. Virol.* 75(3): 1104-1116, 2001).

In an alternative embodiment, the method comprises generating a continuous cell line comprising an infectious copy of the genome of the HBV in a replication competent effective amount such that said infectious HBV genome is stably integrated into said continuous cell line such as but not limited to the 2.2.15 or AD cell line, contacting the cells with the agent to be tested, culturing the cells for a time and under conditions sufficient for the HBV to replicate, express genetic sequences and/or assemble and/or release virus or virus-like particles if resistant to the agent and then subjecting the cells, cell lysates or culture supernatant fluid to viral- or viral-component-detection means to determine whether or not the virus has replicated, expressed genetic material and/or assembled and/or been released in the presence of the agent.

In an alternative embodiment, the present invention also contemplates a method for detecting an agent which exhibits inhibitory activity to an HBV polymerase in an in vitro polymerase assay. The HBV polymerase activity can be examined using established assays (Gaillard et al, *Antimicrob Agents Chemother.* 46(4): 1005-1013, 2002; Xiong et al, *Hepatology.* 28(6): 1669-73, 1998). The HBV polymerase may be a wild-type or reference HBV polymerase or mutant HBV polymerase.

The identification of viral variants enables the production of vaccines comprising particular recombinant viral components such as polymerases or envelope genes PreS1, PreS2, S encoding for L, M, S proteins as well as therapeutic vaccines comprising defective HBV variants. Rational drug design may also be employed to identify or generate therapeutic molecules capable of interacting with a polymerase or envelope genes PreS1, PreS2, S encoding for L, M, S proteins or other component of the HBV. Such drugs may also have diagnostic potential. In addition, defective HBV variants may also be used as therapeutic compositions to generate an immune response against the same, similar or homologous viruses. Alternatively, antibodies generated to the HBV variants or surface components thereof may be used in passive immunization of subjects against infection by HBV variants or similar or homologous viruses. Furthermore, agents such as nucleoside or nucleotide analogs, RNAi or siRNA molecules (both DNA-derived or synthetic), antisense or sense oligonucleotides, chemical or proteinaceous molecules having an ability to down-regulate the activity of a component of HBV and inhibit replication, maintenance, infection, assembly or release are contemplated by the present invention.

In one embodiment, the present invention provides a composition comprising a variant HBV exhibiting reduced sensitivity to ADV and having amino acid mutation rtS85T in its DNA polymerase and one or more pharmaceutically acceptable carriers and/or diluents.

The present invention further contemplates the use of a variant HBV exhibiting reduced sensitivity to ADV and having amino acid substitution rtS85T in its DNA polymerase in the manufacture of a medicament for the treatment or prophylaxis of HBV infection.

A computer product for assessing the likely usefulness of an HBV variant or biological sample comprising same for determining an appropriate therapeutic protocol in a subject, said product comprising:

(I) code that receives an input code for at least two features associated with said HBV or biological sample comprising same, wherein said features are selected from:
  (a) a mutation in the HBV genome resulting in amino acid mutation rtS85T in its DNA polymerase;
  (b) a mutation in the HBV genome resulting in amino acid mutation rtM204I/V in its DNA polymerase;
  (c) a mutation in the HBV genome resulting in amino acid mutation rtS78T, rtT128N, rtT184G, rtS202I, rtV207M, rtN238, rtI266, rtN236A/V/S, rtN238H and rtM204A in its DNA polymerase;
  (d) a mutation in the HBV genome resulting in amino acid mutation rtM204A, rtM204I/V and rtN236A/V/S in its DNA polymerase;
  (e) a mutation in the HBV genome resulting in amino acid mutation sC69STOP, sC76STOP, sR79H, sP120T, sL176V, sV194F, sT195M in sW196R and its surface antigen;
(II) code that records said input code; and
(III) a computer readable medium that stores the codes.

A summary of the abbreviations used throughout the subject specification are provided in Table 3.

A summary of sequence identifiers used throughout the subject specification is provided in Table 1.

TABLE 1

Summary of sequence identifiers

| SEQUENCE ID NO: | DESCRIPTION |
|---|---|
| 1 | PCR primer |
| 2 | PCR primer |
| 3 | PCR primer |
| 4 | PCR primer |
| 5 | PCR primer |
| 6 | Nucleotide sequence of catalytic region of polymerase from resistant HBV Patient A: Sample 14 |
| 7 | Deduced amino acid sequence of catalytic region of polymerase resistant HBV Patient A: Sample 14 |
| 8 | Deduced amino acid sequence of envelope gene from resistant HBV from Patient A: Sample 14 |
| 9 | Nucleotide sequence of catalytic region of polymerase from resistant HBV Patient A: Sample 15 |
| 10 | Deduced amino acid sequence of catalytic region of polymerase resistant HBV Patient A: Sample 15 |
| 11 | Deduced amino acid sequence of envelope gene from resistant HBV from Patient A: Sample 15 |
| 12 | Nucleotide sequence of catalytic region of polymerase from resistant HBV Patient A: Sample 16 |
| 13 | Deduced amino acid sequence of catalytic region of polymerase resistant HBV Patient A: Sample 16 |
| 14 | Deduced amino acid sequence of envelope gene from resistant HBV from Patient A: Sample 16 |

TABLE 1-continued

Summary of sequence identifiers

| SEQUENCE ID NO: | DESCRIPTION |
|---|---|
| 15 | Nucleotide sequence of catalytic region of polymerase from resistant HBV Patient A: Sample 17 |
| 16 | Deduced amino acid sequence of catalytic region of polymerase resistant HBV Patient A: Sample 17 |
| 17 | Deduced amino acid sequence of envelope gene from resistant HBV from Patient A: Sample 17 |
| 18 | Nucleotide sequence of catalytic region of polymerase from resistant HBV Patient A: Sample 19 |
| 19 | Deduced amino acid sequence of catalytic region of polymerase resistant HBV Patient A: Sample 19 |
| 20 | Deduced amino acid sequence of envelope gene from resistant HBV from Patient A: Sample 19 |
| 21 | Nucleotide sequence of catalytic region of polymerase from resistant HBV Patient A: Sample 20 |
| 22 | Deduced amino acid sequence of catalytic region of polymerase resistant HBV Patient A: Sample 20 |
| 23 | Deduced amino acid sequence of envelope gene from resistant HBV from Patient A: Sample 20 |
| 24 | Nucleotide sequence of catalytic region of polymerase from resistant HBV Patient A: Sample 21 |
| 25 | Deduced amino acid sequence of catalytic region of polymerase resistant HBV Patient A: Sample 21 |
| 26 | Deduced amino acid sequence of envelope gene from resistant HBV from Patient A: Sample 21 |

TABLE 2

Single and three letter amino acid abbreviations

| Amino Acid | Three-letter Abbreviation | One-letter symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Stop | | * |
| Any residue | Xaa | X |

TABLE 3

Abbreviations

| ABBREVIATION | DESCRIPTION |
|---|---|
| 3TC | (LMV); (−)-β-2′-deoxy-3′-thiacytidine |
| ADV | adefovir dipivoxil |
| DAPD | diaminopurine dioxalone |
| DXG | dioxolane guanine |
| ETV | entecavir |
| FAM | famciclovir |
| FCV | famciclovir |
| FTC | emtricitabine |
| HBIG | hepatitis B immunoglobulin |
| HBsAg | hepatitis B surface antigen |
| HBV | hepatitis B virus |
| LMV | lamividuine |
| PMEA | 9-[phosphonyl-methoxyethyl]-adenine; adefovir |
| PMPA | 9-R-(2-phosphonomethoxypropyl)adenine |
| RNase | ribonuclease |
| rt ("rt" before "Xaa$_1$nXaa$_2$" means reverse transcriptase) | reverse transcriptase |
| s (as used in a mutation, e.g. sF134V) | envelope gene, S |
| TFV | tenofovir disoproxil fumarate |
| HBsAg | Hepatitis B surface antigen |
| YMDD | Tyr Met Asp Asp-a motif in the polymerase protein; where the Met residue is designated residue number 204 of the reverse transcriptase |

BRIEF DESCRIPTION OF THE FIGURES

FIG. 4A is a representation of the HBV nucleotide sequence (SEQ ID NO: 6) encoding the catalytic region of the polymerase gene in sequential samples from Patient A during ADV treatment (sample 14) [time point 1] (refer to FIG. 11).

FIG. 4B is a representation of the deduced amino acid sequence (SEQ ID NO: 7) of the catalytic region of the polymerase gene in sequential samples from Patient A during ADV therapy (sample 14) [time point 1] (refer to FIG. 11).

FIG. 4C is a representation of the deduced amino acid sequence (SEQ ID NO: 8) of the envelope gene in sequential samples from Patient A during ADV therapy (sample 14) [time point 1] (refer to FIG. 11).

FIG. 5A is a representation of the HBV nucleotide sequence (SEQ ID NO: 9) encoding the catalytic region of the polymerase gene in sequential samples from Patient A during ADV treatment (sample 15) [time point 2] (refer to FIG. 11).

FIG. 5B is a representation of the deduced amino acid sequence (SEQ ID NO: 10) of the catalytic region of the polymerase gene in sequential samples from Patient A during ADV therapy (sample 15) [time point 2] (refer to FIG. 11).

FIG. 5C is a representation of the deduced amino acid sequence (SEQ ID NO: 11) of the envelope gene in sequential samples from Patient A during ADV therapy (sample 15) [time point 2] (refer to FIG. 11).

FIG. 6A is a representation of the HBV nucleotide sequence (SEQ ID NO: 12) encoding the catalytic region of the polymerase gene in sequential samples from Patient A during ADV treatment (sample 16) [time point 3] (refer to FIG. 11).

FIG. 6B is a representation of the deduced amino acid sequence (SEQ ID NO: 13) of the catalytic region of the polymerase gene in sequential samples from Patient A during ADV therapy (sample 16) [time point 3] (refer to FIG. 11).

FIG. 6C is a representation of the deduced amino acid sequence (SEQ ID NO: 14) of the envelope gene in sequential samples from Patient A during ADV therapy (sample 16) [time point 3] (refer to FIG. 11).

FIG. 7A is a representation of the HBV nucleotide sequence (SEQ ID NO: 15) encoding the catalytic region of the polymerase gene in sequential samples from Patient A during ADV treatment (sample 17) [time point 4] (refer to FIG. 11).

FIG. 7B is a representation of the deduced amino acid sequence (SEQ ID NO: 16) of the catalytic region of the polymerase gene in sequential samples from Patient A during ADV therapy (sample 17) [time point 4] (refer to FIG. 11).

FIG. 7C is a representation of the deduced amino acid sequence (SEQ ID NO: 17) of the envelope gene in sequential samples from Patient A during ADV therapy (sample 17) [time point 4] (refer to FIG. 11).

FIG. 8A is a representation of the HBV nucleotide sequence (SEQ ID NO: 18) encoding the catalytic region of the polymerase gene in sequential samples from Patient A during ADV treatment (sample 19) [time point 5] (refer to FIG. 11).

FIG. 8B is a representation of the deduced amino acid sequence (SEQ ID NO: 19) of the catalytic region of the polymerase gene in sequential samples from Patient A during ADV therapy (sample 19) [time point 5] (refer to FIG. 11).

FIG. 8C is a representation of the deduced amino acid sequence (SEQ ID NO: 20) of the envelope gene in sequential samples from Patient A during ADV therapy (sample 19) [time point 5] (refer to FIG. 11).

FIG. 9A is a representation of the HBV nucleotide sequence (SEQ ID NO: 21) encoding the catalytic region of the polymerase gene in sequential samples from Patient A during ADV treatment (sample 20) [time point 6] (refer to FIG. 11).

FIG. 9B is a representation of the deduced amino acid sequence (SEQ ID NO: 22) of the catalytic region of the polymerase gene in sequential samples from Patient A during ADV therapy (sample 20) [time point 6] (refer to FIG. 11).

FIG. 9C is a representation of the deduced amino acid sequence (SEQ ID NO: 23) of the envelope gene in sequential samples from Patient A during ADV therapy (sample 20) [time point 6] (refer to FIG. 11).

FIG. 10A is a representation of the HBV nucleotide sequence (SEQ ID NO: 24) encoding the catalytic region of the polymerase gene in sequential samples from Patient A during ADV treatment (sample 21) [time point 7] (refer to FIG. 11).

FIG. 10B is a representation of the deduced amino acid sequence (SEQ ID NO: 25) of the catalytic region of the polymerase gene in sequential samples from Patient A during ADV therapy (sample 21) [time point 7] (refer to FIG. 11).

FIG. 10C is a representation of the deduced amino acid sequence (SEQ ID NO: 26) of the envelope gene in sequential samples from Patient A during ADV therapy (sample 21) [time point 7] (refer to FIG. 11).

DETAILED DESCRIPTION OF THE INVENTION

Figure 1:
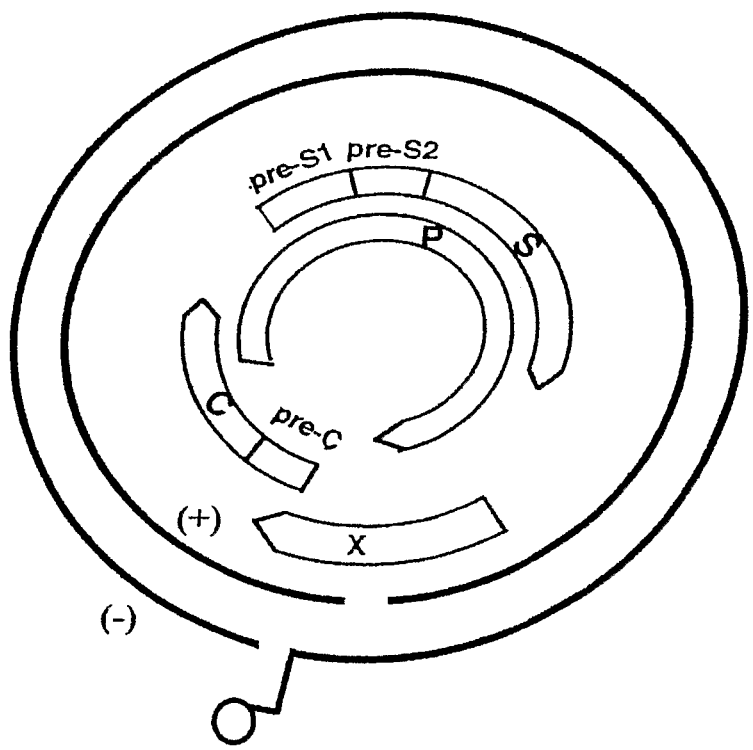
FIG. 1 is a diagrammatic representation showing the partially double stranded DNA HBV genome showing the overlapping open reading frames encoding surface (S), core (C), polymerase (P) and X gene.

The present invention is predicated in part on the identification and isolation of nucleoside or nucleotide analog-resistant variants of HBV following treatment of patients with in ADV or optionally LMV or ETV or TFV and LMV, or ETV alone or in combination with ADV and optionally one or more other nucleoside analogs or nucleotide analogs such as TFV or FTC or other anti-HBV agents. In particular, ADV or ADV and LMV or ETV treated patients give rise to variants of HBV exhibiting decreased or reduced sensitivity to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. Reference herein to "decreased" or "reduced" in relation to sensitivity to ADV and/or LMV and/or FTC and/or TFV and/or ETV includes and encompasses a complete or substantial resistance to the nucleoside or nucleotide analog or other anti-HBV agents as well as partial resistance and includes a replication rate or replication efficiency which is more than a wild-type in the presence of a nucleoside or nucleotide analog or other anti-HBV agents. In one aspect, this is conveniently measured by an increase in viral load during treatment, or alternatively, there is no substantial decrease in HBV DNA viral load from pre-treatment HBV DNA levels during treatment (i.e., non-response to treatment).

Accordingly, one aspect of the present invention contemplates an isolated HBV variant wherein said variant comprises a nucleotide mutation in a gene encoding a DNA polymerase resulting in at least one amino acid addition, substitution and/or deletion to said DNA polymerase and wherein said variant exhibits decreased sensitivity to one or more nucleoside or nucleotide analogs selected from the list consisting of ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

Another aspect of the present invention provides a method for determining the potential for an HBV to exhibit reduced sensitivity to a nucleoside or nucleotide analog selected from ADV, LMV, TFV, FTC and ETV or a combination thereof or optionally other nucleoside or nucleotide analogs, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and A through E or a region proximal thereto of said DNA polymerase and associated with resistance or decreases sensitivity to one or more of ADV, LMV, TFV, FTC and/or wherein the presence of such a mutation is an indication of the likelihood of resistance to said one or more of ADV, LMV, TFV, FTC and/or ETV.

Before describing the present invention in detail, it is to be understood that unless otherwise indicated, the subject invention is not limited to specific formulations of components, manufacturing methods, dosage regimens, or the like, as such may vary. It is also to be understood that the terminology used herein is for the purpose of describing particular embodiments only and is not intended to be limiting.

It must be noted that, as used in the subject specification, the singular forms "a", "an" and "the" include plural aspects unless the context clearly dictates otherwise. Thus, for example, reference to "a nucleoside or nucleotide analog" includes a single analog, as well as two or more analogs; reference to "an HBV variant" includes reference to two or more HBV variants; and so forth.

In describing and claiming the present invention, the following terminology is used in accordance with the definitions set forth below.

The terms "analog", "compound", "active agent", "pharmacologically active agent", "medicament", "active" and "drug" are used interchangeably herein to refer to a chemical compound that induces a desired effect such as inhibit viral replication, infection, maintenance, assembly and/or the function of an enzyme such as HBV DNA polymerase. The terms also encompass pharmaceutically acceptable and pharmacologically active ingredients of those active agents specifically mentioned herein including but not limited to salts, esters, amides, prodrugs, active metabolites, analogs and the like. When the terms "analog", "compound", "active agent", "pharmacologically active agent", "medicament", "active" and "drug" are used, then it is to be understood that this includes the active agent per se as well as pharmaceutically acceptable, pharmacologically active salts, esters, amides, prodrugs, metabolites, analogs, etc. An anti-HBV agent other than a nucleoside or nucleotide analog (i.e. non-nucleoside or non-nucleotide analog agent) includes a DNA polymerase antagonist.

The present invention contemplates, therefore, compounds useful in inhibiting HBV replication, infection, maintenance, assembly and/or the function of an enzyme such as HBV DNA polymerase. Reference to an "analog", "compound", "active agent", "pharmacologically active agent", "medicament", "active" and "drug" such as ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. A "combination" also includes a two-part or more such as a multi-part anti-HBV therapeutic composition where the agents are provided separately and given or dispensed separately or admixed together prior to dispensation.

The terms "effective amount" and "therapeutically effective amount" of an agent as used herein mean a sufficient amount of the agent to provide the desired therapeutic or physiological effect of inhibiting HBV replication, infection, maintenance, assembly and/or the function of an enzyme such as HBV DNA polymerase. Furthermore, an "effective HBV-inhibiting amount" or "effective symptom-ameliorating amount" of an agent is a sufficient amount of the agent to directly or indirectly inhibit replication, infection, maintenance, assembly and/or the function of an enzyme such as HBV DNA polymerase. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation.

By "pharmaceutically acceptable" carrier, excipient or diluent is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like.

Similarly, a "pharmacologically acceptable" salt, ester, emide, prodrug or derivative of a compound as provided herein is a salt, ester, amide, prodrug or derivative that this not biologically or otherwise undesirable.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage in relation to HBV infection. Thus, for example, "treating" a patient involves prevention of HBV infection as well as treatment of a clinically HBV symptomatic individual by inhibiting HBV replication, infection, maintenance, assembly and/or the function of an enzyme such as HBV DNA polymerase. Thus, for example, the present method of "treating" a patient with HBV infection or with a propensity for one to develop encompasses both prevention of HBV infection as well as treating HBV infection or symptoms thereof. In any event, the present invention contemplates the treatment or prophylaxis of HBV infection.

"Patient" as used herein refers to an animal, preferably a mammal and more preferably a primate including a lower primate and even more preferably a human who can benefit from the formulations and methods of the present invention. A patient regardless of whether a human or non-human animal may be referred to as an individual, subject, animal, host or recipient. The compounds and methods of the present invention have applications in human medicine, veterinary medicine as well as in general, domestic or wild animal husbandry. For convenience, an "animal" includes an avian species such as a poultry bird (including ducks, chicken, turkeys and geese), an aviary bird or game bird. The condition in a non-human animal may not be a naturally occurring HBV infection but HBV-like infection may be induced.

As indicated above, the preferred animals are humans, non-human primates such as marmosets, baboons, orangutans, lower primates such as tupia, livestock animals, laboratory test animals, companion animals or captive wild animals. A human is the most preferred target. However, non-human animal models may be used.

Examples of laboratory test animals include mice, rats, rabbits, guinea pigs and hamsters. Rabbits and rodent animals, such as rats and mice, provide a convenient test system or animal model as do primates and lower primates. Livestock animals include sheep, cows, pigs, goats, horses and donkeys. Non-mammalian animals such as avian species, zebrafish, amphibians (including cane toads) and *Drosophila* species such as *Drosophila melanogaster* are also contemplated. Instead of a live animal model, a test system may also comprise a tissue culture system.

An "anti-HBV agent" includes a nucleoside or nucleotide analog, protein, chemical compound, RNA or DNA or RNAi or siRNA oligonucleotide (either DNA-derived or synthetic).

Preferably, the decreased sensitivity is in respect of ADV. Alternatively, the decreased sensitivity is in respect of LMV. Alternatively, the decreased sensitivity is in respect of TFV. Alternatively, the decreased sensitivity is in respect of FTC. Alternatively, the decreased sensitivity is in respect of ETV. Alternatively, the decreased sensitivity is in respect of ETV and optionally ADV and LMV. Alternatively, the decreased sensitivity is in respect of ADV and TFV and optionally ETV. Alternatively, the decreased sensitivity is in respect of LMV and TFV and optionally ETV. Alternatively, the decreased sensitivity is in respect of ADV and FTC and optionally ETV. Alternatively, the decreased sensitivity is in respect to FTC and TFV and optionally ETV. Alternatively, the decreased sensitivity is in respect of FTC and LMV and optionally ETV. Alternatively, the decreased sensitivity is in respect of ADV and LMV and TFV and optionally ETV. Alternatively, the decreased sensitivity is in respect to ADV and TFV and FTC and optionally ETV. Alternatively, the decreased sensitivity is in respect to LMV and TFV and FTC and optionally ETV. Alternatively, the decrease sensitivity is in respect of ADV and LMV and FTC and optionally ETV. Alternatively, the decreased sensitivity is in respect of ADV and FTC and TFV and LMV and optionally ETV.

As indicated above, reference herein to "anti-HBV agents" includes nucleoside and nucleotide analogs, other DNA polymerase antagonists as well as immunological reagents (e.g. antibodies to HBV surface components) and chemical, proteinaceous and nucleic acid agents which inhibit or otherwise interfere with viral replication, maintenance, infection, assembly or release. Reference herein to "nucleic acid" includes reference to a sense or antisense molecule, RNA or DNA, oligonucleotides and RNAi and siRNA molecules and complexes containing same.

In addition to a mutation in the gene encoding DNA polymerase, due to the overlapping nature of the HBV genome (FIG. 1), a corresponding mutation may also occur in the gene encoding the S gene encoding the surface antigen (HBsAg) resulting in reduced interactivity of immunological reagents such as antibodies and immune cells to HBsAg. The reduction in the interactivity of immunological reagents to a viral surface component generally includes the absence of immunological memory to recognize or substantially recognize the viral surface component. The present invention extends, therefore, to an HBV variant exhibiting decreased sensitivity to ADV, or alternatively to ADV, LMV, TFV, ETV or FTC; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof or a reduced interactivity of an immunological reagent to HBsAg wherein the variant is selected for following ADV and LMV combination or sequential treatment. The term "sequential" in this respect means ADV followed by LMV and/or TFV and/or ETV, and/or FTC, LMV followed by ADV and/or TFV and/or FTC and/or ETV or ETV followed by one or more of ADV, FTC, LMV and/or TFV, or multiple sequential administrations of each of ETV, ADV, LMV and/or TFV and/or FTC.

A viral variant may, therefore, carry a mutation only in the DNA polymerase gene or both in the DNA polymerase gene and the S gene. The term "mutation" is to be read in its broadest context and includes multiple mutations.

The present invention extends to a mutation and any domain of the HBV DNA polymerase and in particular regions F and G, and domains A through to E provided said mutation leads to decreased sensitivity to ADV and LMV, and/or TFV and/or ETV and/or FTC or combinations thereof.

In this specification, reference is particularly made to the conserved regions of the DNA polymerase as defined by domains A to E. Regions A to E are defined by the amino acid sequence set forth in Formula II in Australian Patent No. 734831.

Preferably, the mutation results in an altered amino acid sequence in any one or more of domains F and G, and domains A through to E or regions proximal thereto of the HBV DNA polymerase.

Another aspect of the present invention provides an HBV variant comprising a mutation in an overlapping open reading frame in its genome wherein said mutation is in a region defined by one or more of domains F and G, and domains A through to E of HBV DNA polymerase and wherein said variant exhibits decreased sensitivity to ADV and/or optionally other nucleoside or nucleotide analogs or other anti-HBV agents or combinations thereof.

Yet, another aspect of the present invention provides an HBV variant comprising a mutation in an overlapping open reading frame in its genome wherein said mutation is in a region defined by one or more of domains F and G, and domains A through to E of HBV DNA polymerase and wherein said variant exhibits decreased sensitivity to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

Another preferred aspect of the present invention contemplates an HBV variant comprising a mutation in the nucleotide sequence encoding HBsAg resulting in an amino acid addition, substitution and/or deletion in said HBsAg wherein said variant exhibits decreased sensitivity to ADV, and/or optionally other nucleoside or nucleotide analogs or other anti-HBV agents or combinations thereof.

Yet, another preferred aspect of the present invention contemplates an HBV variant comprising a mutation in the nucleotide sequence encoding HBsAg resulting in an amino acid addition, substitution and/or deletion in said HBsAg wherein said variant exhibits decreased sensitivity to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

More particularly, the present invention provides a variant HBV comprising a surface antigen having an amino acid sequence with a single or multiple amino acid substitution, addition and/or deletion or a truncation compared to a surface antigen from a reference or wild-type HBV and wherein an antibody generated to the reference or wild-type surface antigen exhibits reduced capacity for neutralizing said HBV variant, said variant selected by exposure of a subject to ADV, and/or optionally other nucleoside or nucleotide analogs or other anti-HBV agents or combinations thereof.

More particularly, the present invention provides a variant HBV comprising a surface antigen having an amino acid sequence with a single or multiple amino acid substitution, addition and/or deletion or a truncation compared to a surface antigen from a reference or wild-type HBV and wherein an antibody generated to the reference or wild-type surface antigen exhibits reduced capacity for neutralizing said HBV variant, said variant selected by exposure of a subject to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

The term "combination therapy" means that both combinations of ADV, LMV, FTC, TFV, and/or ETV are co-administered in the same composition or simultaneously in separate compositions. The term "sequential therapy" means that the two agents are administered within seconds, minutes, hours, days or weeks of each other and in either order. Sequential therapy also encompasses completing a therapeutic course with one or other of ADV, LMV, FTC, TFV or ETV and then completing a second or third or subsequent therapeutic courses with the other of ADV, LMV, FTC, TFV or ETV.

Accordingly, another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV therapy or therapy by one or more other nucleoside or nucleotide analogs or other anti-HBV agents.

Accordingly, another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV therapy or therapy by one or more other nucleoside or nucleotide analogs or other anti-HBV agents.

Another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to LMV therapy or therapy by one or more other nucleoside or nucleotide analogs or other anti-HBV agents.

Yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC therapy or therapy by one or more other nucleoside or nucleotide analogs or other anti-HBV agents.

Still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to TFV therapy or therapy by one or more other nucleoside or nucleotide analogs or other anti-HBV agents.

Yet still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ETV therapy or therapy by one or more other nucleoside or nucleotide analogs or other anti-HBV agents.

Even still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and TFV therapy or therapy by one or more other nucleoside or nucleotide analogs or other anti-HBV agents.

Yet still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and ETV therapy or therapy by one or more other nucleoside or nucleotide analogs or other anti-HBV agents.

A further aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to LMV and TFV therapy or therapy by one or more other nucleoside or nucleotide analogs or other anti-HBV agents.

Yet a further aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to LMV and ETV therapy or therapy by one or more other nucleoside or nucleotide analogs or other anti-HBV agents.

Another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and FTC therapy or therapy by one or more other nucleoside or nucleotide analogs or other anti-HBV agents.

Yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to TFV and FTC therapy or therapy by one or more other nucleoside or nucleotide analogs or other anti-HBV agents.

Still another aspect another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to TFV and ETV therapy or therapy by one or more other nucleoside or nucleotide analogs or other anti-HBV agents.

Still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC and LMV therapy or therapy by one or more other nucleoside or nucleotide analogs or other anti-HBV agents.

Even another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC and ETV therapy or therapy by one or more other nucleoside or nucleotide analogs or other anti-HBV agents.

Even yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV and TFV and/or ETV therapy or therapy by one or more other nucleoside or nucleotide analogs or other anti-HBV agents.

Even still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV and TFV and/or ETV therapy or therapy by one or more other nucleoside or nucleotide analogs or other anti-HBV agents.

A further aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV and FTC and/or ETV therapy or therapy by one or more other nucleoside or nucleotide analogs or other anti-HBV agents.

Another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC, LMV and TFV and/or ETV therapy or therapy by one or more other nucleoside or nucleotide analogs or other anti-HBV agents.

Yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, FTC and TFV and/or ETV therapy or therapy by one or more other nucleoside or nucleotide analogs or other anti-HBV agents.

Still yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV, FTC and TFV and/or ETV therapy or therapy by one or more other nucleoside or nucleotide analogs or other anti-HBV agents.

Preferably, the variants are in isolated form such that they have undergone at least one purification step away from naturally occurring body fluid. Alternatively, the variants may be maintained in isolated body fluid or may be in DNA form. The present invention also contemplates infectious molecular clones comprising the genome or parts thereof from a variant HBV. Furthermore, the present invention provides isolated components from the variant HBVs such as but not limited to an isolated HBsAg. Accordingly, the present invention provides an isolated HBsAg or a recombinant form thereof or derivative or chemical equivalent thereof, said HBsAg being from a variant HBV selected by exposure of a subject to one or more of ADV, LMV, FTC, TFV and/or ETV or optionally one or more nucleoside or nucleotide analogs or other anti-HBV agents.

More particularly, yet another aspect of the present invention is directed to an isolated variant HBsAg or a recombinant or derivative form thereof or a chemical equivalent thereof wherein said HBsAg or its recombinant or derivative form or its chemical equivalent exhibits an altered immunological profile compared to an HBsAg from a reference HBV, said HBsAg being from a variant HBV selected by exposure of a subject to one or more of ADV, LMV, FTC, TFV and/or ETV or optionally one or more nucleoside or nucleotide analogs or other anti-HBV agents.

Even more particularly, the present invention provides an isolated variant HBsAg or a recombinant or derivative form thereof or a chemical equivalent thereof wherein said HBsAg or its recombinant or derivative form or its chemical equivalent comprises an amino acid sequence with a single or multiple amino acid substitution, addition and/or deletion or a truncation compared to an HBsAg from a reference HBV and wherein a neutralizing antibody directed to a reference HBV exhibits no or reduced neutralising activity to an HBV carrying said variant HBsAg, said HBsAg being from a variant HBV selected by exposure of a subject to one or more of ADV, LMV, FTC, TFV and/or ETV or optionally one or more nucleoside or nucleotide analogs or other anti-HBV agents.

Particular mutations in the HBV DNA polymerase contemplated by the present invention include variants selected from subjects with HBV recurrence following administration of ADV and/or optionally other nucleoside or nucleotide analogs or other anti-HBV agents or combinations thereof. Nucleoside or nucleotide analogs or other anti-HBV agents may be indicated during, after or prior to a transplantation procedure (e.g. bone marrow transplantation (BMT) or orthotopic liver transplantation (OLT)) or following treatment of subjects diagnosed with hepatitis. Following selection of variants, viral loads are obtainable at levels similar to pre-treatment levels or increase while on therapy.

In addition, particular mutations in the HBV DNA polymerase include variants selected from subjects with HBV recurrence following ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. Nucleoside or nucleotide analogs or other anti-HBV agents may be indicated during, after or prior to a transplantation procedure (e.g. bone marrow transplantation (BMT) or OLT) or following treatment of patients diagnosed with hepatitis. Following selection of variants, viral loads are obtainable at levels similar to pre-treatment levels or increase while on therapy.

Particular mutants in the rt region include, rtS78T, rtS85T, rtT128N, rtT184G, rtS202I, rtV207M, rtM204A, rtN236A/V/S, rtN238H or a combination thereof or an equivalent mutation.

Such HBV variants are proposed to exhibit a decreased sensitivity to; ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combination thereof. It should be noted that the nomenclature system for amino acid positions is based on the methionine residues in the YMDD motif being designated codon rtM204. This numbering system is different to that in Australian Patent No. 734831 where the methionine residue in the YMDD motif within the polymerase gene is designated codon 550. In this regard, rtL180M and rtM204V correspond to L526M and M550V, respectively, in Australian Patent No. 734831.

Corresponding mutations may also occur in envelope genes such as in one or more of PreS1, PreS2 and S.

In particular, the present invention provides an isolated Hepatitis B virus (HBV) variant wherein said variant comprises a nucleotide mutation in a gene encoding a DNA polymerase resulting in amino acid mutation rtS85T in said DNA polymerase wherein said variant exhibits decreased sensitivity to adefovir dipivoxil (ADV).

Another potential mode of action of ADV and other acyclic nucleoside phosphonates is that of immune stimulation (Calio et al, *Antiviral Res.* 23: 77-89, 1994). A number of mutations resulted in changes in the envelope gene detected in HBV variants which may be associated with immune escape. These changes include in one embodiment include in sC69stop, sC76stop, sR79H, sP120T, sL176V, sV194F, sI195M, sW196R, or a combination thereof or an equivalent mutation, or a combination thereof or an equivalent mutation.

The identification of the variants of the present invention permits the generation of a range of assays to detect such variants. The detection of such variants may be important in identifying resistant variants to determine the appropriate form of chemotherapy and/or to monitor vaccination protocols, or develop new or modified vaccine preparations.

Another aspect of the present invention contemplates a method for determining the potential for an HBV to exhibit reduced sensitivity to ADV; and/or optionally other nucleoside or nucleotide analogs or other anti-HBV agents or combinations thereof and/or optionally other nucleoside or nucleotide analogs or other anti-HBV agents, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and G, and A domains through to E or a region proximal thereto of said DNA polymerase and associated with resistance or decreased sensitivity to ADV, and/or optionally other nucleoside or nucleotide analogs or other anti-HBV agents or combinations thereof and/or optionally other nucleoside or nucleotide analogs or other anti-HBV agents wherein the presence of such a mutation is an indication of the likelihood of resistance to said ADV, and/or optionally other nucleoside or nucleotide analogs or other anti-HBV agents or combinations thereof.

Still another aspect of the present invention contemplates a method for determining the potential for an HBV to exhibit reduced sensitivity to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and G, and A domains through to E or a region proximal thereto of said DNA polymerase and associated with resistance or decreased sensitivity to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents wherein the presence of such a mutation is an indication of the likelihood of resistance to said ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents.

Accordingly, another aspect of the present invention provides a method for determining the potential for an HBV to exhibit reduced sensitivity to a nucleoside or nucleotide analog selected from ADV, LMV, TFV, FTC and ETV or optionally other nucleoside or nucleotide analogs, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and A through E or a region proximal thereto of said DNA polymerase and associated with resistance or decreases sensitivity to one or more of ADV, LMV, TFV, FTC and/or ETV wherein the presence of such a mutation is an indication of the likelihood of resistance to said one or more of ADV, LMV, TFV, FTC and/or ETV.

Preferably, the assay detects one or more of the following mutations: rtS78T, rtS85T, rtT128N, rtT184G, rtS202I, rtV207M, rtM204A, rtN236A/V/S, rtN238H or a combination thereof or an equivalent mutation is indicative of a variant wherein said variant exhibits a decreased sensitivity to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combination thereof.

Accordingly, another aspect of the present invention produces a method for determining whether an HBV strain exhibits reduced sensitivity to a nucleoside or nucleotide analog or other anti-HBV agents, said method comprising isolating DNA or corresponding mRNA from said HBV and screening for a mutation in the nucleotide sequence encoding the DNA polymerase and/or a corresponding region of the S gene, wherein the presence of a mutation selected from, in one embodiment include sC69stop, sC76stop, sR79H, sP120T, sL176V, sV194F, sI195M, sW196R, or a combination thereof or an equivalent mutation, in even still another embodiment, rtS78T, rtS85T, rtT128N, rtT184G, rtS202I, rtV207M, rtM204A, rtN236A/V/S, rtN238H or a combination thereof or an equivalent mutation, or combinations thereof or an equivalent one or more other mutation is indicative of a variant which exhibits a decreased sensitivity to; ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

A further aspect of the present invention produces a method for determining whether an HBV strain exhibits reduced sensitivity to a nucleoside or nucleotide analog or other anti-HBV agents, said method comprising isolating DNA or corresponding mRNA from said HBV and screening for a mutation in the nucleotide sequence encoding the DNA polymerase and/or a corresponding region of the S gene, wherein the presence of a mutation selected from, in one embodiment, sC69stop, sC76stop, sR79H, sP120T, sL176V, sV194F, sI195M, sW196R, or a combination thereof or an equivalent mutation, in even still another embodiment, rtS78T, rtS85T, rtT128N, rtT184G, rtS202I, rtV207M, rtM204A, rtN236A/V/S, rtN238H or a combination thereof or an equivalent mutation, combinations thereof or an equivalent one or more other mutation is indicative of a variant which exhibits a decreased sensitivity to; ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

In particular, the present invention contemplates a method for determining the potential for an HBV to exhibit reduced sensitivity to ADV said method comprising isolating DNA or corresponding mRNA from the HBV and screening for the presence of a genomic mutation resulting in amino acid mutation rtS85T in its DNA polymerase wherein the presence of this substitution is indicative of an HBV with reduced sensitivity to ADV.

The detection of HBV or its components in cells, cell lysates, cultured supernatant fluid and bodily fluid may be by any convenient means including any nucleic acid-based detection means, for example, by nucleic acid hybridization techniques or via one or more polymerase chain reactions (PCRs). The term "bodily fluid" includes any fluid derived from the blood, lymph, tissue or organ systems including serum, whole blood, biopsy and biopsy fluid, organ explants and organ suspension such as liver suspensions. The invention further encompasses the use of different assay formats of said nucleic acid-based detection means, including restriction fragment length polymorphism (RFLP), amplified fragment length polymorphism (AFLP), single-strand chain polymorphism (SSCP), amplification and mismatch detection (AMD), interspersed repetitive sequence polymerase chain reaction (IRS-PCR), inverse polymerase chain reaction (iPCR) and reverse transcription polymerase chain reaction (RT-PCR), amongst others. Other forms of detection include Northern blots, Southern blots, PCR sequencing, antibody procedures such as ELISA, Western blot and immunohistochemistry. A particularly useful assay includes the reagents and components required for immobilized oligonucleotide- or oligopeptide-mediated detection systems.

One particularly useful nucleic acid detection system is the reverse hybridization technique. In this technique, DNA from an HBV sample is amplified using a biotin or other ligand-labeled primer to generate a labeled amplificon. Oligonucleotides immobilized to a solid support such as a nitrocellulose film are then used to capture amplified DNA by hybridization. Specific nucleic acid fragments are identified via biotin or the ligand. Generally, the labeled primer is specific for a particular nucleotide variation to be detected. Amplification occurs only if the variation to be detected is present. There are many forms of the reverse hybridization assay and all are encompassed by the present invention.

Another aspect contemplated by the present invention provides a method for detecting a variant HBV exhibiting an altered immunological profile said method comprising isolating an HBV from a subject exposed to a nucleoside or nucleotide analog ADV and/or optionally other nucleoside or nucleotide analogs or other anti-HBV agents or combinations thereof, and then contacting said HBV with a panel of one or more antibodies to a surface antigen and screening for any change in binding affinity or binding spectrum.

Another aspect contemplated by the present invention provides a method for detecting a variant HBV exhibiting an altered immunological profile said method comprising isolating an HBV from a subject exposed to a nucleoside or nucleotide analog selected from the listed consisting of ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof, and then contacting said HBV with a panel of one or more antibodies to a surface antigen and screening for any change in binding affinity or binding spectrum.

In another embodiment, the present invention contemplates a method for detecting a variant HBV exhibiting an altered immunological profile said method comprising isolating a serum sample from a subject exposed to a nucleoside or nucleotide analog ADV and/or optionally other nucleoside or nucleotide analogs or other anti-HBV agents or combinations thereof, and then contacting the serum with a panel of HBV surface antigens or antibody-binding fragments thereof and screening for any change in binding affinity or binding spectrum.

In a related embodiment, the present invention contemplates a method for detecting a variant HBV exhibiting an altered immunological profile said method comprising isolating a serum sample from a subject exposed to a nucleoside or nucleotide analog selected from the listed consisting of ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof, and then contacting the serum with a panel of HBV surface antigens or antibody-binding fragments thereof and screening for any change in binding affinity or binding spectrum.

Detecting HBV replication in cell culture is particularly useful.

This and other aspects of the present invention is particularly amenable to microarray analysis such as to identify oligonucleotides including sense and antisense molecules, RNAi or siRNA molecules or DNA or RNA-binding molecules which down-regulate genomic sequences or transcripts of HBV. Microarray analysis may also be used to identify particular mutations in the HBV genome such as within the HBV DNA polymerase-coding region or the HBsAg-coding region.

Another aspect of the present invention contemplates a method for detecting an agent which exhibits inhibitory activity to an HBV by:
  generating a genetic construct comprising a replication competent-effective amount of the genome from the HBV contained in a plasmid vector and then transfecting said cells with said construct;
  contacting the cells, before, during and/or after transfection, with the agent to be tested;
  culturing the cells for a time and under conditions sufficient for the HBV to replicate, express genetic sequences and/or assemble and/or release virus or virus-like particles if resistant to said agents; and
  then subjecting the cells, cell lysates or culture supernatant fluid to viral- or viral-component-detection means to determine whether or not the virus has replicated, expressed genetic material and/or assembled and/or been released in the presence of the agent.

In a preferred embodiment, the plasmid vector may include genes encoding part or all of other viral vectors such as baculovirus or adenovirus (Ren and Nassal, 2001, supra) and the method comprises:
  generating a genetic construct comprising a replication competent-effective amount of the genome from the HBV contained in or fused to an amount of a baculovirus genome or adenovirus genome effective to infect cells and then infecting said cells with said construct;
  contacting the cells, before, during and/or after infection, with the agent to be tested;
  culturing the cells for a time and under conditions sufficient for the HBV to replicate, express genetic sequences and/or assemble and/or release virus or virus-like particles if resistant to said agent; and
  then subjecting the cells, cell lysates or culture supernatant fluid to viral- or viral-component-detection means to determine whether or not the virus has replicated, expressed genetic material and/or assembled and/or been released in the presence of the agent.

In an alternative embodiment, the method comprises:
  generating a continuous cell line comprising an infectious copy of the genome of the HBV in a replication competent effective amount such that said infectious HBV genome is stably integrated into said continuous cell line such as but not limited to 2.2.15 or AD;
  contacting the cells with the agent to be tested;
  culturing the cells for a time and under conditions sufficient for the HBV to replicate, express genetic sequences and/or assemble and/or release virus or virus-like particles if resistant to the agent; and
  then subjecting the cells, cell lysates or culture supernatant fluid to viral- or viral-component-detection means to determine whether or not the virus has replicated, expressed genetic material and/or assembled and/or been released in the presence of the agent.

The above-mentioned methods are particularly useful in identifying or developing agents against HBV variants such as those carrying mutations, in one embodiment, rtS78T, rtS85T, rtT128N, rtT184G, rtS202I, rtV207M, rtM204A, rtN236A/V/S, rtN238H or a combination thereof or an equivalent mutation, or a combination thereof or an equivalent mutation; in a further embodiment, sC69stop, sC76stop, sR79H, sP120T, sL176V, sV194F, sI195M, sW196R, or a combination thereof or an equivalent mutation.

Hence, another aspect of the present invention contemplates a method for detecting an agent which exhibits inhibitory activity to an HBV which exhibits resistance or decreased sensitivity to one or more of ADV, said method comprising:
  generating a genetic construct comprising a replication competent-effective amount of the genome from said HBV contained in a plasmid vector and then transfecting said cells with said construct wherein said HBV genome comprising a mutation resulting in amino acid substitution rtS85T in its DNA polymerase;
  contacting said cells, before, during and/or after transfection, with the agent to be tested;
  culturing said cells for a time and under conditions sufficient for the HBV to replicate, express genetic sequences and/or assemble and/or release virus or virus-like particles if resistant to said agent; and
  subjecting the cells, cell lysates or culture supernatant fluid to viral- or viral-component-detection means to determine whether or not the virus has replicated, expressed genetic material and/or assembled and/or been released in the presence of said agent.

Another aspect of the present invention contemplates a method for determining whether an HBV strain exhibits reduced sensitivity to a nucleoside or nucleotide analog or other potential anti-HBV agent, said method comprising isolating DNA or corresponding mRNA from said HBV and screening for a mutation in the nucleotide sequence of the envelope genes or DNA polymerase gene selected from, in one embodiment, in one embodiment, rtS78T, rtS85T, rtT128N, rtT184G, rtS202I, rtV207M, rtM204A, rtN236A/V/S, rtN238H or a combination thereof or an equivalent mutation, or a combination thereof or an equivalent mutation; in a further embodiment, sC69stop, sC76stop, sR79H, sP120T, sL176V, sV194F, sI195M, sW196R, or a combination thereof or an equivalent mutation and/or optionally other nucleoside or nucleotide analogs or other anti-HBV agents or combination thereof.

The detection of amino acid variants of DNA polymerase is conveniently accomplished by a range of amino acid detection techniques. Where an HBV variant comprises an amino acid change, then such an isolate is considered a putative HBV variant having an altered DNA polymerase activity.

The present invention further contemplates agents which inhibit ADV, and/or optionally other nucleoside or nucleotide analogs or other anti-HBV agents or combinations thereof resistant HBV variants. Such agents are particularly useful if long term treatment by ADV, and/or optionally other nucleoside or nucleotide analogs is contemplated by the clinician. The agents may be DNA or RNA or proteinaceous or non-proteinaceous chemical molecules. Natural product screening such as from plants, coral and microorganisms is also contemplated as a useful potential source of masking agents as is the screening of combinatorial or chemical libraries. The agents may be in isolated form or in the form of a pharmaceutical composition or formulation and may be administered in place of or sequentially or simultaneously with a nucleoside or nucleotide analog. Furthermore, rationale drug design is contemplated including solving the crystal or NMR structure of, for example, HBV DNA polymerase and designing agents which can bind to the enzyme's active site. This approach may also be adapted to other HBV components.

In addition, the present invention contemplates agents which inhibit ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof resistant HBV variants. Such agents are particularly useful if long term treatment by ADV, LMV, FTC, TFV and/or ETV and/or optionally other nucleoside or nucleotide analogs such as TFV is contemplated by the clinician. The agents may be DNA or RNA or proteinaceous or non-proteinaceous chemical molecules. Natural product screening such as from plants, coral and microorganisms is also contemplated as a useful potential source of masking agents as is the screening of combinatorial or chemical libraries. The agents may be in isolated form or in the form of a pharmaceutical composition or formulation and may be administered in place of or sequentially or simultaneously with a nucleoside or nucleotide analog.

Furthermore, rationale drug design is contemplated including solving the crystal or NMR structure of, for example, HBV DNA polymerase and designing agents which can bind to the enzyme's active site. This approach may also be adapted to other HBV components.

Accordingly, another aspect of the present invention contemplates a method for detecting an agent which exhibits inhibitory activity to an HBV which exhibits resistance or decreased sensitivity to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combination thereof, said method comprising:

generating a genetic construct comprising a replication competent-effective amount of the genome from said HBV contained in a plasmid vector and then transfecting said cells with said construct;

contacting said cells, before, during and/or after transfection, with the agent to be tested;

culturing said cells for a time and under conditions sufficient for the HBV to replicate, express genetic sequences and/or assemble and/or release virus or virus-like particles if resistant to said agent; and subjecting the cells, cell lysates or culture supernatant fluid to viral- or viral-component-detection means to determine whether or not the virus has replicated, expressed genetic material and/or assembled and/or been released in the presence of said agent.

Still another aspect of the present invention provides a method for detecting an agent which exhibits inhibitory activity to an HBV which exhibits resistance or decreased sensitivity to, ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combination thereof, said method comprising:

generating a genetic construct comprising a replication competent-effective amount of the genome from said HBV contained in or fused to an amount of a baculovirus genome effective to infect cells and then infecting said cells with said construct;

contacting said cells, before, during and/or after infection, with the agent to be tested;

culturing said cells for a time and under conditions sufficient for the HBV to replicate, express genetic sequences and/or assemble and/or release virus or virus-like particles if resistant to said agent; and subjecting the cells, cell lysates or culture supernatant fluid to viral- or viral-component-detection means to determine whether or not the virus has replicated, expressed genetic material and/or assembled and/or been released in the presence of said agent.

Preferably, the HBV genome is stably integrated into the cells' genome.

Preferably, the HBV genome comprises a mutation encoding an rtS85T mutation in the DNA polymerase.

Particularly useful cells are 2.2.15 cells (Price et al, *Proc. Natl. Acad. Sci. USA* 86(21): 8541-8544, 1989 or AD cells (also known as HepAD32 cells or HepAD79 cells [Ying et al, 2000 Spra].

Whilst the baculovirus vector is a particularly useful in the practice of the present invention, the subject invention extends to a range of other vectors such as but not limited to adenoviral vectors.

The present invention further extends to cell lines (e.g. 2.2.15 or AD cells) carrying genetic constructs comprising all or a portion of an HBV genome or a gene or part of a gene therefrom.

The present invention also provides for the use of the subject HBV variants to screen for anti-viral agents. These anti-viral agents inhibit the virus. The term "inhibit" includes antagonizing or otherwise preventing infection, replication, assembly and/or release or any intermediate step. Preferred anti-viral agents include nucleoside or nucleotide analogs or anti-HBV agents, however, the present invention extends to non-nucleoside molecules.

In particular, the present invention provides the use of a variant HBV exhibiting reduced sensitivity to ADV and having amino acid substitution rtS85T in its DNA polymerase in the manufacture of a medicament for the treatment or prophylaxis of HBV infection.

In addition, rational drug design is also contemplated to identify or generate chemical molecules which either mimic a nucleoside or which interact with a particular nucleotide sequence or a particular nucleotide. Combinatorial chemistry and two hybrid screening are some of a number of techniques which can be employed to identify potential therapeutic or diagnostic agents.

In one example, the crystal structure or the NMR structure of polymerase or the surface antigen is used to rationally design small chemical molecules likely to interact with key regions of the molecule required for function and/or antigenicity. Such agents may be useful as inhibitors of polymerase activity and/or may alter an epitope on the surface antigen.

Several models of the HBV polymerase have been prepared due to the similarity with reverse transcriptase from HIV (Das et al, *J. Virol.* 75(10): 4771-4779, 2001; Bartholomeusz et al, *Intervirology* 40(5-6): 337-342 1997; Allen et al, *Hepatology* 27(6): 1670-1677, 1998). The models of the HBV polymerase can be used for the rational drug design of new agents effective against HBV encoding the resistant mutations as well as wild type virus. The rational drug that is designed may be based on a modification of an existing antiviral agent such as the agent used in the selection of the HBV encoding the mutations associated with resistance. Viruses or clones expressing HBV genomic material encoding the mutations may also be used to screen for new antiviral agents.

In an alternative embodiment, the present invention also contemplates a method for detecting an agent which exhibits inhibitory activity to an HBV polymerase in an in vitro polymerase assay. The HBV polymerase activity can be examined using established assays (Gaillard et al, *Antimicrob Agents Chemother.* 46(4): 1005-1013, 2002; Xiong et al, *Hepatology* 28(6): 1669-1673, 1998).

As indicated above, microarray technology is also a useful means of identifying agents which are capable of interacting with defined HBV internal or external components. For example, arrays of HBV DNA polymerase or peptide fragments thereof carrying different amino acid variants may be used to screen for agents which are capable of binding or otherwise interacting with these molecules. This is a convenient way of determining the differential binding patterns of agents between HBV variants. Arrays of antibodies may also be used to screen for altered HBsAg molecules. Microarrays are also useful in proteomic analysis to identify molecules such as antibodies, interferons or cytokines which have an ability to interact with an HBV component. Microarrays of DNA and RNA molecules may also be employed to identify sense and antisense molecules for genetic regions on the HBV genome or transcripts thereof.

The above methods are particularly useful in identifying an inhibitor of an HBV resistant to or exhibiting reduced sensitivity to ADV, and/or optionally other nucleoside or nucleotide analogs or other anti-HBV agents or combinations thereof and/or optionally other nucleoside or nucleotide analogs or other anti-HBV agents or combination thereof. The present invention extends, therefore, to compositions of the inhibitors. The inhibitors may also be in the form of antibodies or genetic molecules such as ribozymes, antisense molecules and/or sense molecules for co-suppression or the induction of RNAi or may be other nucleoside or nucleotide analogs or other anti-HBV agents or derivatives of known analogs. Reference to RNAi includes reference to short, interfering RNAs (siRNA) and all RNAi-type molecules may be DNA-derived or synthetic.

The above methods are particularly useful in identifying an inhibitor of an HBV resistant to or exhibiting reduced sensitivity to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combination thereof. The present invention extends, therefore, to compositions of the inhibitors. The inhibitors may also be in the form of antibodies or genetic molecules such as ribozymes, antisense molecules and/or sense molecules for co-suppression or the induction of RNAi or may be other nucleoside or nucleotide analogs or other anti-HBV agents or derivatives of known analogs. Reference to RNAi includes reference to short, interfering RNAs (siRNA) and all RNAi-type molecules may be DNA-derived or synthetic.

The term "composition" includes a "pharmaceutical composition" or a formulation.

The inhibitor is referred to below as an "active ingredient" or "active compound" and may be selected from the list of inhibitors given above.

The composition may include an antigenic component of the HBV, a defective HBV variant or an agent identified through natural product screening or rational drug design (including combinatorial chemistry).

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

The pharmaceutical composition may also comprise genetic molecules such as a vector capable of transfecting target cells where the vector carries a nucleic acid molecule capable of encoding an aspartyl protease inhibitor. The vector may, for example, be a viral vector.

Pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fingi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with the active ingredient and optionally other active ingredients as required, followed by filtered sterilization or other appropriate means of sterilization. In the case of sterile powders for the preparation of sterile injectable solutions, suitable methods of preparation include vacuum drying and the freeze-drying technique which yield a powder of active ingredient plus any additionally desired ingredient.

When the active ingredient is suitably protected, it may be orally administered, for example, with an inert diluent or with an assimilable edible carrier, or it may be enclosed in hard or soft shell gelatin capsule, or it may be compressed into tablets. For oral therapeutic administration, the active ingredient may be incorporated with excipients and used in the form of ingestible tablets, buccal tablets, troches, capsules, elixirs, suspensions, syrups, wafers and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 200 mg of active compound. Alternative dosage amounts include from about 1 µg to about 1000 mg and from about 10 µg to about 500 mg. These dosages may be per individual or per kg body weight. Administration may be per hour, day, week, month or year.

The tablets, troches, pills, capsules and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and a flavouring. Of course, any material used in preparing any dosage unit form should be pharmaceutically pure and substantially non-toxic in the amounts employed. In addition, the active compound(s) may be incorporated into sustained-release preparations and formulations.

In a preferred embodiment, the present invention provides a composition comprising a variant HBV exhibiting reduced sensitivity to ADV and having amino acid mutation rtS85T in its DNA polymerase and one or more pharmaceutically acceptable carriers and/or diluents.

As stated above, the present invention further extends to an isolated HBsAg from the HBV variants herein described. More particularly, the present invention provides an HBsAg or a recombinant form thereof or derivative or chemical equivalent thereof. The isolated surface component and, more particularly, isolated surface antigen or its recombinant, derivative or chemical equivalents are useful in the development of biological compositions such as vaccine formulations.

In particular, the present invention provides an isolated HBV surface antigen comprising a mutation selected from the list consisting of sC69STOP, sC76STOP, sR79H, sP120T, sL176V, sV194F, sT195M and sW196R.

Another aspect of the present invention provides a composition comprising a variant HBV resistant to ADV, and/or optionally other nucleoside or nucleotide analogs or other anti-HBV agents or combinations thereof or an HBV surface antigen from said variant HBV or a recombinant or derivative form thereof or its chemical equivalent and one or more pharmaceutically acceptable carriers and/or diluents. Such a composition may be regarded as a therapeutic composition and is useful in generating an immune response including a humoral response. Generally, the HBV variants are "defective" and in themselves are unable to cause a sustained infection in a subject.

Yet another aspect of the present invention provides a composition comprising a variant HBV resistant to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or an HBV surface antigen from said variant HBV or a recombinant or derivative form thereof or its chemical equivalent and one or more pharmaceutically acceptable carriers and/or diluents. Such a composition may be regarded as a therapeutic composition and is useful in generating an immune response including a humoral response. Generally, the HBV variants are "defective" and in themselves are unable to cause a sustained infection in a subject.

As indicated above, antibodies may be generated to the mutant HBV agents and used for passive or direct vaccination against infection by these viruses. The antibodies may be generated in humans or non-human animals. In the case of the latter, the non-human antibodies may need to be deimmunized or more specifically humanized prior to use. Deimmunized may include, for example, grafting complimentarity determining regions (CDRs) from the variable region of a murine or non-human animal anti-HBV antibody onto a human consensus fragment antibody binding (Fab) polypeptide. Alternatively, amino acids defining epitopes in the variable region of the antibody may be mutated so that the epitopes are no longer recognized by the human MHC II complex.

Insofar as ribozyme, antisense or co-suppression (RNAi) or siRNA or complexes thereof repression is concerned, this is conveniently aimed at post-transcription gene silencing. DNA or RNA may be administered or a complex comprising RNAi or a chemical analog thereof specific for HBV mRNA may be employed.

All such molecules may be incorporated into pharmaceutical compositions.

In another embodiment, the present invention provides a biological composition comprising a variant HBV or an HBsAg or L, M or S proteins from said variant HBV or a recombinant or derivative form thereof or its chemical equivalent.

Generally, if an HBV is used, it is first attenuated. The biological composition according to this aspect of the present invention generally further comprises one or more pharmaceutically acceptable carriers and/or diluents.

The biological composition may comprise HBsAg or like molecule from one HBV variant or the composition may be a cocktail of HbsAgs or L, M or S proteins or like molecules from a range of ADV- and/or LMV- and/or, FTC- and/or TFV-resistant HBV variants. Similar inclusions apply where the composition comprises an HBV.

The present invention is further directed to the use of defective HBV variants in the manufacture of therapeutic vaccines to vaccinate individuals against infection by HBV strains having a particular nucleotide sequence or encoding a particular polymerase or surface antigen or L, M or S proteins.

Examples of suitable vaccine candidates are defective forms of HBV variants comprising a mutation selected from, in one embodiment, rtS78T, rtS85T, rtT128N, rtT184G, rtS202I, rtV207M, rtM204A, rtN236A/V/S, rtN238H or a combination thereof or an equivalent mutation, or a combination thereof or an equivalent mutation; in a further embodiment, sC69stop, sC76stop, sR79H, sP120T, sL176V, sV194F, sI195M, sW196R, or a combination thereof or an equivalent mutation.

In one embodiment, for example, an HBV variant may be identified having a particular mutation in its polymerase conferring resistance or decreased sensitivity to a nucleoside or nucleotide analog. This variant may then be mutated to render it defective, i.e. attenuated or unable to cause infection. Such a defective, nucleoside or nucleotide analog-resistant virus may then be used as a therapeutic vaccine against virulent viruses having the same mutation in its polymerase.

The subject invention extends to kits for assays for variant HBV resistant to ADV, and/or optionally other nucleoside or nucleotide analogs or other anti-HBV agents or combinations thereof. Such kits may, for example, contain the reagents from PCR or other nucleic acid hybridization technology or reagents for immunologically based detection techniques. A particularly useful assay includes the reagents and components required for immobilized oligonucleotide- or oligopeptide-mediated detection systems.

In addition, the subject invention extends to kits for assays for variant HBV resistant to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. Such kits may, for example, contain the reagents from PCR or other nucleic acid hybridization technology or reagents for immunologically based detection techniques. A particularly useful assay includes the reagents and components required for immobilized oligonucleotide- or oligopeptide-mediated detection systems.

Still another aspect of the present invention contemplates a method for determining the potential for an HBV to exhibit reduced sensitivity to ADV, and/or optionally other nucleoside or nucleotide analogs or other anti-HBV agents or combinations thereof said method comprising isolating DNA or corresponding mRNA from said HBV and screening for a mutation in the nucleotide sequence encoding HBV DNA polymerase resulting in at least one amino acid substitution, deletion and/or addition in any one or more of domains F and G, and domains A through to E or a region proximal thereto of said DNA polymerase and associated with resistance or decreased sensitivity to ADV, and/or optionally other nucleoside or nucleotide analogs or other anti-HBV agents or combinations thereof, wherein the presence of such a mutation is an indication of the likelihood of resistance to said ADV and/or optionally other nucleoside or nucleotide analogs or other anti-HBV agents or combinations thereof.

Yet, still another aspect of the present invention contemplates a method for determining the potential for an HBV to exhibit reduced sensitivity to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combination thereof, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and G, and domains A through to E or a region proximal thereto of said DNA polymerase and associated with resistance or decreased sensitivity to ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof, wherein the presence of such a mutation is an indication of the likelihood of resistance to said ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

An assessment of a potential viral variant is important for selection of an appropriate therapeutic protocol. Such an assessment is suitably facilitated with the assistance of a computer programmed with software, which inter alia adds input codes for at least two features associated with the viral variants to provide a value corresponding to the resistance or sensitivity of a viral variant to a particular chemical compound or immunological agent. This value is the "potency value" or "Pv" of the virus. The Pv can be determined from (a) the ability to exhibit resistance for reduced sensitivity to a particular compound or immunological agent; (b) an altered DNA polymerase from wild-type HBV; (c) an altered surface antigen from wild-type HBV; or (d) morbidity or recovery potential of a patient. Thus, in accordance with the present invention, the values for such features are stored in a machine-readable storage medium, which is capable of processing the data to provide a value for a particular viral variant or a biological specimen comprising same.

Thus, in another aspect, the invention contemplates a computer program product for assessing the likely usefulness of a viral variant or biological sample comprising same for determining an appropriate therapeutic protocol in a subject (FIG. 3), said product comprising:

(1) code that receives as input code for at least two features associated with said viral agents or biological sample comprising same, wherein said features are selected from:
 (a) the ability to exhibit resistance for reduced sensitivity to a particular compound or immunological agent;
 (b) an altered DNA polymerase from wild-type HBV;
 (c) an altered surface antigen from wild-type HBV; or
 (d) morbidity or recovery potential of a patient;
(2) code that adds said input code to provide a sum corresponding to a value for said viral variants or biological samples; and
(3) a computer readable medium that stores the codes.

The computer program, therefore, determines the Pv of the virus.

More particularly, the present invention is directed to a computer product for assessing the likely usefulness of an HBV variant or biological sample comprising same for determining an appropriate therapeutic protocol in a subject, said product comprising:

(I) code that receives an input code for at least two features associated with said HBV or biological sample comprising same, wherein said features are selected from:
 (a) a mutation in the HBV genome resulting in amino acid mutation rtS85T in its DNA polymerase;
 (b) a mutation in the HBV genome resulting in amino acid mutation rtM204I/V in its DNA polymerase;
 (c) a mutation in the HBV genome resulting in amino acid mutation rtS78T, rtT128N, rtT184G, rtS202I, rtV207M, rtN238, rtN236A/V/S, rtN238H and rtM204A in its DNA polymerase;
 (d) a mutation in the HBV genome resulting in amino acid mutation rtM204A, rtM204I/V and rtN236A/V/S in its DNA polymerase;
 (e) a mutation in the HBV genome resulting in amino acid mutation sC69STOP, sC76STOP, sR79H, sP120T, sL176V, sV194F, sT195M in sW196R and its surface antigen;
(II) code that records said input code; and
(III) a computer readable medium that stores the codes.

In a related aspect, the invention extends to a computer for assessing the likely usefulness of a viral variant or biological sample comprising same in a subject, wherein said computer comprises:

(1) a machine-readable data storage medium comprising a data storage material encoded with machine-readable data, wherein said machine-readable data comprise input codes for at least two features associated with said viral variant or biological sample; wherein said features are selected from:—
 (a) the ability to exhibit resistance for reduced sensitivity to a particular compound or immunological agent;
 (b) an altered DNA polymerase from wild-type HBV;
 (c) an altered surface antigen from wild-type HBV; or
 (d) morbidity or recovery potential of a patient;
(2) a working memory for storing instructions for processing said machine-readable data;
(3) a central-processing unit coupled to said working memory and to said machine-readable data storage medium, for processing said machine readable data to provide a sum of said input code corresponding to a value for said compound(s); and
(4) an output hardware coupled to said central processing unit, for receiving said value.

More particularly, the present invention is directed to a computer for assessing the likely usefulness of a viral variant or biological sample comprising same in a subject, wherein said computer comprises:

(I) code that receives an input code for at least two features associated with said HBV or biological sample comprising same, wherein said features are selected from:
 (a) a mutation in the HBV genome resulting in amino acid mutation rtS85T in its DNA polymerase;
 (b) a mutation in the HBV genome resulting in amino acid mutation rtM204I/V in its DNA polymerase;
 (c) a mutation in the HBV genome resulting in amino acid mutation rtS78T, rtT128N, rtT184G, rtS202I, rtV207M, rtN238, rtN236A/V/S, rtN238H and rtM204A in its DNA polymerase;
 (d) a mutation in the HBV genome resulting in amino acid mutation rtM204A, rtM204I/V and rtN236A/V/S in its DNA polymerase;

(e) a mutation in the HBV genome resulting in amino acid mutation sC69STOP, sC76STOP, sR79H, sP120T, sL176V, sV194F, sT195M in sW196R and its surface antigen;

(II) code that records said input code; and (III) a computer readable medium that stores the codes.

Figure 3:
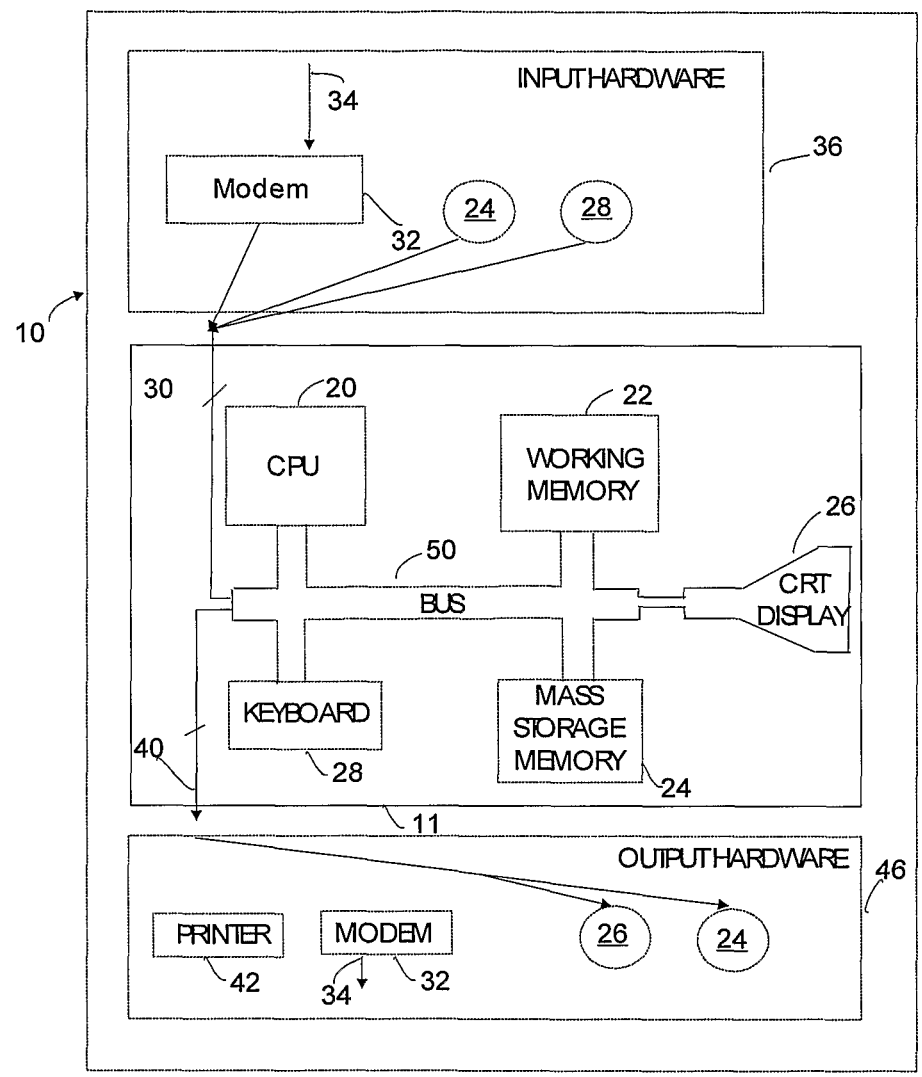
FIG. 3 is a diagrammatic representation of a computer system for determining the potency value ($P_A$) of a variant HBV.

Any general or special purpose computer system is contemplated by the present invention and includes a processor in electrical communication with both a memory and at least one input/output device, such as a terminal. FIG. 3 shows a generally suitable computer system. Such a system may include, but is not limited, to personal computers, workstations or mainframes. The processor may be a general purpose processor or microprocessor or a specialized processor executing programs located in RAM memory. The programs may be placed in RAM from a storage device, such as a disk or pre-programmed ROM memory. The RAM memory in one embodiment is used both for data storage and program execution. The computer system also embraces systems where the processor and memory reside in different physical entities but which are in electrical communication by means of a network.

In an alternative embodiment, the program screens for a mutation selected from, in one embodiment, in one embodiment, rtS78T, rtS85T, rtT128N, rtT184G, rtS202I, rtV207M, rtM204A, rtN236A/V/S, rtN238H or a combination thereof or an equivalent mutation or a combination thereof or an equivalent mutation; in a further embodiment, sC69stop, sC76stop, sR79H, sP120T, sL176V, sV194F, sI195M, sW196R, or a combination thereof or an equivalent mutation.

The present invention is further described by the following non-limiting Examples.

Example 1

Overlapping Genome of HBV

The overlapping genome of HBV is represented in FIG. 1. The gene encoding DNA polymerase (P), overlaps the viral envelope genes, Pre-S1 and Pre-S2, and partially overlaps the X and core (C) genes. The HBV envelope comprises small, middle and large proteins HBV surface antigens. The large protein component is referred to as the HBV surface antigen (HBsAg) and is encoded by the S gene sequence. The Pre-S1 and Pre-S2 gene sequences encode the other envelope components.

Example 2

Patient on ADV and LMV Treatment and Analysis of HBV DNA

Figure 11:
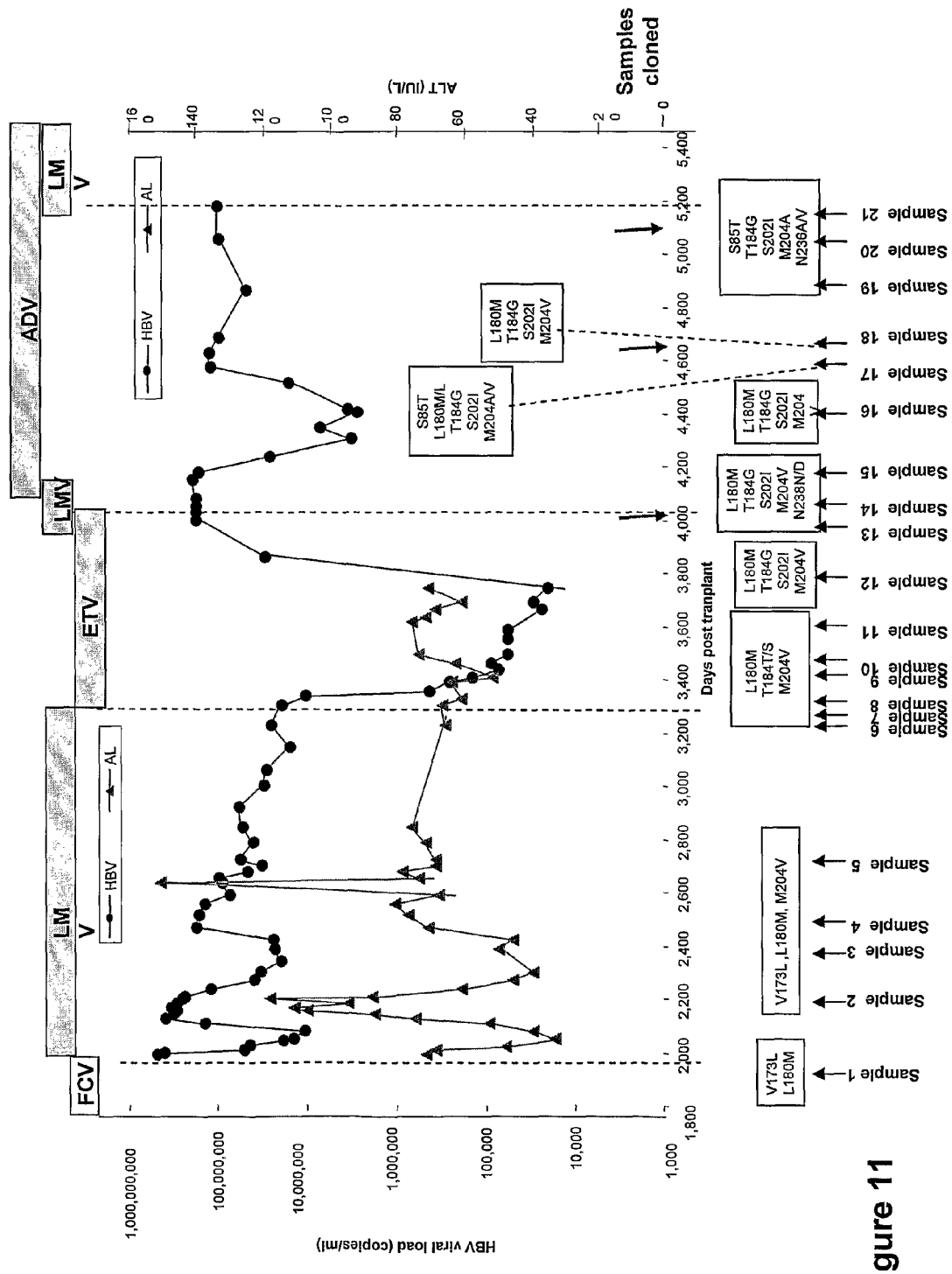
FIG. 11 is a graphical representation showing Days post transplant vs HBV viral load and ALT highlighting antiviral treatment and important antiviral resistance mutations in the polymerase gene at different time points.

This patient had previously been on a number of antiviral agents sequentially and had previously selected HBV with ETV and LMV resistance. The patient's previous clinical history and resistance profile to ETV and LMV was published in Tenney et al, supra and International Patent Application No. PCT/AU03/00111). This patient was subsequently treated with ADV. The patient selected HBV which retained the ETV resistance mutations rtT184G and rtS202I, while on ADV therapy. HBV encoding new mutations corresponding to ADV resistance was selected. The patient selected HBV encoding mutations in the rt region at rtS78T, rtS85T, rtT128N, rtT184G, rtS202I, rtM204A, and rtN236A/V/S during virological failure on ADV treatment (Refer to Table 4 and the sequence information at selected time points is shown in FIGS. 4, to 10, A summary of the polymerase changes are shown in FIG. 11; respectively.

Particularly important mutants are rtS85T, rtM204A, rtN236A/V. The rtN236 A/V/S was detected on cloning see Example 6.

The patient has selected HBV with a new mutation at codon 204 ie., Alanine instead of valine or isoleucine which is usually selected during LMV resistance. In addition, the patient has selected HBV encoding new mutations at codon 85 and 236, ie., rtS85T instead of rtS85A and rtN236A/V/S instead of rtN236T. Neither the alanine, nor the valine, nor the serine deduced amino acid residue have been previously detected in HBV isolated from ADV treated patients at codon 236.

The ADV resistance mutation rtN236T is located not directly in the active site of the polymerase, but near the triphosphate site and is adjacent to and potentially hydrogen bonded to rtS85. The serine 85 directly interacts with gamma-triphosphate of the incoming nucleoside-TP, and thus interacts with the gamma phosphate of ADV-TP. This mutation may indirectly alter the tri-phosphate (TP) binding site of the HBV polymerase and perturb the interaction between the ADV-TP via rtS85. Thus, the new ADV resistance mutations at rtN236A/V/S may also require the rtS85T for a concomitant affect and disruption of the TP-binding site.

In addition, a number of envelope mutations were selected in the S gene include, sC69stop, sC76stop, sR79H, sP120T, sL176V, sV194F, sI195M and sW196R, Example 3

Detection of Viral Markers

Hepatitis B surface antigen (HBsAg), hepatitis B e antigen (HBeAg), anti-HBe and hepatitis B core antigen (HBcAg) specific IgG and IgM were measured using commercially available immunoassays (Abbott Laboratories, North Chicago, Ill., USA). Hepatitis B viral DNA levels were measured using a capture hybridization assay according to the manufacturer's directions (Digene Hybrid Capture II, Digene Diagnostics Inc., Beltsville, Md.). The manufacturers stated cut-off for detecting HBV viremia in clinical specimens was $0.7 \times 10^6$ copies/ml or 2.5 pg/ml, [Hendricks et al, Am J Clin Pathol 104: 537-46, 1995]. HBV DNA levels can also be quantitated using other commercial kits such as Cobas amplification HBV monitor kit (Roche).

Example 4

Sequencing of HBV DNA

HBV DNA was extracted from 100 µl of serum as described previously by Aye et al, J. Hepatol. 26: 1148-1153, 1997. Oligonucleotides were synthesized by Geneworks, Adelaide, Australia. Amplification of the HBV polymerase gene has been described by Aye et al, 1997, supra.

The specific amplified products were purified using PCR purification columns from MO BIO Laboratories Inc (La Jolla, Calif.) and directly sequenced using Big Dye terminator Cycle sequencing Ready Reaction Kit (Perkin Elmer, Cetus Norwalk, Conn.). The PCR primers were used as sequencing primers, OS1 5'-GCC TCA TTT TGT GGG TCA CCA TA-3' (nt 1408-1430) [SEQ ID NO:1], TTA3 5'-AAA TTC GCA GTC CCC AAA-3'(nt2128-2145) [SEQ ID NO:2], JM 5'-TTG GGG TGG AGC CCT CAG GCT-3'

(nt1676-1696) [SEQ ID NO:3], TTA4 5'-GAA AAT TGG TAA CAG CGG-3' (nt 2615-2632) [SEQ ID NO:4], OS2 5' TCT CTG ACA TAC TTT CCA AT 3' (nt 2798-2817) [SEQ ID NO:5], to sequence the internal regions of the PCR products.

Example 5

Clonal Analysis of HBV Isolated at Different Times During ADV Treatment

A 1.2 kb amplified PCR amplified product was cloned into pCRscript as per manufacturers specification. Three time points for cloning are shown on FIG. 11. Thirty to thirty-two clones were sequenced and analysed. A summary of the results of the cloning are shown in Tables 5, 6 and 7. Mutations which are not are not identified through direct sequencing as they represent less than 20% of the total population may be detected by clonal analysis. Table 7 shows that rtN236S was present in 3% of clones.

Example 6

Adefovir Dipivoxil (ADV)

Figure 2:
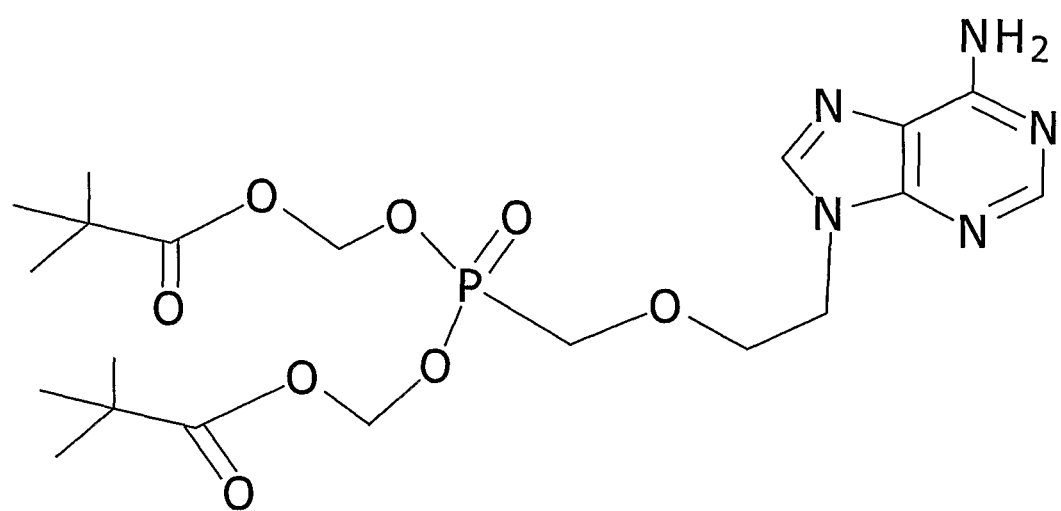
FIG. 2 is a diagrammatic representation of the chemical structure of ADV.

ADV (formerly Bis-pom PMEA)) is a potent inhibitor of HBV replication. The structure of ADV is shown in FIG. 2 and its synthesis is described by Benzaria et al, *J Med Chem.* 39: 4958-4965, 1996).

Example 7

In Vitro Analysis of Adefovir Resistance

The sensitivity/resistance profile of HBV mutants to adefovir may be examined in vitro using recombinant HBV/baculovirus. The procedure for analysing the resistance profile is outlined in the following Examples 8-14.

Example 8

Cell Culture

Sf21 insect cells can be maintained in supplemented Grace's insect medium further supplemented with 10% v/v heat-inactivated fetal bovine serum (Gibco BRL, Gaithersburg, Md.) in humidified incubator at 28 C with $CO_2$. HepG2 cells are maintained in minimal essential medium supplemented with 10% v/v heat-inactivated fetal bovine serum (MEM-FBS). HepG2 cells are grown in humidified 37° C. incubators at 5% v/v $CO_2$.

Example 9

Preparation of HBV/Baculovirus Transfer Vector with Specific Point Mutations The recombinant HBV/baculovirus system used for antiviral testing has been previously described (Delaney et al, *Antimicrob Agents Chemother* 45(6): 1705-1013, 2001). In brief, the recombinant transfer vector was created by excising a fragment containing the 1.3×HBV genome construct and cloning it into the multiple cloning region of a baculovirus vector pBlueBac4.5 (Invitrogen, Carlsbad, Calif.). Point mutations can be created by site directed mutagenesis using the commercial kits according to the manufacturers specifications (QuikChange, Stratagene).

Example 10

The Process for Generation of Recombinant Baculoviruses Containing the 1.3 HBV Construct Purified recombinant transfer vector and linear AcMNPV baculovirus DNA can be co-transfected into Sf21 cells using the BacNBlue transfection kit from Invitrogen (Carlsbad, Calif.); recombinant viruses are isolated by plaque assay according to the manufacturer's instructions. A series of recombinant viruses can be amplified from isolated plaques by infecting 100-mm dishes of Sf21 cells. Viral DNA is extracted from amplified viruses using standard procedures. Purified viral DNA can be digested with restriction enzymes and then fractionated by electrophoresis in a 1% v/v agarose gel. Southern blotting can be performed to determine which virus isolates contain the intact 1.3 HBV construct. A Boehringer Mannheim Random Prime DNA Labeling kit (Indianapolis, Ind.) can be used to generate $[P^{32}]$-radiolabeled probes. A full-length double-stranded HBV genome can be used as a template for all radiolabeled probes. Viral DNA sequence can be confirmed by PCR amplification and sequencing of the polymerase gene

Example 11

Preparative Baculovirus Amplification and Purification

Baculoviruses can be amplified by infecting suspension cultures of Sf21 cells in log phase at a multiplicity of infection (moi) of 0.5 pfu/cell. Infections can be allowed to proceed until a majority of the cells in the flasks showed visible signs of infection (four to five days). Virions are then concentrated from infected Sf21 medium by centrifugation at 80,000×g and purified through a 20-60% w/v sucrose gradient. Purified virus can be titrated in quadruplicate in Sf21 cells by end-point dilution. An aliquot of each high titer stock can be used for DNA extraction. The polymerase gene can be amplified and sequenced to confirm the presence of the site-directed mutagenesis as in Example 8

Example 12

Infection of HepG2 Cells with Recombinant HBV Expressing Baculovirus

HepG2 cells are to be seeded at approximately 20-40% confluency and then grown for 16-24 hours before infection. On the day of infection, triplicate plates of cells are trypsinized, and viable cell number determined with a hemocytometer using Trypan blue exclusion. Average cell counts can be calculated and used to determine the volume of high-titer viral stock necessary to infect cells at the indicated moi. HepG2 cells are washed one time with serum-free MEM to remove traces of serum. Baculovirus is diluted into MEM without serum to achieve the appropriate moi using volumes of 1.0, 0.5, and 0.25 ml to infect 100-mm, 60 mm, and 35-mm dishes, respectively. Baculovirus is adsorbed to HepG2 cells for one hour at 37° C. with gentle rocking every 15 minutes to ensure that the inoculum is evenly distributed. The inoculum was then aspirated and HepG2 cells are washed two times with phosphate-buffered saline and refed MEM-FBS with or without various concentrations of agents.

Example 13

Analysis of Secreted HBV Antigen

Detection of hepatitis Be antigen (HBeAg) can be performed by radioimmunoassay and microparticle enzyme immunoassay using kits purchased from Abbott Laboratories (Abbott Park, Ill., USA). Medium from HepG2 cells is collected, centrifuged at 6,000 g to remove cellular debris, transferred to clean tubes, and stored at 20° C. until analysis. HBeAg values are expressed as fold of positive control. Medium samples are diluted appropriately so that radioimmunoassay results were below positive control values for HBeAg.

Example 14

Detection of Intracellular Replicative Intermediates

HBV core particles are isolated from the cytoplasmic fraction of HepG2 cells lysed in 0.5% w/v NP-40. Cytoplasmic extracts are adjusted to 10 mmol/l McC12 and unprotected DNA is removed by an incubation to 500 g/ml Proteinase K for 1.5 hours at 37° C. HBV DNA in the samples are extracted using commercial DNA extraction kits such as Qiagen (DNA extraction) or in-house methods using sequential phenol and chloroform extractions, and the nucleic acids are recovered by ethanol precipitation. Nucleic acids are resuspended in 50 μl/l TE (10 mmol/l Tris, 1 mmol/l ethylenediaminetetraacetic acid), normalized by OD260, and digested with 100 g/ml RNase (Boehringer Mannheim, Indianapolis, Ind.) for one hour at 37° C. before analysis by real-time PCR or electrophoresis and Southern blotting. After southern blot analysis a BioRad GS-670 imaging densitometer and the Molecular Analyst software (BioRad, Hecules Calif.) can be used to analyze suitable exposures of Southern blots. Densitometry data can be fitted to logistic dose response curves using the TableCurve 2D software package from Jandel Scientific. Logistic dose response equations are used to calculate $IC_{50}$ and $IC_{90}$ values and co-efficients of variation.

Example 15

ADV Treatments

ADV is resuspended in sterile water, aliquoted, and frozen at −20° C. to avoid repeated freezing and thawing of the drug. Medium containing ADV is prepared daily as needed using fresh aliquots of ADV. In experiments in which ADV treatment was initiated after viral infection, HepG2 cells can be exposed to the indicated concentration of ADV immediately after infection with HBV baculovirus. In experiments utilizing pretreatment with ADV, cells are to be fed medium containing ADV 16 hours prior to HBV baculovirus infection, HBV baculovirus infection is also carried out in medium containing ADV, and cells are refed fresh medium containing ADV immediately after completion of the infection and washing procedures.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 4

Patient A HBV Polymerase and envelope mutations detected during LMV and ADV therapy

| Treatment | code | HBV RT Mutations | HBsAg Mutations |
|---|---|---|---|
| LMV and ETV (pre-ADV treatment) | 0254292 Sample 13 | rtT128N, rtL180M, rtT184G, rtS202I, rtM204V, rtN238N/D | sP120T, sL176V, sV194F, sI195M,, |
| ADV treatment | 0279618 Sample 14 | rtT128N, rtL180M, rtT184G, rtS202I, rtM204V, rtN238N/D | sP120T, sL176V, sV194F, sI195M, |
| ADV treatment | 03505860 Sample 15 | rtT128N, rtL180M, rtT184G, rtS202I, rtM204V, rtN238N/D | sP120T, sL176V, sV194F, sI195M, |
| ADV treatment | 03534346 Sample 16 | rtS78T/S, rtT128N, rtL180M, rtT184G, rtS202I, rtM204V, | sC69*/C, sP120T, sL176V, sV194F, sI195M, |
| ADV treatment | 04511239 Sample 17 | rtL42V, rtS78T, rtS85T, rtT128N, rtL180M/L, rtT184G, rtS202I, rtM204A/V | SD33E, sC69*, sC76*, sR79H, sP120T, sL176V, sV194F, sI195M, sW196R/W |
| ADV treatment | 04521126 Sample 18 | rtT128N, rtL180M, rtT184G, rtS202I, rtM204V, | sP120T, sL176V, sV194F, sI195M,, |
| ADV treatment | 04553852 Sample 19 | rtL42V, rtS78T, rtS85T, rtT128N, rtT184G, rtS202I, rtM204A | sD33E, sC69*, sC76*, sR79H, sP120T, sL176V, sV194F, sI195M, sW196R |
| ADV treatment | 05523099 Sample 20 | rtS78T, rtS85T, rtY111H/Y, rtT128N, rtT184G, rtS202I, rtM204A, rtN236A/V, | sC69*, sC76*, sR79H, sL98P/L, sP120T, sL176V, sV194F, sI195M, sW196R |
| ADV treatment | 05538824 Sample 21 | rtS78T, rtS85T, rtT128N, rtT184G, rtS202I, rtM204A, rtN236A/V/S | sC69*, sC76*, sR79H, sP120T, sL176V, sV194F, sI195M, sW196R |

TABLE 5

Cloning of Sample 13 (DIV0702) - ETV breakthrough/pre-ADV

| Polymerase sequence detected by direct sequencing | Sequencing of clones (n = 31) Major clonal species | Minor Clonal species |
|---|---|---|
| rtS78 | rtS78 79% | rtS78T 21% |
| rtT128N | rtT128N 100% | |
| rtI169 | rtI169 79% | rtI169T 21% |
| rtL180M | rtL180M 100% | |
| rtT184G | rtT184G 97% | rtT184C 3% |
| rtS202I | rtS202I 100% | |
| rtM204V | rtM204V | |
| rtN238N/D | rtN238 93% | rtN238D 7% |
| rtI266V | rtI266V 100% | |

7/31 clones had deletions (570 bp up to 1000 bp)

TABLE 6

Cloning of Sample 17 DIV0304 - 8 months on ADV

| Polymerase sequence detected by direct sequencing | Sequencing of clones (n = 30) Major Clonal species | Minor Clonal species |
|---|---|---|
| rtL42V | rtL42V 79% | rtL42 21% |
| rtS78T | rtS78T 100% | |
| rtS85T | rtS85T 94% | rtS85 3% |
| rtT128N | rtT128N 100% | |
| rtI169 | rtI169 100% | rtI169T 0% |
| rtL180M | rtL180M 62% | rtL180 34% |
|  |  | rtL180T 3% |
| rtT184G | rtT184G 100% | |
| rtS202I | rtS202I 100% | |
| rtM204A*/V | rtM204V 66% | rtM204A 33% |
| rtN238 | rtN238 100% | |
| rtI266 | rtI266 100% | rtI266V 0% | rtM204A is not detected with the rtL180M
1/30 clones had deletions (570 upto 1000 bp)

TABLE 7

Cloning of Sample 20 (DIV0505) - on ADV

| Polymerase sequence detected by direct sequencing | Sequencing of clones (n = 32) Major Clonal species | Minor Clonal species |
|---|---|---|
| rtL42 | rtL42 100% | rtL42V 0% |
| rtS78 | rtS78T 100% | |
| rtS85T | rtS85T 100% | |
| rtT128N | rtT128N 100% | |
| rtI169 | rtI169 100% | |
| rtL180 | rtL180 100% | rtL180M 0% |
| rtT184G | rtT184G 97% | rtT184D 3% |
| rtS202I | rtS202I 100% | |
| rtM204A | rtM204A 100% | rtM204V 0% |
| rtV207 | rtV207 80% | rtV207M 20% |
| rtN236A*/V | rtN236A 69% | rtN236V 16% |
|  |  | rtN236 13% |
|  |  | rtN236S 3% |
| rtN238 | rtN238 80% | rtN238H 20% |
| rtI266 | rtI266 100% | rtI266V 0% |

*rtN236V and rtN236S always detected with rtV207M and rtN238H

BIBLIOGRAPHY

Allen et al, *Hepatology* 27(6): 1670-1677, 1998
Angus et al, *Gastroenterology.* 125(2):292-7. 2003
Aye et al, *J. Hepatol.* 26: 1148-1153, 1997
Bartholomeusz et al, *Intervirology* 40(5-6): 337-342 1997
Benhamou et al, *Lancet* 358: 718-723, 2001
Benzaria et al, *J Med Chem.* 39: 4958-4965, 1996
Boyd et al, *Antiviral Chem Chemother.* 32: 358-363, 1987
Calio et al, *Antiviral Res.* 23: 77-89, 1994
Das et al, *J. Virol.* 75(10): 4771-4779, 2001
Dienstag et al, *New England J Med* 333: 1657-1661, 1995
Frick et al, *Antimicrob. Agents Chemother.* 37: 2285-2292, 1993
Gaillard et al, *Antimicrob Agents Chemother.* 46(4): 1005-1013, 2002
Gilson et al, *J Viral Hepat* 6: 387-395, 1999
Heathcote et al, *Hepatology* 28: A620, 1998
Hendricks et al, *Am J Clin Pathol* 104: 537-46, 1995
Kruger et al, *Hepatology* 22: 219A, 1994
Main et al, *J. Viral Hepatitis* 3: 211-215, 1996
Norder et al, (*J. Gen. Virol.* 74: 341-1348, 1993
Perrillo et al, *Hepatology* 32: 129-134, 2000
Peters et al, *Transplantation* 68: 1912-1914, 1999
Price et al, *Proc. Natl. Acad. Sci. USA* 86(21): 8541-8544, 1989
Ren and Nassal, *J. Virol.* 75(3): 1104-1116, 2001
Severini et al, *Antimicrobial Agents Chemother.* 39: 430-435, 1995
Stuyver et al, *Hepatology* 33: 751-757, 2001
Summers and Mason, *Cell* 29: 403-415, 1982
Suo et al, *J Biol Chem.* 273(42): 27250-27258. 1998
Tenney et al, *Antimicrob Agents Chemother.* 48(9):3498-507. 2004
Vere Hodge, *Antiviral Chem Chemother* 4: 67-84, 1993
Xiong et al, *Hepatology.* 28(6): 1669-73, 1998
Ying et al, *J Viral Hepat.* 7(2): 161-165, 2000

The invention claimed is:

1. A method of detecting an Hepatitis B Virus (HBV) variant from an HBV isolate, said method comprising:
   isolating the DNA genome or the corresponding mRNA genome from said HBV isolate;
   amplifying a portion of the genome, or cDNA from the mRNA, with one or more biotin-labeled or ligand-labeled primers that selectively bind to a portion of the HBV reverse transcriptase (rt) gene which codes for a threonine (T) at rt85 and an alanine (A), an isoleucine (I) or a valine (V) at rt204,
   creating labeled amplification products, wherein the one or more primers do not bind to the portion of the HBV rt gene if the HBV rt gene does not encode for the combination of the T at rt85 and the A, the I or the V at rt204,
   capturing the labeled amplification products by hybridization with an oligonucleotide that binds to the biotin or to the ligand, wherein the oligonucleotide is immobilized on a solid support,
   sequencing the amplification products,
   and determining whether or not the HBV isolate included a T at rt85 and an A, I, or V at rt 204.

2. The method of claim 1, further comprising amplifying a portion of the genome, or cDNA from the mRNA, with one or more biotin-labeled or ligand-labeled primers that selectively bind to a portion of the HBV reverse transcriptase (rt) gene which codes for an amino acid selected from the group consisting of alanine (A), valine (V) and serine (S) at position rt236, creating labeled amplification products,
   wherein the one or more primers do not bind to the portion of the HBV rt gene if the HBV rt gene does not encode for an A, V or S at position rt236,
   capturing the labeled amplification products by hybridization with an oligonucleotide that binds to the biotin or to the ligand, wherein the oligonucleotide is immobilized on a solid support, and
   sequencing the amplification products, and determining whether or not the HBV isolate included a A, V, or S at rt 236.

3. A method for treating a patient infected with an HBV variant with reduced sensitivity to ADV, said method comprising:
   obtaining a sample of HBV isolate from a patient infected with an HBV,
   isolating the DNA genuine or the corresponding mRNA genome from said HBV,
   amplifying a portion of the genome, or cDNA from the mRNA, with one or more biotin-labeled or ligand-labeled primers that selectively bind to a portion of the HBV rt gene which codes for a T at rt85 and an A, an I or a V at rt204,
   creating labeled amplification products, wherein the one or more primers do not, bind to the portion of the HBV rt gene if the HBV rt gene does not encode for a the combination of the T at rt85 and the A, the I or the V at rt204,
   capturing the labeled amplification products by hybridization with an oligonucleotide that binds to the biotin or to the ligand, wherein the oligonucleotide is immobilized on a solid support,
   sequencing the amplification products,
   wherein the presence of the DNA or the mRNA which encodes for the combination of the T at position 85 and the A or the I or the V at position 204 in the amplification product, identifies the HBV variant as one with reduced sensitivity to ADV, and
   if the patient is infected with the HBV variant with reduced sensitivity to ADV, treating the patient with an anti-HBV agent selected from the group consisting of Penciclovir, FCV, 3TC, Emtricitabine (FTC), Clevudine, L-FMAU, Entecavir (ETV), DAPD, DXG, FLG, L-d4C, ICN, Racivir, tenofovir disoproxil fumarate (TDF), tenofovir (TFV), 9-R-(2-phosphonomethoxypropyl)adenine (PMPA), interferon, hepatitis B immunoglobulin (HBIG), and combinations thereof.

4. The method of claim 3, further comprising amplifying a portion of the genome, or cDNA from the mRNA, with one or more biotin-labeled or ligand-labeled primers that selectively bind to a portion of the HBV reverse transcriptase (rt) gene which codes for an amino acid selected from the group consisting of alanine (A), valine (V) and serine (S) at position rt236,
   creating labeled amplification products, wherein the one or more primers do not bind to the portion of the HBV rt gene if the HBV rt gene does not encode for an A, V, or S at position rt236,
   capturing the labeled amplification products by hybridization with an oligonucleotide that binds to the biotin or to the ligand, wherein the oligonucleotide is immobilized on a solid support,
   sequencing the amplification products, wherein the presence of DNA or mRNA which encodes for an A, V, or S at position rt236 in the amplification product identifies the HBV variant as one with reduced sensitivity to ADV, and if the patient is infected with an HBV variant with reduced sensitivity to ADV, treating the patient with an anti-HBV agent selected from the group consisting of Penciclovir, FCV, 3TC, Emtricitabine (FTC), Clevudine, L-FMAU, Entecavir (ETV), DAPD, DXG, FLG, L-d4C, ICN, Racivir, tenofovir disoproxil fumarate (TDF), tenofovir (TFV), 9-R-(2-phosphonomethoxypropyl)adenine (PMPA), interferon, hepatitis B immunoglobulin (HBIG), and combinations thereof.

*

SEQUENCE LISTING

<160> NUMBER OF SEQ ID NOS: 26

<210> SEQ ID NO 1
<211> LENGTH: 23
<212> TYPE: DNA
<213> ORGANISM: Hep B virus

<400> SEQUENCE: 1
gcctcatttt gtgggtcacc ata                23

<210> SEQ ID NO 2

```
<211> LENGTH: 18
<212> TYPE: DNA
<213> ORGANISM: Hep B virus

<400> SEQUENCE: 2
aaattcgcag tccccaaa                                                   18

<210> SEQ ID NO 3
<211> LENGTH: 18
<212> TYPE: DNA
<213> ORGANISM: Hep B virus

<400> SEQUENCE: 3
gggtggagcc ctcaggct                                                   18

<210> SEQ ID NO 4
<211> LENGTH: 18
<212> TYPE: DNA
<213> ORGANISM: Hep B virus

<400> SEQUENCE: 4
gaaaattggt aacagcgg                                                   18

<210> SEQ ID NO 5
<211> LENGTH: 20
<212> TYPE: DNA
<213> ORGANISM: Hep B virus

<400> SEQUENCE: 5
tctctgacat actttccaat                                                 20

<210> SEQ ID NO 6
<211> LENGTH: 1014
<212> TYPE: DNA
<213> ORGANISM: Hep B virus

<400> SEQUENCE: 6
aagccgcctc ctgcctccac caatcgccag tcaggacggc agcctacccc gctgtctcca     60
cctttgagag acactcatcc tcaggcgcag tggaaaccca caaccttcca ccaaactctg    120
caagctccac ctgctggtgg ctccagttcc ggaacagtaa accctgttcc gactactgcc    180
tctcacatat cgtcaatctt ctcgaggatt ggggaccctg cgctgaatat ggagaacatc    240
acatcaggat tcctaggacc ccttctcgtg ttacaggcgg ggtttttctt gttgacaaga    300
atcctcacaa taccgaagag tctagactcg tggtggactt ctctcaattt tctagggggga    360 accaccgtgt gtcttggcca aaattcgcag tccccaacct ccaatcactc accaacctcc    420
tgtcctccga cttgtcctgg ttatcgctgg atgtgtctgc ggcgttttat catattcctc    480
ttcatcctgc tgctatgcct catcttcttg ttggttcttc tggactatca aggtatgttg    540
cccgtttgtc ctctaattcc aggatcctca accaccagca cgggaacatg ccgaacttgc    600
acgactcctg ctcaaggaac ctctatgtat cccctcctgtt gctgtaccaa accttcggac    660
ggaaattgca cctgtattcc catcccatca tcctgggctt tcggaaaatt cctatgggag    720
tgggcctcag cccgtttctc atggctcagt ttggtagtgc catttgttca gtggttcgta    780
gggctttccc ccactgtttg gctttcattt atgtggatga tgtggtattg ggggccaagt    840
ctgtacagca tcttgagtcc ctttttaccg ctgttaccaa ttttcttttg tctctgggta    900
tacatttgaa ccctracaaa acaaagagat ggggttactc cctaaatttt atgggctatg    960
tcattggawg ttatgggtcc ttgccacaag aacacatcgt acataaaatc aaag         1014
```

<210> SEQ ID NO 7
<211> LENGTH: 337
<212> TYPE: PRT
<213> ORGANISM: Hep B virus
<220> FEATURE:
<221> NAME/KEY: MISC_FEATURE
<222> LOCATION: (305)..(305)
<223> OTHER INFORMATION: "n" = any nucleotide
<220> FEATURE:
<221> NAME/KEY: MISC_FEATURE
<222> LOCATION: (305)..(305)
<223> OTHER INFORMATION: "n" = any amino acid
<220> FEATURE:
<221> NAME/KEY: MISC_FEATURE
<222> LOCATION: (323)..(323)
<223> OTHER INFORMATION: "n" = any nucleotide

<400> SEQUENCE: 7

Ala Ala Ser Cys Leu His Gln Ser Pro Val Arg Thr Ala Ala Tyr Pro
1               5                   10                  15

Ala Val Ser Thr Phe Glu Arg His Ser Ser Gly Ala Val Glu Thr
            20                  25                  30

His Asn Leu Pro Pro Asn Ser Ala Ser Ser Thr Cys Trp Trp Leu Gln
            35                  40                  45

Phe Arg Asn Ser Lys Pro Cys Ser Asp Tyr Cys Leu Ser His Ile Val
        50                  55                  60

Asn Leu Leu Glu Asp Trp Gly Pro Cys Ala Glu Tyr Gly Glu His His
65                  70                  75                  80

Ile Arg Ile Pro Arg Thr Pro Ser Arg Val Thr Gly Gly Val Phe Leu
                85                  90                  95

Val Asp Lys Asn Pro His Asn Thr Glu Glu Ser Arg Leu Val Val Asp
            100                 105                 110

Phe Ser Gln Phe Ser Arg Gly Asn His Arg Val Ser Trp Pro Lys Phe
        115                 120                 125

Ala Val Pro Asn Leu Gln Ser Leu Thr Asn Leu Leu Ser Ser Asp Leu
    130                 135                 140

Ser Trp Leu Ser Leu Asp Val Ser Ala Ala Phe Tyr His Ile Pro Leu
145                 150                 155                 160

His Pro Ala Ala Met Pro His Leu Leu Val Gly Ser Ser Gly Leu Ser
                165                 170                 175

Arg Tyr Val Ala Arg Leu Ser Ser Asn Ser Arg Ile Leu Asn His Gln
            180                 185                 190

His Gly Asn Met Pro Asn Leu His Asp Ser Cys Ser Arg Asn Leu Tyr
        195                 200                 205

Val Ser Leu Leu Leu Leu Tyr Gln Thr Phe Gly Arg Lys Leu His Leu
    210                 215                 220

Tyr Ser His Pro Ile Ile Leu Gly Phe Arg Lys Ile Pro Met Gly Val
225                 230                 235                 240

Gly Leu Ser Pro Phe Leu Met Ala Gln Phe Gly Ser Ala Ile Cys Ser
                245                 250                 255

Val Val Arg Arg Ala Phe Pro His Cys Leu Ala Phe Ile Tyr Val Asp
            260                 265                 270

Asp Val Val Leu Gly Ala Lys Ser Val Gln His Leu Glu Ser Leu Phe
        275                 280                 285

Thr Ala Val Thr Asn Phe Leu Leu Ser Leu Gly Ile His Leu Asn Pro
    290                 295                 300

Xaa Lys Thr Lys Arg Trp Gly Tyr Ser Leu Asn Phe Met Gly Tyr Val

```
            305                 310                 315                 320
Ile Gly Xaa Tyr Gly Ser Leu Pro Gln Glu His Ile Val His Lys Ile
                325                 330                 335

Lys

<210> SEQ ID NO 8
<211> LENGTH: 302
<212> TYPE: PRT
<213> ORGANISM: Hep B virus

<400> SEQUENCE: 8

Lys Pro Pro Pro Ala Ser Thr Asn Arg Gln Ser Gly Arg Gln Pro Thr
1               5                   10                  15

Pro Leu Ser Pro Pro Leu Arg Asp Thr His Pro Gln Ala Gln Trp Lys
            20                  25                  30

Pro Thr Thr Phe His Gln Thr Leu Gln Ala Pro Pro Ala Gly Gly Ser
        35                  40                  45

Ser Ser Gly Thr Val Asn Pro Val Pro Thr Thr Ala Ser His Ile Ser
    50                  55                  60

Ser Ile Phe Ser Arg Ile Gly Asp Pro Ala Leu Asn Met Glu Asn Ile
65                  70                  75                  80

Thr Ser Gly Phe Leu Gly Pro Leu Leu Val Leu Gln Ala Gly Phe Phe
                85                  90                  95

Leu Leu Thr Arg Ile Leu Thr Ile Pro Lys Ser Leu Asp Ser Trp Trp
            100                 105                 110

Thr Ser Leu Asn Phe Leu Gly Gly Thr Thr Val Cys Leu Gly Gln Asn
        115                 120                 125

Ser Gln Ser Pro Thr Ser Asn His Ser Pro Thr Ser Cys Pro Pro Thr
    130                 135                 140

Cys Pro Gly Tyr Arg Trp Met Cys Leu Arg Arg Phe Ile Ile Phe Leu
145                 150                 155                 160

Phe Ile Leu Leu Leu Cys Leu Ile Phe Leu Leu Val Leu Leu Asp Tyr
                165                 170                 175

Gln Gly Met Leu Pro Val Cys Pro Leu Ile Pro Gly Ser Ser Thr Thr
            180                 185                 190

Ser Thr Gly Thr Cys Arg Thr Cys Thr Thr Pro Ala Gln Gly Thr Ser
        195                 200                 205

Met Tyr Pro Ser Cys Cys Cys Thr Lys Pro Ser Asp Gly Asn Cys Thr
    210                 215                 220

Cys Ile Pro Ile Pro Ser Ser Trp Ala Phe Gly Lys Phe Leu Trp Glu
225                 230                 235                 240

Trp Ala Ser Ala Arg Phe Ser Trp Leu Ser Leu Val Val Pro Phe Val
                245                 250                 255

Gln Trp Phe Val Gly Leu Ser Pro Thr Val Trp Leu Ser Phe Met Trp
            260                 265                 270

Met Met Trp Tyr Trp Gly Pro Ser Leu Tyr Ser Ile Leu Ser Pro Phe
        275                 280                 285

Leu Pro Leu Leu Pro Ile Phe Phe Cys Leu Trp Val Tyr Ile
    290                 295                 300

<210> SEQ ID NO 9
<211> LENGTH: 1013
<212> TYPE: DNA
<213> ORGANISM: Hep B virus

<400> SEQUENCE: 9
```

-continued

```
aagccgcctc ctgcctccac caatcgccag tcaggacggc agcctacccc sctktctcca      60
ccttgagag acactcatcc tcaggcgcag tggaaaccca caaccttcca ccaaactctg      120
caagctccac ctgctggtgg ctccagttcc ggaacagtaa accctgttcc gactactgcc     180
tctcacatat cgtcaatctt ctcgaggatt ggggaccctg cgctgaatat ggagaacatc     240
acatcaggat tcctaggacc ccttctcgtg ttacaggcgg ggttttcctt gttgacaaga     300
atcctcacaa taccgaagag tctagactcg tggtggactt ctctcaattt ctaggggga     360
accaccgtgt gtcttggcca aaattcgcag tccccaacct ccaatcactc accaacctcc     420
tgtcctccga cttgtcctgg ttatcgctgg atgtgtctgc ggcgttttat catattcctc     480
ttcatcctgc tgctatgcct catcttcttg ttggttcttc tggactatca aggtatgttg     540
cccgtttgtc ctctaattcc aggatcctca accaccagca cgggaacatg ccgaacttgc     600
acgactcctg ctcaaggaac ctctatgtat ccctcctgtt gctgtaccaa accttcggac     660
ggaaattgca cctgtattcc catcccatca tcctgggctt tcggaaaatt cctatgggag     720
tgggcctcag cccgtttctc atggctcagt ttggtagtgc catttgttca gtggttcgta     780
gggctttccc ccactgtttg ctttcattt atgtggatga tgtggtattg ggggccaagt     840
ctgtacagca tcttgagtcc cttttttaccg ctgttaccaa ttttcttttg tctctgggta     900
tacatttgaa ccctracaaa acaaagagat ggggttactc cctaaatttt atgggctatg     960
tcattggawg ttatgggtcc ttgccacaag aacacatcgt acataaaatc aaa           1013
```

<210> SEQ ID NO 10
<211> LENGTH: 337
<212> TYPE: PRT
<213> ORGANISM: Hep B virus
<220> FEATURE:
<221> NAME/KEY: MISC_FEATURE
<222> LOCATION: (17)..(17)
<223> OTHER INFORMATION: "n" = any nucleotide
<220> FEATURE:
<221> NAME/KEY: MISC_FEATURE
<222> LOCATION: (18)..(18)
<223> OTHER INFORMATION: "n" = any nucleotide
<220> FEATURE:
<221> NAME/KEY: MISC_FEATURE
<222> LOCATION: (305)..(305)
<223> OTHER INFORMATION: "n" = any nucleotide
<220> FEATURE:
<221> NAME/KEY: MISC_FEATURE
<222> LOCATION: (323)..(323)
<223> OTHER INFORMATION: "n" = any nucleotide
<220> FEATURE:
<221> NAME/KEY: MISC_FEATURE
<222> LOCATION: (323)..(323)
<223> OTHER INFORMATION: "n" = any amino acid

<400> SEQUENCE: 10

```
Ala Ala Ser Cys Leu His Gln Ser Pro Val Arg Thr Ala Ala Tyr Pro
1               5                   10                  15

Xaa Xaa Ser Thr Phe Glu Arg His Ser Ser Ser Gly Ala Val Glu Thr
            20                  25                  30

His Asn Leu Pro Pro Asn Ser Ala Ser Ser Thr Cys Trp Trp Leu Gln
        35                  40                  45

Phe Arg Asn Ser Lys Pro Cys Ser Asp Tyr Cys Leu Ser His Ile Val
    50                  55                  60

Asn Leu Leu Glu Asp Trp Gly Pro Cys Ala Glu Tyr Gly Glu His His
65                  70                  75                  80

Ile Arg Ile Pro Arg Thr Pro Ser Arg Val Thr Gly Gly Val Phe Leu
```

```
            85              90              95
Val Asp Lys Asn Pro His Asn Thr Glu Glu Ser Arg Leu Val Val Asp
            100             105             110
Phe Ser Gln Phe Ser Arg Gly Asn His Arg Val Ser Trp Pro Lys Phe
            115             120             125
Ala Val Pro Asn Leu Gln Ser Leu Thr Asn Leu Leu Ser Ser Asp Leu
130             135             140
Ser Trp Leu Ser Leu Asp Val Ser Ala Ala Phe Tyr His Ile Pro Leu
145             150             155             160
His Pro Ala Ala Met Pro His Leu Leu Val Gly Ser Ser Gly Leu Ser
                165             170             175
Arg Tyr Val Ala Arg Leu Ser Ser Asn Ser Arg Ile Leu Asn His Gln
            180             185             190
His Gly Asn Met Pro Asn Leu His Asp Ser Cys Ser Arg Asn Leu Tyr
            195             200             205
Val Ser Leu Leu Leu Leu Tyr Gln Thr Phe Gly Arg Lys Leu His Leu
210             215             220
Tyr Ser His Pro Ile Ile Leu Gly Phe Arg Lys Ile Pro Met Gly Val
225             230             235             240
Gly Leu Ser Pro Phe Leu Met Ala Gln Phe Gly Ser Ala Ile Cys Ser
                245             250             255
Val Val Arg Arg Ala Phe Pro His Cys Leu Ala Phe Ile Tyr Val Asp
            260             265             270
Asp Val Val Leu Gly Ala Lys Ser Val Gln His Leu Glu Ser Leu Phe
            275             280             285
Thr Ala Val Thr Asn Phe Leu Leu Ser Leu Gly Ile His Leu Asn Pro
290             295             300
Xaa Lys Thr Lys Arg Trp Gly Tyr Ser Leu Asn Phe Met Gly Tyr Val
305             310             315             320
Ile Gly Xaa Tyr Gly Ser Leu Pro Gln Glu His Ile Val His Lys Ile
                325             330             335
Lys

<210> SEQ ID NO 11
<211> LENGTH: 302
<212> TYPE: PRT
<213> ORGANISM: Hep B virus

<400> SEQUENCE: 11

Lys Pro Pro Pro Ala Ser Thr Asn Arg Gln Ser Gly Arg Gln Pro Thr
1               5               10              15
Pro Leu Ser Pro Pro Leu Arg Asp Thr His Pro Gln Ala Gln Trp Lys
            20              25              30
Pro Thr Thr Phe His Gln Thr Leu Gln Ala Pro Pro Ala Gly Gly Ser
            35              40              45
Ser Ser Gly Thr Val Asn Pro Val Pro Thr Thr Ala Ser His Ile Ser
        50              55              60
Ser Ile Phe Ser Arg Ile Gly Asp Pro Ala Leu Asn Met Glu Asn Ile
65              70              75              80
Thr Ser Gly Phe Leu Gly Pro Leu Leu Val Leu Gln Ala Gly Phe Phe
                85              90              95
Leu Leu Thr Arg Ile Leu Thr Ile Pro Lys Ser Leu Asp Ser Trp Trp
            100             105             110
Thr Ser Leu Asn Phe Leu Gly Gly Thr Thr Val Cys Leu Gly Gln Asn
```

```
                115                 120                 125
Ser Gln Ser Pro Thr Ser Asn His Ser Pro Thr Ser Cys Pro Pro Thr
    130                 135                 140

Cys Pro Gly Tyr Arg Trp Met Cys Leu Arg Arg Phe Ile Ile Phe Leu
145                 150                 155                 160

Phe Ile Leu Leu Leu Cys Leu Ile Phe Leu Val Leu Leu Asp Tyr
                165                 170                 175

Gln Gly Met Leu Pro Val Cys Pro Leu Ile Pro Gly Ser Ser Thr Thr
            180                 185                 190

Ser Thr Gly Thr Cys Arg Thr Cys Thr Thr Pro Ala Gln Gly Thr Ser
        195                 200                 205

Met Tyr Pro Ser Cys Cys Thr Lys Pro Ser Asp Gly Asn Cys Thr
    210                 215                 220

Cys Ile Pro Ile Pro Ser Ser Trp Ala Phe Gly Lys Phe Leu Trp Glu
225                 230                 235                 240

Trp Ala Ser Ala Arg Phe Ser Trp Leu Ser Leu Val Val Pro Phe Val
                245                 250                 255

Gln Trp Phe Val Gly Leu Ser Pro Thr Val Trp Leu Ser Phe Met Trp
            260                 265                 270

Met Met Trp Tyr Trp Gly Pro Ser Leu Tyr Ser Ile Leu Ser Pro Phe
        275                 280                 285

Leu Pro Leu Leu Pro Ile Phe Phe Cys Leu Trp Val Tyr Ile
    290                 295                 300

<210> SEQ ID NO 12
<211> LENGTH: 1015
<212> TYPE: DNA
<213> ORGANISM: Hep B virus

<400> SEQUENCE: 12
agccgcctcc tgcctccacc aatcgccagt caggacggca gcctacccg  ctgtctccac      60 ctttgagaga cactcatcct caggcgcagt ggaaacccac aaccttccac caaactctgc     120
aagctccacc tgctggtggc tccagttccg gaacagtaaa ccctgttccg actactgcct     180
ctcacatatc gtcaatcttc tcgaggattg gggaccctgc gctgaatatg agaacatca     240 catcaggatt cctaggaccc cttctcgtgt tacaggcggg ttttttcttg ttgacaagaa     300
tcctcacaat accgaagagt ctagactcgt ggtggacttc tctcaatttt ctaggggga     360 ccaccgtgtg tcttggccaa aattcgcagt ccccaacctc caatcactca ccaacctcct     420
gtcctccgac ttgwcctggt tatcgctgga tgtgtctgcg gcgttttatc atattcctct     480
tcatcctgct gctatgcctc atcttcttgt tggttcttct ggactatcaa ggtatgttgc     540
ccgtttgtcc tctaattcca ggatcctcaa ccaccagcac gggaacatgc cgaacttgca     600
cgactcctgc tcaaggaacc tctatgtatc cctcctgttg ctgtaccaaa ccttcggacg     660
gaaattgcac ctgtattccc atcccatcat cctgggcttt cggaaaattc ctatgggagt     720
gggcctcagc ccgtttctca tggctcagtt tggtagtgcc atttgttcag tggttcgtag     780
ggctttcccc cactgtttgg ctttcattta tgtggatgat gtggtattgg gggccaagtc     840
tgtacagcat cttgagtccc tttttaccgc tgttaccaat tttcttttgt ctctgggtat     900
acatttgaac cctaacaaaa caagagatg gggttactcc ctaaatttta tgggctatgt     960
cattggawgt tatgggtcct tgccacaaga acacatcgta cataaaatca agaa         1015

<210> SEQ ID NO 13
```

```
<211> LENGTH: 338
<212> TYPE: PRT
<213> ORGANISM: Hep B virus
<220> FEATURE:
<221> NAME/KEY: MISC_FEATURE
<222> LOCATION: (145)..(145)
<223> OTHER INFORMATION: "n" = any nucleotide
<220> FEATURE:
<221> NAME/KEY: MISC_FEATURE
<222> LOCATION: (323)..(323)
<223> OTHER INFORMATION: "n" = any nucleotide
<220> FEATURE:
<221> NAME/KEY: MISC_FEATURE
<222> LOCATION: (323)..(323)
<223> OTHER INFORMATION: "n" = any amino acid

<400> SEQUENCE: 13
```

Ala Ala Ser Cys Leu His Gln Ser Pro Val Arg Thr Ala Ala Tyr Pro
1               5                   10                  15

Ala Val Ser Thr Phe Glu Arg His Ser Ser Gly Ala Val Glu Thr
            20                  25                  30

His Asn Leu Pro Pro Asn Ser Ala Ser Ser Thr Cys Trp Trp Leu Gln
            35                  40                  45

Phe Arg Asn Ser Lys Pro Cys Ser Asp Tyr Cys Leu Ser His Ile Val
50                  55                  60

Asn Leu Leu Glu Asp Trp Gly Pro Cys Ala Glu Tyr Gly Glu His His
65                  70                  75                  80

Ile Arg Ile Pro Arg Thr Pro Ser Arg Val Thr Gly Gly Val Phe Leu
                85                  90                  95

Val Asp Lys Asn Pro His Asn Thr Glu Glu Ser Arg Leu Val Val Asp
            100                 105                 110

Phe Ser Gln Phe Ser Arg Gly Asn His Arg Val Ser Trp Pro Lys Phe
        115                 120                 125

Ala Val Pro Asn Leu Gln Ser Leu Thr Asn Leu Leu Ser Ser Asp Leu
    130                 135                 140

Xaa Trp Leu Ser Leu Asp Val Ser Ala Ala Phe Tyr His Ile Pro Leu
145                 150                 155                 160

His Pro Ala Ala Met Pro His Leu Leu Val Gly Ser Ser Gly Leu Ser
                165                 170                 175

Arg Tyr Val Ala Arg Leu Ser Ser Asn Ser Arg Ile Leu Asn His Gln
            180                 185                 190

His Gly Asn Met Pro Asn Leu His Asp Ser Cys Ser Arg Asn Leu Tyr
        195                 200                 205

Val Ser Leu Leu Leu Leu Tyr Gln Thr Phe Gly Arg Lys Leu His Leu
    210                 215                 220

Tyr Ser His Pro Ile Ile Leu Gly Phe Arg Lys Ile Pro Met Gly Val
225                 230                 235                 240

Gly Leu Ser Pro Phe Leu Met Ala Gln Phe Gly Ser Ala Ile Cys Ser
                245                 250                 255

Val Val Arg Arg Ala Phe Pro His Cys Leu Ala Phe Ile Tyr Val Asp
            260                 265                 270

Asp Val Val Leu Gly Ala Lys Ser Val Gln His Leu Glu Ser Leu Phe
        275                 280                 285

Thr Ala Val Thr Asn Phe Leu Leu Ser Leu Gly Ile His Leu Asn Pro
    290                 295                 300

Asn Lys Thr Lys Arg Trp Gly Tyr Ser Leu Asn Phe Met Gly Tyr Val
305                 310                 315                 320

Ile Gly Xaa Tyr Gly Ser Leu Pro Gln Glu His Ile Val His Lys Ile

```
                    325                 330                 335

Lys Glu

<210> SEQ ID NO 14
<211> LENGTH: 301
<212> TYPE: PRT
<213> ORGANISM: Hep B virus
<220> FEATURE:
<221> NAME/KEY: MISC_FEATURE
<222> LOCATION: (144)..(144)
<223> OTHER INFORMATION: "n" = any nucleotide
<220> FEATURE:
<221> NAME/KEY: MISC_FEATURE
<222> LOCATION: (144)..(144)
<223> OTHER INFORMATION: "n" = any amino acid

<400> SEQUENCE: 14

Pro Pro Pro Ala Ser Thr Asn Arg Gln Ser Gly Arg Gln Pro Thr Pro
1               5                   10                  15

Leu Ser Pro Pro Leu Arg Asp Thr His Pro Gln Ala Gln Trp Lys Pro
            20                  25                  30

Thr Thr Phe His Gln Thr Leu Gln Ala Pro Pro Ala Gly Gly Ser Ser
        35                  40                  45

Ser Gly Thr Val Asn Pro Val Pro Thr Thr Ala Ser His Ile Ser Ser
    50                  55                  60

Ile Phe Ser Arg Ile Gly Asp Pro Ala Leu Asn Met Glu Asn Ile Thr
65              70                  75                  80

Ser Gly Phe Leu Gly Pro Leu Leu Val Leu Gln Ala Gly Phe Phe Leu
            85                  90                  95

Leu Thr Arg Ile Leu Thr Ile Pro Lys Ser Leu Asp Ser Trp Trp Thr
            100                 105                 110

Ser Leu Asn Phe Leu Gly Gly Thr Thr Val Cys Leu Gly Gln Asn Ser
        115                 120                 125

Gln Ser Pro Thr Ser Asn His Ser Pro Thr Ser Cys Pro Pro Thr Xaa
    130                 135                 140

Pro Gly Tyr Arg Trp Met Cys Leu Arg Arg Phe Ile Ile Phe Leu Phe
145             150                 155                 160

Ile Leu Leu Leu Cys Leu Ile Phe Leu Leu Val Leu Leu Asp Tyr Gln
            165                 170                 175

Gly Met Leu Pro Val Cys Pro Leu Ile Pro Gly Ser Ser Thr Thr Ser
            180                 185                 190

Thr Gly Thr Cys Arg Thr Cys Thr Thr Pro Ala Gln Gly Thr Ser Met
        195                 200                 205

Tyr Pro Ser Cys Cys Cys Thr Lys Pro Ser Asp Gly Asn Cys Thr Cys
    210                 215                 220

Ile Pro Ile Pro Ser Ser Trp Ala Phe Gly Lys Phe Leu Trp Glu Trp
225             230                 235                 240

Ala Ser Ala Arg Phe Ser Trp Leu Ser Leu Val Val Pro Phe Val Gln
            245                 250                 255

Trp Phe Val Gly Leu Ser Pro Thr Val Trp Leu Ser Phe Met Trp Met
            260                 265                 270

Met Trp Tyr Trp Gly Pro Ser Leu Tyr Ser Ile Leu Ser Pro Phe Leu
        275                 280                 285

Pro Leu Leu Pro Ile Phe Phe Cys Leu Trp Val Tyr Ile
    290                 295                 300

<210> SEQ ID NO 15
```

<211> LENGTH: 934
<212> TYPE: DNA
<213> ORGANISM: Hep B virus

<400> SEQUENCE: 15

```
cccctgctg gtggctccag ttccggaaca gtaaaccctg ttccgactac tgcctctcac    60
atatcgtcaa tcttctcgag gattggggac cctgcgctga atatggagaa catcacatca   120
ggattcctag gacccttcct cgtgttacag gcggggtttt tcttgttgac aagaatcctc   180
acaataccgc agagtctaga gtcgtggtgg acttctctca attttctagg ggsaaccacc   240
gtgtgtcttg gccaaaattc gcagtcccca acctccaatc actccaccaac ctcctgtcct   300
ccgacttgac ctggttatcg ctggatgtga ctgcggcatt ttatcatatt cctcttcatc   360
ctgctgctat gcctcatctt cttgttggtt cttctggact atcaaggtat gttgcccgtt   420
tgtcctctaa ttccaggatc ctcaaccacc agcacgggaa catgccgaac ttgcacgact   480
cctgctcaag gaacctctat gtatccctcc tgttgctgta ccaaaccttc ggacggaaat   540
tgcacctgta ttcccatccc atcatcctgg gctttcggaa aattcctatg ggagtgggcc   600
tcagcccgtt tctcmtggct cagtttggta gtgccatttg ttcagtggtt cgtagggctt   660
tcccccactg ttttggcttt catttatgygg atgatrtggt attgggggcc aagtctgtac   720
agcatcttga gtcccttttt accgctgtta ccaatttttct tttgtctctg ggtatacatt   780
tgaacctaa caaaacaaag atgggggtt actccctaaa ttttatgggc tatgtcattg   840
gatgttatgg gtccttgcca caagaacaca tcatacataa aatcaaagaa tgttttagaa   900
aacttcctgt taacaggcct attgattgga aagt                                934
```

<210> SEQ ID NO 16
<211> LENGTH: 310
<212> TYPE: PRT
<213> ORGANISM: Hep B virus
<220> FEATURE:
<221> NAME/KEY: MISC_FEATURE
<222> LOCATION: (205)..(205)
<223> OTHER INFORMATION: "n" = any nucleotide
<220> FEATURE:
<221> NAME/KEY: MISC_FEATURE
<222> LOCATION: (229)..(229)
<223> OTHER INFORMATION: "n" = any nucleotide
<220> FEATURE:
<221> NAME/KEY: MISC_FEATURE
<222> LOCATION: (232)..(232)
<223> OTHER INFORMATION: "n" = any nucleotide
<220> FEATURE:
<221> NAME/KEY: MISC_FEATURE
<222> LOCATION: (232)..(232)
<223> OTHER INFORMATION: "n" = any amino acid

<400> SEQUENCE: 16

```
Pro Cys Trp Trp Leu Gln Phe Arg Asn Ser Lys Pro Cys Ser Asp Tyr
1               5                   10                  15

Cys Leu Ser His Ile Val Asn Leu Leu Glu Asp Trp Gly Pro Cys Ala
            20                  25                  30

Glu Tyr Gly Glu His His Ile Arg Ile Pro Arg Thr Pro Ser Arg Val
        35                  40                  45

Thr Gly Gly Val Phe Leu Val Asp Lys Asn Pro His Asn Thr Ala Glu
    50                  55                  60

Ser Arg Val Val Val Asp Phe Ser Gln Phe Ser Arg Gly Asn His Arg
65                  70                  75                  80

Val Ser Trp Pro Lys Phe Ala Val Pro Asn Leu Gln Ser Leu Thr Asn
                85                  90                  95
```

```
Leu Leu Ser Ser Asp Leu Thr Trp Leu Ser Leu Asp Val Thr Ala Ala
            100                 105                 110

Phe Tyr His Ile Pro Leu His Pro Ala Ala Met Pro His Leu Leu Val
            115                 120                 125

Gly Ser Ser Gly Leu Ser Arg Tyr Val Ala Arg Leu Ser Ser Asn Ser
            130                 135                 140

Arg Ile Leu Asn His Gln His Gly Asn Met Pro Asn Leu His Asp Ser
145                 150                 155                 160

Cys Ser Arg Asn Leu Tyr Val Ser Leu Leu Leu Leu Tyr Gln Thr Phe
                165                 170                 175

Gly Arg Lys Leu His Leu Tyr Ser His Pro Ile Ile Leu Gly Phe Arg
                180                 185                 190

Lys Ile Pro Met Gly Val Gly Leu Ser Pro Phe Leu Xaa Ala Gln Phe
                195                 200                 205

Gly Ser Ala Ile Cys Ser Val Val Arg Arg Ala Phe Pro His Cys Leu
            210                 215                 220

Ala Phe Ile Tyr Xaa Asp Asp Xaa Val Leu Gly Ala Lys Ser Val Gln
225                 230                 235                 240

His Leu Glu Ser Leu Phe Thr Ala Val Thr Asn Phe Leu Leu Ser Leu
                245                 250                 255

Gly Ile His Leu Asn Pro Asn Lys Thr Lys Arg Trp Gly Tyr Ser Leu
                260                 265                 270

Asn Phe Met Gly Tyr Val Ile Gly Cys Tyr Gly Ser Leu Pro Gln Glu
            275                 280                 285

His Ile Ile His Lys Ile Lys Glu Cys Phe Arg Lys Leu Pro Val Asn
            290                 295                 300

Arg Pro Ile Asp Trp Lys
305                 310

<210> SEQ ID NO 17
<211> LENGTH: 258
<212> TYPE: PRT
<213> ORGANISM: Hep B virus
<220> FEATURE:
<221> NAME/KEY: MISC_FEATURE
<222> LOCATION: (78)..(78)
<223> OTHER INFORMATION: "n" = any nucleotide
<220> FEATURE:
<221> NAME/KEY: MISC_FEATURE
<222> LOCATION: (228)..(228)
<223> OTHER INFORMATION: "n" = any nucleotide
<220> FEATURE:
<221> NAME/KEY: MISC_FEATURE
<222> LOCATION: (230)..(230)
<223> OTHER INFORMATION: "n" = any nucleotide
<220> FEATURE:
<221> NAME/KEY: MISC_FEATURE
<222> LOCATION: (230)..(230)
<223> OTHER INFORMATION: "n" = any amino acid

<400> SEQUENCE: 17

Pro Pro Ala Gly Gly Ser Ser Gly Thr Val Asn Pro Val Pro Thr
1               5                   10                  15

Thr Ala Ser His Ile Ser Ser Ile Phe Ser Arg Ile Gly Asp Pro Ala
            20                  25                  30

Leu Asn Met Glu Asn Ile Thr Ser Gly Phe Leu Gly Pro Leu Leu Val
            35                  40                  45

Leu Gln Ala Gly Phe Phe Leu Leu Thr Arg Ile Leu Thr Ile Pro Gln
50                  55                  60
```

| | | | | | | | | | | | | | | | |
|---|---|---|---|---|---|---|---|---|---|---|---|---|---|---|---|
|Ser|Leu|Glu|Ser|Trp|Trp|Thr|Ser|Leu|Asn|Phe|Leu|Gly|Xaa|Thr|Thr|
|65| | | |70| | | |75| | | |80| | | |

| | | | | | | | | | | |
|---|---|---|---|---|---|---|---|---|---|---|
|Val|Cys|Leu|Gly|Gln|Asn|Ser|Gln|Ser|Pro|Thr|Ser|Asn|His|Ser|Pro|
| | | | |85| | | |90| | | |95| | | |

Ser Leu Glu Ser Trp Trp Thr Ser Leu Asn Phe Leu Gly Xaa Thr Thr
65                  70                  75                  80

Val Cys Leu Gly Gln Asn Ser Gln Ser Pro Thr Ser Asn His Ser Pro
                85                  90                  95

Thr Ser Cys Pro Pro Thr Pro Gly Tyr Arg Trp Met Leu Arg His Phe
            100                 105                 110

Ile Ile Phe Leu Phe Ile Leu Leu Cys Leu Ile Phe Leu Leu Val
        115                 120                 125

Leu Leu Asp Tyr Gln Gly Met Leu Pro Val Cys Pro Leu Ile Pro Gly
        130                 135                 140

Ser Ser Thr Thr Ser Thr Gly Thr Cys Arg Thr Cys Thr Thr Pro Ala
145                 150                 155                 160

Gln Gly Thr Ser Met Tyr Pro Ser Cys Cys Thr Lys Pro Ser Asp
            165                 170                 175

Gly Asn Cys Thr Cys Ile Pro Ile Pro Ser Ser Trp Ala Phe Gly Lys
            180                 185                 190

Phe Leu Trp Glu Trp Ala Ser Ala Arg Phe Ser Trp Leu Ser Leu Val
        195                 200                 205

Val Pro Phe Val Gln Trp Phe Val Gly Leu Ser Pro Thr Val Trp Leu
210                 215                 220

Ser Phe Met Xaa Met Xaa Trp Tyr Trp Gly Pro Ser Leu Tyr Ser Ile
225                 230                 235                 240

Leu Ser Pro Phe Leu Pro Leu Leu Pro Ile Phe Phe Cys Leu Trp Val
            245                 250                 255

Tyr Ile

<210> SEQ ID NO 18
<211> LENGTH: 932
<212> TYPE: DNA
<213> ORGANISM: Hep B virus

<400> SEQUENCE: 18

```
tcccctgctg gtggctccag ttccggaaca gtaaaccctg ttccgactac tgcctctcac      60
atatcgtcaa tcttctcgag gattggggac cctgcgctga atatggagaa catcacatca     120
ggattcctag gacccttct cgtgttacag gcggggtttt tcttgttgac aagaatcctc      180
acaataccgc agagtctaga gtcgtggtgg acttctctca attttctagg ggcaaccacc     240
gtgtgtcttg gccaaaattc gcagtcccca acctccaatc actcaccaac ctcctgtcct     300
ccgacttgac ctggttatcg ctggatgtga ctgcggcatt ttatcatatt cctcttcatc     360
ctgctgctat gcctcatctt cttgttggtt cttctggact atcaaggtat gttgcccgtt     420
tgtcctctaa ttccaggatc ctcaaccacc agcacgggaa catgccgaac ttgcacgact     480
cctgctcaag gaacctctat gtatccctcc tgttgctgta ccaaaccttc ggacggaaat     540
tgcacctgta ttcccatccc atcatcctgg gctttcggaa aattcctatg ggagtgggcc     600
tcagcccgtt tctcctggct cagtttggta gtgccatttg ttcagtggtt cgtagggctt     660
tcccccactg tttggctttc atttatgcgg atgatgtggt attggggggcc aagtctgtac     720
agcatcttga gtccctttt accgctgtta ccaattttct tttgtctctg ggtatacatt     780
tgaaccctaa caaaacaaag agatgggggtt actccctaaa ttttatgggc tatgtcattg     840
gatgttatgg gtccttgcca caagaacaca tcatacataa aatcaaagaa tgttttagaa     900
aacttcctgt taacaggcct attgattgga aa                                   932
```

<210> SEQ ID NO 19
<211> LENGTH: 310
<212> TYPE: PRT
<213> ORGANISM: Hep B virus

<400> SEQUENCE: 19

Pro Cys Trp Trp Leu Gln Phe Arg Asn Ser Lys Pro Cys Ser Asp Tyr
1               5                   10                  15

Cys Leu Ser His Ile Val Asn Leu Leu Glu Asp Trp Gly Pro Cys Ala
            20                  25                  30

Glu Tyr Gly Glu His His Ile Arg Ile Pro Arg Thr Pro Ser Arg Val
        35                  40                  45

Thr Gly Gly Val Phe Leu Val Asp Lys Asn Pro His Asn Thr Ala Glu
    50                  55                  60

Ser Arg Val Val Val Asp Phe Ser Gln Phe Ser Arg Gly Asn His Arg
65                  70                  75                  80

Val Ser Trp Pro Lys Phe Ala Val Pro Asn Leu Gln Ser Leu Thr Asn
                85                  90                  95

Leu Leu Ser Ser Asp Leu Thr Trp Leu Ser Leu Asp Val Thr Ala Ala
            100                 105                 110

Phe Tyr His Ile Pro Leu His Pro Ala Ala Met Pro His Leu Leu Val
        115                 120                 125

Gly Ser Ser Gly Leu Ser Arg Tyr Val Ala Arg Leu Ser Ser Asn Ser
    130                 135                 140

Arg Ile Leu Asn His Gln His Gly Asn Met Pro Asn Leu His Asp Ser
145                 150                 155                 160

Cys Ser Arg Asn Leu Tyr Val Ser Leu Leu Leu Leu Tyr Gln Thr Phe
                165                 170                 175

Gly Arg Lys Leu His Leu Tyr Ser His Pro Ile Ile Leu Gly Phe Arg
            180                 185                 190

Lys Ile Pro Met Gly Val Gly Leu Ser Pro Phe Leu Leu Ala Gln Phe
        195                 200                 205

Gly Ser Ala Ile Cys Ser Val Val Arg Arg Ala Phe Pro His Cys Leu
    210                 215                 220

Ala Phe Ile Tyr Ala Asp Asp Val Val Leu Gly Ala Lys Ser Val Gln
225                 230                 235                 240

His Leu Glu Ser Leu Phe Thr Ala Val Thr Asn Phe Leu Leu Ser Leu
                245                 250                 255

Gly Ile His Leu Asn Pro Asn Lys Thr Lys Arg Trp Gly Tyr Ser Leu
            260                 265                 270

Asn Phe Met Gly Tyr Val Ile Gly Cys Tyr Gly Ser Leu Pro Gln Glu
        275                 280                 285

His Ile Ile His Lys Ile Lys Glu Cys Phe Arg Lys Leu Pro Val Asn
    290                 295                 300

Arg Pro Ile Asp Trp Lys
305                 310

<210> SEQ ID NO 20
<211> LENGTH: 258
<212> TYPE: PRT
<213> ORGANISM: Hep B virus

<400> SEQUENCE: 20

Ser Pro Ala Gly Gly Ser Ser Ser Gly Thr Val Asn Pro Val Pro Thr
1               5                   10                  15

Thr Ala Ser His Ile Ser Ser Ile Phe Ser Arg Ile Gly Asp Pro Ala

```
                20                  25                  30
Leu Asn Met Glu Asn Ile Thr Ser Gly Phe Leu Gly Pro Leu Leu Val
            35                  40                  45

Leu Gln Ala Gly Phe Phe Leu Leu Thr Arg Ile Leu Thr Ile Pro Gln
     50                  55                  60

Ser Leu Glu Ser Trp Trp Thr Ser Leu Asn Phe Leu Gly Ala Thr Thr
 65                  70                  75                  80

Val Cys Leu Gly Gln Asn Ser Gln Ser Pro Thr Ser Asn His Ser Pro
                 85                  90                  95

Thr Ser Cys Pro Pro Thr Pro Gly Tyr Arg Trp Met Leu Arg His Phe
            100                 105                 110

Ile Ile Phe Leu Phe Ile Leu Leu Cys Leu Ile Phe Leu Leu Val
            115                 120                 125

Leu Leu Asp Tyr Gln Gly Met Leu Pro Val Cys Pro Leu Ile Pro Gly
     130                 135                 140

Ser Ser Thr Thr Ser Thr Gly Thr Cys Arg Thr Cys Thr Thr Pro Ala
145                 150                 155                 160

Gln Gly Thr Ser Met Tyr Pro Ser Cys Cys Thr Lys Pro Ser Asp
                165                 170                 175

Gly Asn Cys Thr Cys Ile Pro Ile Pro Ser Ser Trp Ala Phe Gly Lys
            180                 185                 190

Phe Leu Trp Glu Trp Ala Ser Ala Arg Phe Ser Trp Leu Ser Leu Val
     195                 200                 205

Val Pro Phe Val Gln Trp Phe Val Gly Leu Ser Pro Thr Val Trp Leu
210                 215                 220

Ser Phe Met Arg Met Met Trp Tyr Trp Gly Pro Ser Leu Tyr Ser Ile
225                 230                 235                 240

Leu Ser Pro Phe Leu Pro Leu Leu Pro Ile Phe Phe Cys Leu Trp Val
                245                 250                 255

Tyr Ile

<210> SEQ ID NO 21
<211> LENGTH: 934
<212> TYPE: DNA
<213> ORGANISM: Hep B virus

<400> SEQUENCE: 21
tcccctgctg gtggctccag ttccggaaca gtaaaccctg ttccgactac tgcctctcac      60
atatcgtcaa tcttctcgag gattggggac cctgcgctga atatggagaa catcacatca     120
ggattcctag gaccccttct cgtgttacag gcggggtttt tcttgttgac aagaatcctc     180
acaataccgc agagtctaga ctcgtggtgg acttctctca attttctagg ggaaccacc     240 gtgtgtcttg gccaaaattc gcagtcccca acctccaatc actcaccaac ctcctgtcct     300
ccgacttgac ctggttatcg ctggatgtga ctgcggcatt ttatcatatt cctcttcatc     360
ctgctgctat gcctcatctt cttgttggtt cttctggact atcaaggtat gttgcccgtt     420
tgtcctctaa ttccaggatc ctcaaccacc agcacgggaa catgccgaac ttgcacgact     480
cctgctcaag gaacctctat gtatccctcc tgttgctgta ccaaaccttc ggacggaaat     540
tgcacctgta ttcccatccc atcatcctgg ctttcggaa aattcctatg ggagtgggcc     600
tcagcccgtt tctcctggct cagtttggta gtgccatttg ttcagtggtt cgtagggctt     660
tcccccactg tttggctttc atttatgcgg atgatrtggt attgggggcc aagtctgtac     720
agcatcttga gtcccttttt accgctgtta ccaatttttct tttgtctctg ggtatacatt     780
```

-continued

```
tggyccctma caaaacaaag agatgggtt actccctaaa ttttatgggc tatgtcattg    840
gatgttatgg gtccttgcca caagaacaca tcatacataa aatcaaagaa tgttttagaa    900
aacttcctgt taacaggcct attgattgga aagt                                934
```

<210> SEQ ID NO 22
<211> LENGTH: 310
<212> TYPE: PRT
<213> ORGANISM: Hep B virus
<220> FEATURE:
<221> NAME/KEY: MISC_FEATURE
<222> LOCATION: (232)..(232)
<223> OTHER INFORMATION: "n" = any amino acid
<220> FEATURE:
<221> NAME/KEY: MISC_FEATURE
<222> LOCATION: (261)..(261)
<223> OTHER INFORMATION: "n" = any amino acid
<220> FEATURE:
<221> NAME/KEY: MISC_FEATURE
<222> LOCATION: (263)..(263)
<223> OTHER INFORMATION: "n" = any amino acid

<400> SEQUENCE: 22

```
Pro Cys Trp Trp Leu Gln Phe Arg Asn Ser Lys Pro Cys Ser Asp Tyr
1               5                   10                  15

Cys Leu Ser His Ile Val Asn Leu Leu Glu Asp Trp Gly Pro Cys Ala
            20                  25                  30

Glu Tyr Gly Glu His His Ile Arg Ile Pro Arg Thr Pro Ser Arg Val
        35                  40                  45

Thr Gly Gly Val Phe Leu Val Asp Lys Asn Pro His Asn Thr Ala Glu
    50                  55                  60

Ser Arg Leu Val Val Asp Phe Ser Gln Phe Ser Arg Gly Asn His Arg
65                  70                  75                  80

Val Ser Trp Pro Lys Phe Ala Val Pro Asn Leu Gln Ser Leu Thr Asn
                85                  90                  95

Leu Leu Ser Ser Asp Leu Thr Trp Leu Ser Leu Asp Val Thr Ala Ala
            100                 105                 110

Phe Tyr His Ile Pro Leu His Pro Ala Ala Met Pro His Leu Leu Val
        115                 120                 125

Gly Ser Ser Gly Leu Ser Arg Tyr Val Ala Arg Leu Ser Ser Asn Ser
    130                 135                 140

Arg Ile Leu Asn His Gln His Gly Asn Met Pro Asn Leu His Asp Ser
145                 150                 155                 160

Cys Ser Arg Asn Leu Tyr Val Ser Leu Leu Leu Leu Tyr Gln Thr Phe
                165                 170                 175

Gly Arg Lys Leu His Leu Tyr Ser His Pro Ile Ile Leu Gly Phe Arg
            180                 185                 190

Lys Ile Pro Met Gly Val Gly Leu Ser Pro Phe Leu Leu Ala Gln Phe
        195                 200                 205

Gly Ser Ala Ile Cys Ser Val Val Arg Arg Ala Phe Pro His Cys Leu
    210                 215                 220

Ala Phe Ile Tyr Ala Asp Asp Xaa Val Leu Gly Ala Lys Ser Val Gln
225                 230                 235                 240

His Leu Glu Ser Leu Phe Thr Ala Val Thr Asn Phe Leu Leu Ser Leu
                245                 250                 255

Gly Ile His Leu Xaa Pro Xaa Lys Thr Lys Arg Trp Gly Tyr Ser Leu
            260                 265                 270

Asn Phe Met Gly Tyr Val Ile Gly Cys Tyr Gly Ser Leu Pro Gln Glu
```

-continued

```
                275                 280                 285
His Ile Ile His Lys Ile Lys Glu Cys Phe Arg Lys Leu Pro Val Asn
    290                 295                 300

Arg Pro Ile Asp Trp Lys
305                 310

<210> SEQ ID NO 23
<211> LENGTH: 270
<212> TYPE: PRT
<213> ORGANISM: Hep B virus
<220> FEATURE:
<221> NAME/KEY: MISC_FEATURE
<222> LOCATION: (230)..(230)
<223> OTHER INFORMATION: "n" = any amino acid
<220> FEATURE:
<221> NAME/KEY: MISC_FEATURE
<222> LOCATION: (260)..(260)
<223> OTHER INFORMATION: "n" = any amino acid

<400> SEQUENCE: 23

Ser Pro Ala Gly Gly Ser Ser Gly Thr Val Asn Pro Val Pro Thr
1               5                   10                  15

Thr Ala Ser His Ile Ser Ser Ile Phe Ser Arg Ile Gly Asp Pro Ala
            20                  25                  30

Leu Asn Met Glu Asn Ile Thr Ser Gly Phe Leu Gly Pro Leu Leu Val
        35                  40                  45

Leu Gln Ala Gly Phe Phe Leu Leu Thr Arg Ile Leu Thr Ile Pro Gln
    50                  55                  60

Ser Leu Asp Ser Trp Trp Thr Ser Leu Asn Phe Leu Gly Gly Thr Thr
65                  70                  75                  80

Val Cys Leu Gly Gln Asn Ser Gln Ser Pro Thr Ser Asn His Ser Pro
                85                  90                  95

Thr Ser Cys Pro Pro Thr Pro Gly Tyr Arg Trp Met Leu Arg His Phe
            100                 105                 110

Ile Ile Phe Leu Phe Ile Leu Leu Leu Cys Leu Ile Phe Leu Leu Val
        115                 120                 125

Leu Leu Asp Tyr Gln Gly Met Leu Pro Val Cys Pro Leu Ile Pro Gly
    130                 135                 140

Ser Ser Thr Thr Ser Thr Gly Thr Cys Arg Thr Cys Thr Thr Pro Ala
145                 150                 155                 160

Gln Gly Thr Ser Met Tyr Pro Ser Cys Cys Cys Thr Lys Pro Ser Asp
                165                 170                 175

Gly Asn Cys Thr Cys Ile Pro Ile Pro Ser Ser Trp Ala Phe Gly Lys
            180                 185                 190

Phe Leu Trp Glu Trp Ala Ser Ala Arg Phe Ser Trp Leu Ser Leu Val
        195                 200                 205

Val Pro Phe Val Gln Trp Phe Val Gly Leu Ser Pro Thr Val Trp Leu
    210                 215                 220

Ser Phe Met Arg Met Xaa Trp Tyr Trp Gly Pro Ser Leu Tyr Ser Ile
225                 230                 235                 240

Leu Ser Pro Phe Leu Pro Leu Leu Pro Ile Phe Phe Cys Leu Trp Val
                245                 250                 255

Tyr Ile Trp Xaa Leu Thr Lys Gln Arg Asp Gly Val Thr Pro
            260                 265                 270

<210> SEQ ID NO 24
<211> LENGTH: 892
<212> TYPE: DNA
```

<213> ORGANISM: Hep B virus

<400> SEQUENCE: 24

```
tcccctgctg gtggctccag ttccggaaca gtaaaccgtg ttccgactac tgcctctcac      60
atatcgtcaa tcttctcgag gattggggac cctgcgctga atatggagaa catcacatca     120
ggattcctag gacccccttct cgtgttacag gcggggtttt tcttgttgac aagaatcctc    180
acaataccgc agagtctaga ctcgtggtgg acttctctca attttctagg ggaaccacc      240
gtgtgtcttg gccaaaattc gcagtcccca acctccaatc actcaccaac ctcctgtcct     300
ccgacttgac ctggttatcg ctggatgtga ctgcggcatt ttatcatatt cctcttcatc     360
ctgctgctat gcctcatctt cttgttggtt cttctggact atcaaggtat gttgcccgtt     420
tgtcctctaa ttccaggatc ctcaaccacc agcacgggaa catgccgaac ttgcacgact     480
cctgctcaag gaacctctat gtatccctcc tgttgctgta ccaaaccttc ggacggaaat     540
tgcacctgta ttcccatccc atcatcctgg gctttcggaa aattcctatg ggagtgggcc     600
tcagcccgtt tctcctggct cagtttggta gtgccatttg ttcagtggtt cgtagggctt     660
tcccccactg tttggctttc atttatgcgg atgatrtggt attgggggcc aagtctgtac     720
agcatcttga gtcccttttt accgctgtta ccaattttct tttgtctctg ggtatacatt     780
tggyccctma caaaacaaag agatggggtt actccctaaa ttttatgggc tatgtcattg     840
gatgttatgg gtccttgcca caagaacaca tcatacataa aatcaagaa tg              892
```

<210> SEQ ID NO 25
<211> LENGTH: 296
<212> TYPE: PRT
<213> ORGANISM: Hep B virus
<220> FEATURE:
<221> NAME/KEY: MISC_FEATURE
<222> LOCATION: (232)..(232)
<223> OTHER INFORMATION: "n" = any amino acid
<220> FEATURE:
<221> NAME/KEY: MISC_FEATURE
<222> LOCATION: (261)..(261)
<223> OTHER INFORMATION: "n" = any amino acid
<220> FEATURE:
<221> NAME/KEY: MISC_FEATURE
<222> LOCATION: (263)..(263)
<223> OTHER INFORMATION: "n" = any amino acid

<400> SEQUENCE: 25

```
Pro Cys Trp Trp Leu Gln Phe Arg Asn Ser Lys Pro Cys Ser Asp Tyr
1               5                   10                  15

Cys Leu Ser His Ile Val Asn Leu Leu Glu Asp Trp Gly Pro Cys Ala
            20                  25                  30

Glu Tyr Gly Glu His His Ile Arg Ile Pro Arg Thr Pro Ser Arg Val
        35                  40                  45

Thr Gly Gly Val Phe Leu Val Asp Lys Asn Pro His Asn Thr Ala Glu
    50                  55                  60

Ser Arg Leu Val Val Asp Phe Ser Gln Phe Ser Arg Gly Asn His Arg
65                  70                  75                  80

Val Ser Trp Pro Lys Phe Ala Val Pro Asn Leu Gln Ser Leu Thr Asn
                85                  90                  95

Leu Leu Ser Ser Asp Leu Thr Trp Leu Ser Leu Asp Val Thr Ala Ala
            100                 105                 110

Phe Tyr His Ile Pro Leu His Pro Ala Ala Met Pro His Leu Leu Val
        115                 120                 125

Gly Ser Ser Gly Leu Ser Arg Tyr Val Ala Arg Leu Ser Ser Asn Ser
```

```
            130                 135                 140
Arg Ile Leu Asn His Gln His Gly Asn Met Pro Asn Leu His Asp Ser
145                 150                 155                 160

Cys Ser Arg Asn Leu Tyr Val Ser Leu Leu Leu Tyr Gln Thr Phe
                165                 170                 175

Gly Arg Lys Leu His Leu Tyr Ser His Pro Ile Ile Leu Gly Phe Arg
            180                 185                 190

Lys Ile Pro Met Gly Val Gly Leu Ser Pro Phe Leu Leu Ala Gln Phe
                195                 200                 205

Gly Ser Ala Ile Cys Ser Val Val Arg Arg Ala Phe Pro His Cys Leu
            210                 215                 220

Ala Phe Ile Tyr Ala Asp Asp Xaa Val Leu Gly Ala Lys Ser Val Gln
225                 230                 235                 240

His Leu Glu Ser Leu Phe Thr Ala Val Thr Asn Phe Leu Leu Ser Leu
                245                 250                 255

Gly Ile His Leu Xaa Pro Xaa Lys Thr Lys Arg Trp Gly Tyr Ser Leu
            260                 265                 270

Asn Phe Met Gly Tyr Val Ile Gly Cys Tyr Gly Ser Leu Pro Gln Glu
                275                 280                 285

His Ile Ile His Lys Ile Lys Glu
        290                 295

<210> SEQ ID NO 26
<211> LENGTH: 270
<212> TYPE: PRT
<213> ORGANISM: Hep B virus
<220> FEATURE:
<221> NAME/KEY: MISC_FEATURE
<222> LOCATION: (230)..(230)
<223> OTHER INFORMATION: "n" = any amino acid
<220> FEATURE:
<221> NAME/KEY: MISC_FEATURE
<222> LOCATION: (260)..(260)
<223> OTHER INFORMATION: "n" = any amino acid

<400> SEQUENCE: 26

Ser Pro Ala Gly Gly Ser Ser Gly Thr Val Asn Arg Val Pro Thr
1               5                   10                  15

Thr Ala Ser His Ile Ser Ser Ile Phe Ser Arg Ile Gly Asp Pro Ala
                20                  25                  30

Leu Asn Met Glu Asn Ile Thr Ser Gly Phe Leu Gly Pro Leu Leu Val
            35                  40                  45

Leu Gln Ala Gly Phe Phe Leu Leu Thr Arg Ile Leu Thr Ile Pro Gln
50                  55                  60

Ser Leu Asp Ser Trp Trp Thr Ser Leu Asn Phe Leu Gly Gly Thr Thr
65                  70                  75                  80

Val Cys Leu Gly Gln Asn Ser Gln Ser Pro Thr Ser Asn His Ser Pro
                85                  90                  95

Thr Ser Cys Pro Pro Thr Pro Gly Tyr Arg Trp Met Leu Arg His Phe
            100                 105                 110

Ile Ile Phe Leu Phe Ile Leu Leu Cys Leu Ile Phe Leu Leu Val
                115                 120                 125

Leu Leu Asp Tyr Gln Gly Met Leu Pro Val Cys Pro Leu Ile Pro Gly
            130                 135                 140

Ser Ser Thr Thr Ser Thr Gly Thr Cys Arg Thr Cys Thr Thr Pro Ala
145                 150                 155                 160

Gln Gly Thr Ser Met Tyr Pro Ser Cys Cys Cys Thr Lys Pro Ser Asp
```

-continued

```
               165                 170                 175
Gly Asn Cys Thr Cys Ile Pro Ile Pro Ser Ser Trp Ala Phe Gly Lys
            180                 185                 190

Phe Leu Trp Glu Trp Ala Ser Ala Arg Phe Ser Trp Leu Ser Leu Val
        195             200             205

Val Pro Phe Val Gln Trp Phe Val Gly Leu Ser Pro Thr Val Trp Leu
    210             215             220

Ser Phe Met Arg Met Xaa Trp Tyr Trp Gly Pro Ser Leu Tyr Ser Ile
225             230             235             240

Leu Ser Pro Phe Leu Pro Leu Leu Pro Ile Phe Phe Cys Leu Trp Val
            245             250             255

Tyr Ile Trp Xaa Leu Thr Lys Gln Arg Asp Gly Val Thr Pro
            260             265             270
```